(12) United States Patent
Curry et al.

(10) Patent No.: US 8,764,657 B2
(45) Date of Patent: Jul. 1, 2014

(54) MEDICAL DEVICE INSERTERS AND PROCESSES OF INSERTING AND USING MEDICAL DEVICES

(75) Inventors: Samuel Mason Curry, Oakland, CA (US); Manuel Luis Donnay, San Francisco, CA (US); Tuan Nguyen, Dublin, CA (US); Louis G. Pace, San Carlos, CA (US); Peter G. Robinson, Alamo, CA (US); Philip Yee, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 22 days.

(21) Appl. No.: 13/436,816

(22) Filed: Mar. 30, 2012

(65) Prior Publication Data

US 2012/0190951 A1 Jul. 26, 2012

Related U.S. Application Data

(63) Continuation of application No. 13/071,487, filed on Mar. 24, 2011.

(60) Provisional application No. 61/317,243, filed on Mar. 24, 2010, provisional application No. 61/345,562, filed on May 17, 2010, provisional application No. 61/361,374, filed on Jul. 2, 2010, provisional application No. 61/411,262, filed on Nov. 8, 2010.

(51) Int. Cl.
*A61B 5/00* (2006.01)

(52) U.S. Cl.
USPC ........... 600/309; 600/345; 600/347; 600/365; 600/583; 606/181; 606/185

(58) Field of Classification Search
USPC .......... 606/108, 116, 117, 181–185; 604/11–18, 59–64, 216; 600/309, 316, 600/319, 320, 322, 345–347, 583, 365
See application file for complete search history.

(56) References Cited

U.S. PATENT DOCUMENTS

| 3,123,790 A | 3/1964 | Tyler |
| 3,260,656 A | 7/1966 | Ross, Jr. |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |

(Continued)

FOREIGN PATENT DOCUMENTS

| CA | 2291105 | 12/1998 |
| DE | 4401400 | 7/1995 |

(Continued)

OTHER PUBLICATIONS

Alcock, S. J., et al., "Continuous Analyte Monitoring to Aid Clinical Practice", *IEEE Engineering in Medicine and Biology Magazine*, 1994, pp. 319-325.

(Continued)

*Primary Examiner* — Kathleen Holwerda
(74) *Attorney, Agent, or Firm* — Jackson & Co., LLP

(57) ABSTRACT

An apparatus for insertion of a medical device in the skin of a subject is provided, as well as methods of inserting medical devices.

9 Claims, 54 Drawing Sheets

(56) References Cited

U.S. PATENT DOCUMENTS

| | | | |
|---|---|---|---|
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |

(56) References Cited

U.S. PATENT DOCUMENTS

| | | |
|---|---|---|
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,545,191 A | 8/1996 | Mann et al. |
| 5,549,568 A * | 8/1996 | Shields ................... 604/192 |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |

(56) References Cited

U.S. PATENT DOCUMENTS

| | | | |
|---|---|---|---|
| 5,851,197 A | 12/1998 | Marano et al. | |
| 5,858,001 A | 1/1999 | Tsals et al. | |
| 5,865,804 A | 2/1999 | Bachynsky | |
| 5,885,211 A | 3/1999 | Eppstein et al. | |
| 5,899,855 A | 5/1999 | Brown | |
| 5,924,979 A | 7/1999 | Swedlow et al. | |
| 5,925,021 A | 7/1999 | Castellano et al. | |
| 5,931,868 A | 8/1999 | Gross et al. | |
| 5,948,006 A | 9/1999 | Mann | |
| 5,951,521 A | 9/1999 | Mastrototaro et al. | |
| 5,954,643 A | 9/1999 | Van Antwerp | |
| 5,954,685 A | 9/1999 | Tierny | |
| 5,957,854 A | 9/1999 | Besson et al. | |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,972,199 A | 10/1999 | Heller et al. | |
| 5,987,353 A | 11/1999 | Khatchatrian et al. | |
| 5,993,411 A | 11/1999 | Choi | |
| 5,995,860 A | 11/1999 | Sun et al. | |
| 5,997,501 A | 12/1999 | Gross et al. | |
| 6,001,067 A | 12/1999 | Shults et al. | |
| 6,004,278 A | 12/1999 | Botich et al. | |
| 6,022,368 A | 2/2000 | Gavronsky et al. | |
| 6,024,699 A | 2/2000 | Surwit et al. | |
| 6,026,321 A | 2/2000 | Miyata et al. | |
| 6,027,459 A | 2/2000 | Shain et al. | |
| 6,049,727 A | 4/2000 | Crothall | |
| 6,056,718 A | 5/2000 | Funderburk et al. | |
| 6,068,399 A | 5/2000 | Tseng | |
| 6,083,710 A | 7/2000 | Heller et al. | |
| 6,088,608 A | 7/2000 | Schulman et al. | |
| 6,091,975 A | 7/2000 | Daddona et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,143,164 A | 11/2000 | Heller et al. | |
| 6,159,147 A | 12/2000 | Lichter et al. | |
| 6,162,611 A | 12/2000 | Heller et al. | |
| 6,175,752 B1 | 1/2001 | Say et al. | |
| 6,186,982 B1 | 2/2001 | Gross et al. | |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,254,536 B1 | 7/2001 | DeVito | |
| 6,254,586 B1 | 7/2001 | Mann et al. | |
| 6,275,717 B1 | 8/2001 | Gross et al. | |
| 6,283,761 B1 | 9/2001 | Joao | |
| 6,283,982 B1 | 9/2001 | Levaughn et al. | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,331,244 B1 | 12/2001 | Lewis et al. | |
| 6,338,790 B1 | 1/2002 | Feldman et al. | |
| 6,348,640 B1 | 2/2002 | Navot et al. | |
| 6,359,444 B1 | 3/2002 | Grimes | |
| 6,360,888 B1 | 3/2002 | McIvor et al. | |
| 6,366,794 B1 | 4/2002 | Moussy et al. | |
| 6,368,141 B1 | 4/2002 | Van Antwerp et al. | |
| 6,368,274 B1 | 4/2002 | Van Antwerp et al. | |
| 6,377,828 B1 | 4/2002 | Chaiken et al. | |
| 6,379,301 B1 | 4/2002 | Worthington et al. | |
| 6,409,740 B1 | 6/2002 | Kuhr et al. | |
| 6,418,332 B1 | 7/2002 | Mastrototaro et al. | |
| 6,424,847 B1 | 7/2002 | Mastrototaro et al. | |
| 6,427,088 B1 | 7/2002 | Bowman, IV et al. | |
| 6,437,679 B1 | 8/2002 | Roques | |
| 6,440,068 B1 | 8/2002 | Brown et al. | |
| 6,445,374 B2 | 9/2002 | Albert et al. | |
| 6,478,736 B1 | 11/2002 | Mault | |
| 6,482,176 B1 | 11/2002 | Wich | |
| 6,484,045 B1 | 11/2002 | Holker et al. | |
| 6,484,046 B1 | 11/2002 | Say et al. | |
| 6,514,718 B2 | 2/2003 | Heller et al. | |
| 6,520,326 B2 | 2/2003 | McIvor et al. | |
| 6,522,927 B1 | 2/2003 | Bishay et al. | |
| 6,551,494 B1 | 4/2003 | Heller et al. | |
| 6,554,795 B2 | 4/2003 | Lam et al. | |
| 6,558,320 B1 | 5/2003 | Causey, III et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,572,566 B2 | 6/2003 | Effenhauser | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,589,229 B1 | 7/2003 | Connelly et al. | |
| 6,591,125 B1 | 7/2003 | Buse et al. | |
| 6,595,919 B2 | 7/2003 | Berner et al. | |
| 6,605,200 B1 | 8/2003 | Mao et al. | |
| 6,605,201 B1 | 8/2003 | Mao et al. | |
| 6,607,509 B2 | 8/2003 | Bobroff et al. | |
| 6,610,012 B2 | 8/2003 | Mault | |
| 6,633,772 B2 | 10/2003 | Ford et al. | |
| 6,635,014 B2 | 10/2003 | Starkweather et al. | |
| 6,648,821 B2 | 11/2003 | Lebel et al. | |
| 6,654,625 B1 | 11/2003 | Say et al. | |
| 6,659,948 B2 | 12/2003 | Lebel et al. | |
| 6,668,196 B1 | 12/2003 | Villegas et al. | |
| 6,676,290 B1 | 1/2004 | Lu | |
| 6,687,546 B2 | 2/2004 | Lebel et al. | |
| 6,689,056 B1 | 2/2004 | Kilcoyne et al. | |
| 6,694,191 B2 | 2/2004 | Starkweather et al. | |
| 6,695,860 B1 * | 2/2004 | Ward et al. | 606/185 |
| 6,702,857 B2 | 3/2004 | Brauker et al. | |
| 6,733,446 B2 | 5/2004 | Lebel et al. | |
| 6,740,075 B2 | 5/2004 | Lebel et al. | |
| 6,741,877 B1 | 5/2004 | Shults et al. | |
| 6,746,582 B2 | 6/2004 | Heller et al. | |
| 6,758,810 B2 | 7/2004 | Lebel et al. | |
| 6,770,030 B2 | 8/2004 | Schaupp et al. | |
| 6,790,178 B1 | 9/2004 | Mault et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,830,551 B1 | 12/2004 | Uchigaki et al. | |
| 6,837,858 B2 | 1/2005 | Cunningham et al. | |
| 6,837,988 B2 | 1/2005 | Leong et al. | |
| 6,849,052 B2 | 2/2005 | Ughigaki et al. | |
| 6,854,882 B2 | 2/2005 | Chen | |
| 6,862,465 B2 | 3/2005 | Shults et al. | |
| 6,873,268 B2 | 3/2005 | Lebel et al. | |
| 6,881,551 B2 | 4/2005 | Heller et al. | |
| 6,892,085 B2 | 5/2005 | McIvor et al. | |
| 6,895,265 B2 | 5/2005 | Silver | |
| 6,931,327 B2 | 8/2005 | Goode, Jr. et al. | |
| 6,932,894 B2 | 8/2005 | Mao et al. | |
| 6,936,006 B2 | 8/2005 | Sabra | |
| 6,942,518 B2 | 9/2005 | Liamos et al. | |
| 6,950,708 B2 | 9/2005 | Bowman, IV et al. | |
| 6,958,705 B2 | 10/2005 | Lebel et al. | |
| 6,959,211 B2 | 10/2005 | Rule et al. | |
| 6,968,294 B2 | 11/2005 | Gutta et al. | |
| 6,971,274 B2 | 12/2005 | Olin | |
| 6,971,999 B2 | 12/2005 | Py et al. | |

(56) References Cited

U.S. PATENT DOCUMENTS

| | | |
|---|---|---|
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| 2001/0056262 A1 | 12/2001 | Cabiri et al. |
| 2002/0013538 A1 | 1/2002 | Teller |
| 2002/0019022 A1 | 2/2002 | Dunn et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0169369 A1 | 11/2002 | Ward et al. |
| 2002/0198444 A1 | 12/2002 | Ughigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1* | 10/2003 | Say et al. ............... 600/345 |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Steine et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0223985 A1 | 11/2004 | Dunfield et al. |
| 2004/0225338 A1 | 11/2004 | Lebel et al. |

(56) References Cited

U.S. PATENT DOCUMENTS

| | | |
|---|---|---|
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0081469 A1 | 4/2006 | Lee |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200970 A1 | 9/2006 | Brister et al. |
| 2006/0222566 A1 | 10/2006 | Brauker et al. |
| 2006/0224171 A1* | 10/2006 | Sakata et al. .................. 606/181 |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0110124 A1 | 5/2007 | Shiraki et al. |
| 2007/0123819 A1 | 5/2007 | Mernoe et al. |
| 2007/0149875 A1 | 6/2007 | Ouyang et al. |
| 2007/0156094 A1 | 7/2007 | Safabash et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154205 A1 | 6/2008 | Wojcik |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |

(56) References Cited

U.S. PATENT DOCUMENTS

| | | |
|---|---|---|
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |

(56) References Cited

U.S. PATENT DOCUMENTS

| | | |
|---|---|---|
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gryn |
| 2010/0212583 A1 | 8/2010 | Brister et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0288574 A1 | 11/2011 | Curry et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0143135 A1 | 6/2012 | Cole et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004-520898 | 7/2004 |
| WO | WO-91/15993 | 10/1991 |
| WO | WO-92/13271 | 8/1992 |
| WO | WO-94/20602 | 9/1994 |
| WO | WO-96/39977 | 5/1996 |
| WO | WO-96/25089 | 8/1996 |
| WO | WO-98/35053 | 8/1998 |
| WO | WO-98/56293 | 12/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/028784 | 4/2003 |
| WO | WO-03/076893 | 9/2003 |
| WO | WO-03/082091 | 10/2003 |
| WO | WO-2004/028337 | 4/2004 |
| WO | WO-2004/060436 | 7/2004 |
| WO | WO-2004/061420 | 7/2004 |
| WO | WO-2004/098684 | 11/2004 |
| WO | WO-2004/112602 | 12/2004 |
| WO | WO-2005/084534 | 9/2005 |
| WO | WO-2005/089103 | 9/2005 |
| WO | WO-2006/024671 | 3/2006 |
| WO | WO-2006/042811 | 4/2006 |
| WO | WO-2006/108809 | 10/2006 |
| WO | WO-2007/089738 | 8/2007 |
| WO | WO-2007/140783 | 12/2007 |
| WO | WO-2008/065646 | 6/2008 |
| WO | WO-2008/133702 | 11/2008 |
| WO | WO-2009/062675 | 5/2009 |
| WO | WO-2010/112521 | 10/2010 |
| WO | WO-2011/002815 | 1/2011 |

OTHER PUBLICATIONS

Armour, J. C., et al., "Application of Chronic Intravascular Blood Glucose Sensor in Dogs", *Diabetes*, vol. 39, 1990, pp. 1519-1526.

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.

(56) References Cited

OTHER PUBLICATIONS

Bennion, N., et al., "Alternate Site Glucose Testing: A Crossover Design", *Diabetes Technology & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Cass, A. E., et al., "Ferrocene-Medicated Enzyme Electrode for Amperometric Determination of Glucose", *Analytical Chemistry*, vol. 56, No. 4, 1984, 667-671.
Claremont, D. J., et al., "Biosensors for Continuous In Vivo Glucose Monitoring", *Proceedings of the Annual International Conference of the IEEE Engineering in Medicine and Biology Society*, vol. 10, 1988.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Feldman, B., et al., "A Continuous Glucose Sensor Based on Wired Enzyme™ Technology—Results from a 3-Day Trial in Patients with Type 1 Diabetes",*Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Heller, A., "Electrical Connection Enzyme Redox Centers to Electrodes", *Journal of Physical Chemistry*, vol. 96, No. 9, 1990, pp. 3579-3587.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Koudelka, M., et al., "In-Vivo Behaviour of Hypodermically Implanted Microfabricated Glucose Sensors", *Biosensors & Bioelectronics*, vol. 6, 1991, pp. 31-36.
Lager, W., et al., "Implantable Electrocatalytic Glucose Sensor", *Hormone Metabolic Research*, vol. 26, 1994, pp. 526-530.

Maidan, R., et al., "Elimination of Electrooxidizable Interferant-Produced Currents in Amperometric Biosensors", *Analytical Chemistry*, vol. 64, No. 23, 1992, pp. 2889-2896.
Mastrototaro, J. J., et al., "An Electroenzymatic Glucose Sensor Fabricated on a Flexible Substrate", *Sensors and Actuators B*, vol. 5, 1991, pp. 139-144.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Moatti-Sirat, D., et al., "Evaluating in Vitro and in Vivo the Interference of Ascorbate and Acetaminophen on Glucose Detection by a Needle-Type Glucose Sensor", *Biosensors & Bioelectronics*, vol. 7, 1992, pp. 345-352.
Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.
Olievier, C. N., et al., "In Vivo Measurement of Carbon Dioxide Tension with a Miniature Electrodes", *Pflugers Archiv: European Journal of Physiology*, vol. 373, 1978, pp. 269-272.
Pickup, J., "Developing Glucose Sensors for In Vivo Use", *Tibtech*, vol. 11, 1993, pp. 285-291.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pickup, J., et al., "Potentially-Implantable, Amperometric Glucose Sensors with Mediated Electron Transfer: Improving the Operating Stability", *Biosensors*, vol. 4, 1989, pp. 109-119.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.
Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.
Poitout, V., et al., "In Vitro and In Vivo Evaluation in Dogs of a Miniaturized Glucose Sensor", *ASAIO Transactions*, vol. 37, No. 3, 1991, pp. M298-M300.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

(56) References Cited

OTHER PUBLICATIONS

Salehi, C., et al., "A Telemetry-Instrumentation System for Long-Term Implantable Glucose and Oxygen Sensors", *Analytical Letters*, vol. 29, No. 13, 1996, pp. 2289-2308.
Scheller, F., et al., "Enzyme Electrodes and Their Application", *Philosophical Transactions of the Royal Society of London B*, vol. 316, 1987, pp. 85-94.
Schmidt, F. J., et al., "Calibration of a Wearable Glucose Sensor", *The International Journal of Artificial Organs*, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurementsof Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "In Vitro and In Vivo Stability of Electrode Potentials in Needle-Type Glucose Sensors", *Diabetes*, vol. 38, No. 2, 1989, pp. 164-171.
Velho, G., et al., "Strategies for Calibrating a Subcutaneous Glucose Sensor", *Biomedica & Biochimica Acta*, vol. 48, 1989, pp. 957-964.
Von Woedtke, T., et al., "In Situ Calibration of Implanted Electrochemical Glucose Sensors", *Biomedica Biochimica Acta*, vol. 48, 1989, pp. 943-952.
Wilson, G. S., et al., "Progress Toward the Development of an Implantable Sensor for Glucose", *Clinical Chemistry*, vol. 38, No. 9, 1992, pp. 1613-1617.
Ye, L., et al., "High Current Density 'Wired' Quinoprotein Glucose Dehydrogenase Electrode", *Analytical Chemistry*, vol. 65, No. 3, 1993, pp. 238-241.
PCT Application No. PCT/US2010/022860, International Search Report and Written Opinion of the International Searching Authority mailed Mar. 23, 2010.
PCT Application No. PCT/US2010/047381, International Search Report and Written Opinion of the International Searching Authority mailed Oct. 15, 2010.
PCT Application No. PCT/US2010/050772, International Search Report and Written Opinion of the International Searching Authority mailed Dec. 3, 2010.
PCT Application No. PCT/US2010/050888, International Search Report and Written Opinion of the International Searching Authority mailed Nov. 29, 2010.
PCT Application No. PCT/US2010/051861, International Search Report and Written Opinion of the International Searching Authority mailed Nov. 30, 2010.
PCT Application No. PCT/US2011/029881, International Search Report and Written Opinion of the International Searching Authority mailed May 20, 2011.
PCT Application No. PCT/US2011/029883, International Search Report and Written Opinion of the International Searching Authority mailed Jun. 2, 2011.
PCT Application No. PCT/US2011/029884, International Search Report and Written Opinion of the International Searching Authority mailed Jun. 1, 2011.
Reexamination U.S. Appl. No. 90/008,172, Request for Reexamination of U.S. Patent No. 6,990,366, filed Aug. 16, 2006.
Reexamination U.S. Appl. No. 90/008,457, Notice of Intent to Issue Reexamination Certificate mailed Mar. 13, 2008.
Reexamination U.S. Appl. No. 90/008,457, Order Granting Request for Reexamination mailed Feb. 23, 2007.
Reexamination U.S. Appl. No. 90/008,457, Request for Reexamination of U.S. Patent No. 6,990,366 filed Jan. 23, 2007.
Reexamination U.S. Appl. Nos. 90/009,104 & 90/009,328, Notice of Intent to Issue Reexamination Certificate mailed Nov. 20, 2009.
Reexamination U.S. Appl. Nos. 90/009,104 & 90/009,328, Office Action mailed Aug. 4, 2009.
Reexamination U.S. Appl. No. 90/009,104 & 90/009,328, Office Action mailed Sep. 30, 2009.
Reexamination U.S. Appl. No. 90/009,104, Office Action mailed Oct. 16, 2008.
Reexamination U.S. Appl. No. 90/009,104, Order Granting Request for Reexamination mailed Jun. 5, 2008.
Reexamination U.S. Appl. No. 90/009,104, Request for Reexamination of U.S. Patent No. 6,990,366 filed Apr. 8, 2008.
Reexamination U.S. Appl. No. 90/009,328, Order Granting Request for Reexamination mailed Dec. 9, 2008.
Reexamination U.S. Appl. No. 90/009,328, Request for Reexamination of U.S. Patent No. 6,990,366 filed Nov. 10, 2008.
Reexamination U.S. Appl. No. 90/010,791, Notice of Intent to Issue Reexamination Certificate mailed May 17, 2011.
Reexamination U.S. Appl. No. 90/010,791, Office Action mailed Dec. 17, 2010.
Reexamination U.S. Appl. No. 90/010,791, Office Action mailed May 28, 2010.
Reexamination U.S. Appl. No. 90/010,791, Order Granting Request for Reexamination mailed Feb. 22, 2010.
Reexamination U.S. Appl. No. 90/010,791, Request for Reexamination of U.S. Patent No. 6,990,366 filed Dec. 22, 2009.
Reexamination U.S. Appl. No. 90/011,730, Notice of Intent to Issue Reexam Certificate for U.S. Patent No. 6,990,366 mailed Apr. 5, 2012.
Reexamination U.S. Appl. No. 90/011,730, Office Action mailed Jan. 11, 2012.
Reexamination U.S. Appl. No. 90/011,730, Order Granting Request for Reexamination of U.S. Patent No. 6,990,366 mailed Aug. 24, 2011.
Reexamination U.S. Appl. No. 90/011,730, Request for Reexamination of U.S. Patent No. 6,990,366 filed Jun. 3, 2011.
PCT Application No. PCT/US2011/029883, International Preliminary Report on Patentability and Written Opinion of the International Searching Authority mailed Oct. 4, 2012.
U.S. Appl. No. 13/071,487, Advisory Action mailed Aug. 6, 2013.
U.S. Appl. No. 13/071,487, Office Action mailed Feb. 5, 2013.
U.S. Appl. No. 13/071,487, Office Action mailed May 30, 2013.
Gunasingham, et al., "Electrochemically Modulated Optrode for Glucose", *Biosensors & Bioelectronics*, vol. 7, 1992, pp. 353-359.

(56) References Cited

OTHER PUBLICATIONS

Ikeda, T., et al., "Artificul Pancreas—Investigation of the Stability of Glucose Sensors Using a Telemetry System" (English langauge tranlsation of abstract), *Jpn. J. Artif. Organs*, vol. 19, No. 2, 1990, 889-892.

MINIMED Technologies, "Tape Tips and Other Infusion Site Information", 1995.

European Patent Application No. EP 10739015.5, Extended European Search Report mailed May 10, 2013.

PCT Application No. PCT/US2010/022860, International Preliminary Report on Patentability and Written Opinion of the International Searching Authority mailed Aug. 18, 2011.

PCT Application No. PCT/US2010/047381, International Preliminary Report on Patentability and Written Opinion of the International Searching Authority mailed Mar. 15, 2012.

PCT Application No. PCT/US2010/050772, International Preliminary Report on Patentability and Written Opinion of the International Searching Authority mailed Apr. 12, 2012.

PCT Application No. PCT/US2010/050888, International Preliminary Report on Patentability and Written Opinion of the International Searching Authority mailed Apr. 12, 2012.

PCT Application No. PCT/US2010/051861, International Preliminary Report on Patentability and Written Opinion of the International Searching Authority mailed Apr. 19, 2012.

PCT Application No. PCT/US2011/029881, International Preliminary Report on Patentability and Written Opinion of the International Searching Authority mailed Oct. 4, 2012.

PCT Application No. PCT/US2011/029884, International Preliminary Report on Patentability and Written Opinion of the International Searching Authority mailed Oct. 4, 2012.

PCT Application No. PCT/US2012/062551, International Search Report and Written Opinion of the International Searching Authority mailed Jan. 2, 2013.

U.S. Appl. No. 12/873,133, Office Action mailed Feb. 25, 2013.

U.S. Appl. No. 12/900,363, Office Action mailed Jun. 21, 2013.

U.S. Appl. No. 12/900,363, Office Action mailed Mar. 11, 2013.

U.S. Appl. No. 13/071,497, Office Action mailed May 10, 2013.

Reexamination U.S. Appl. No. 95/002,113, Order Denying Request for Reexamination of U.S. Patent No. 6,990,366 mailed Nov. 13, 2012.

Reexamination U.S. Appl. No. 95/002,113, Petition for Review of the Order Denying Request Reexamination of U.S. Patent No. 6,990,366 mailed Dec. 13, 2012.

Reexamination U.S. Appl. No. 95/002,113, Request for Reexamination of U.S. Patent No. 6,990,366 filed Aug. 30, 2012.

Reexamination U.S. Appl. No. 95/002,162, Order Denying Request for Reexamination of U.S. Patent No. 8,175,673 mailed Nov. 13, 2012.

Reexamination U.S. Appl. No. 95/002,162, Petition for Review of the Order Denying Request Reexamination of U.S. Patent No. 8,175,673 mailed Dec. 13, 2012.

Reexamination U.S. Appl. No. 95/002,162, Request for Reexamination of U.S. Patent No. 8,175,673 filed Sep. 7, 2012.

\* cited by examiner

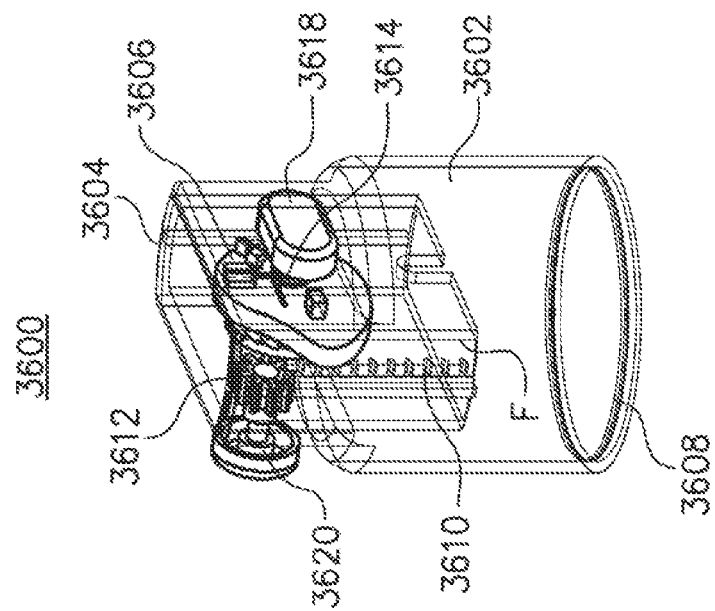
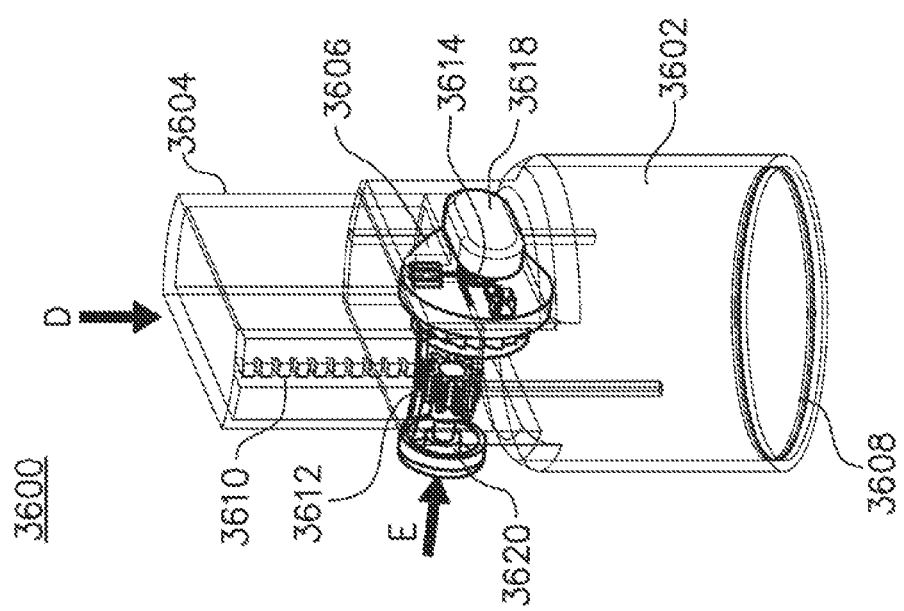

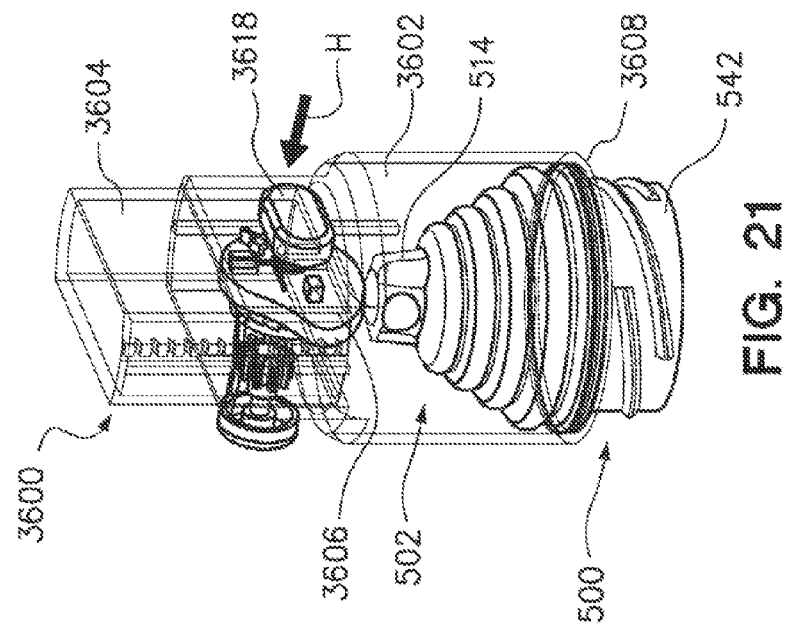
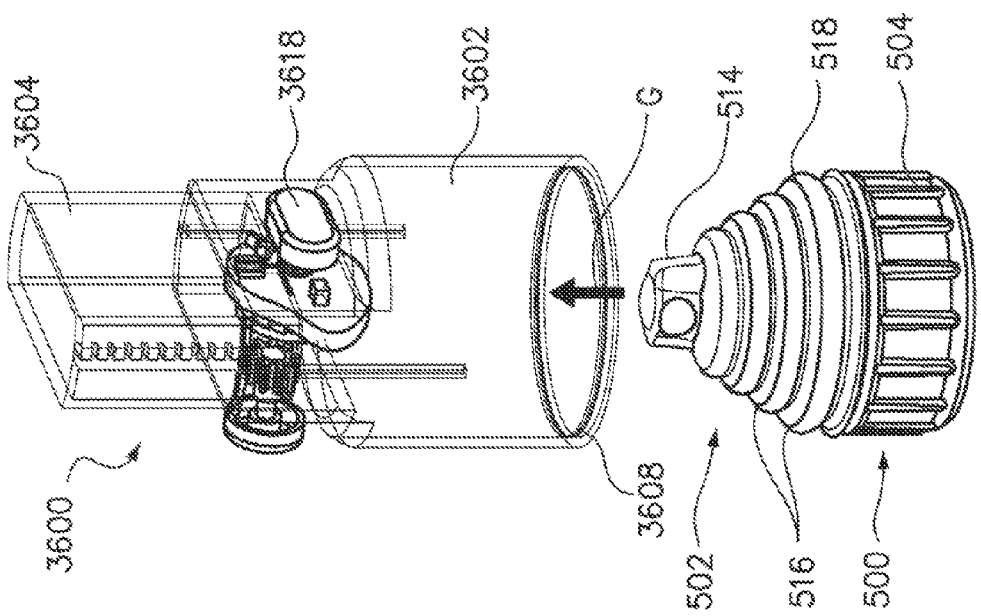

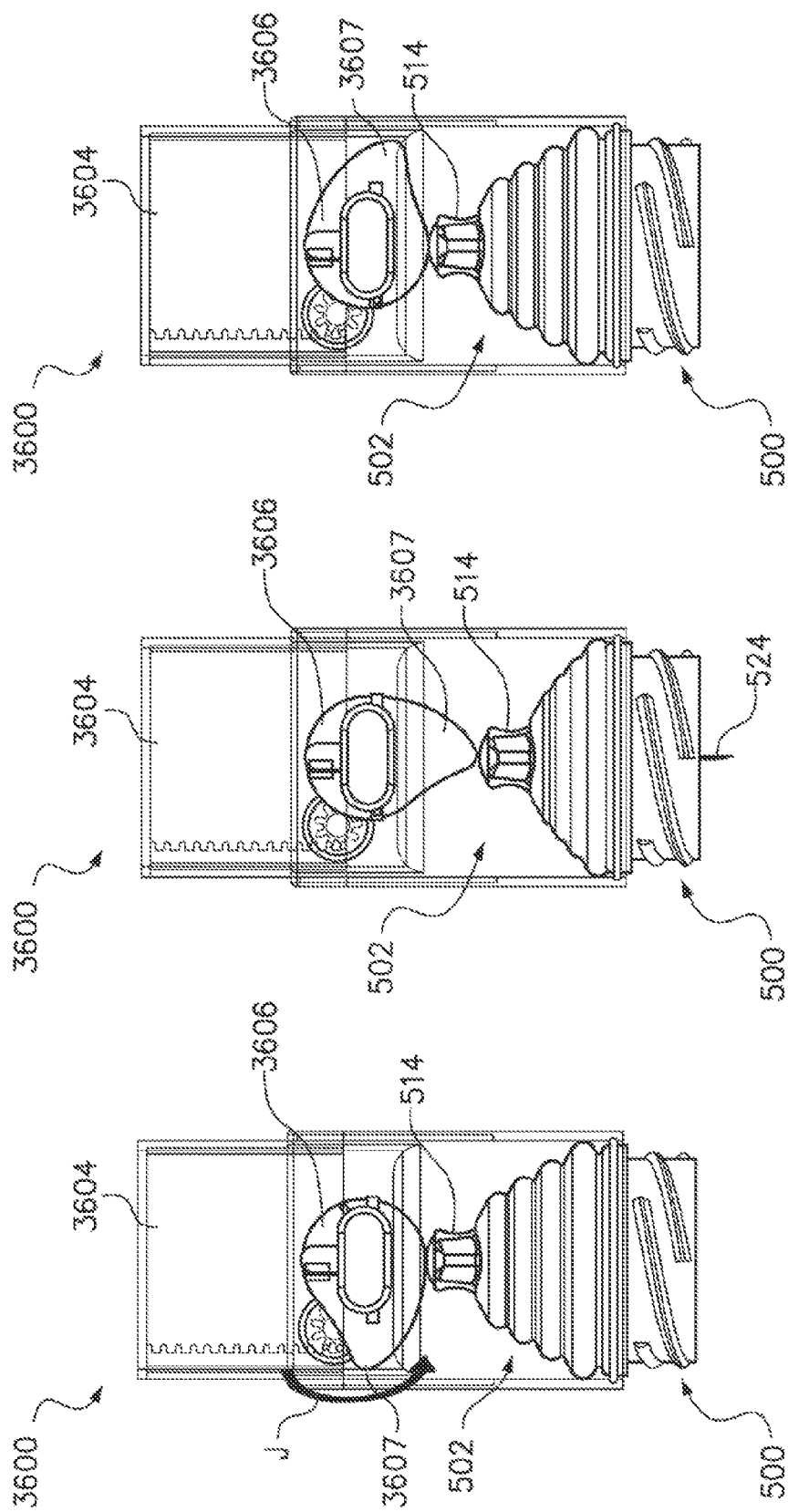

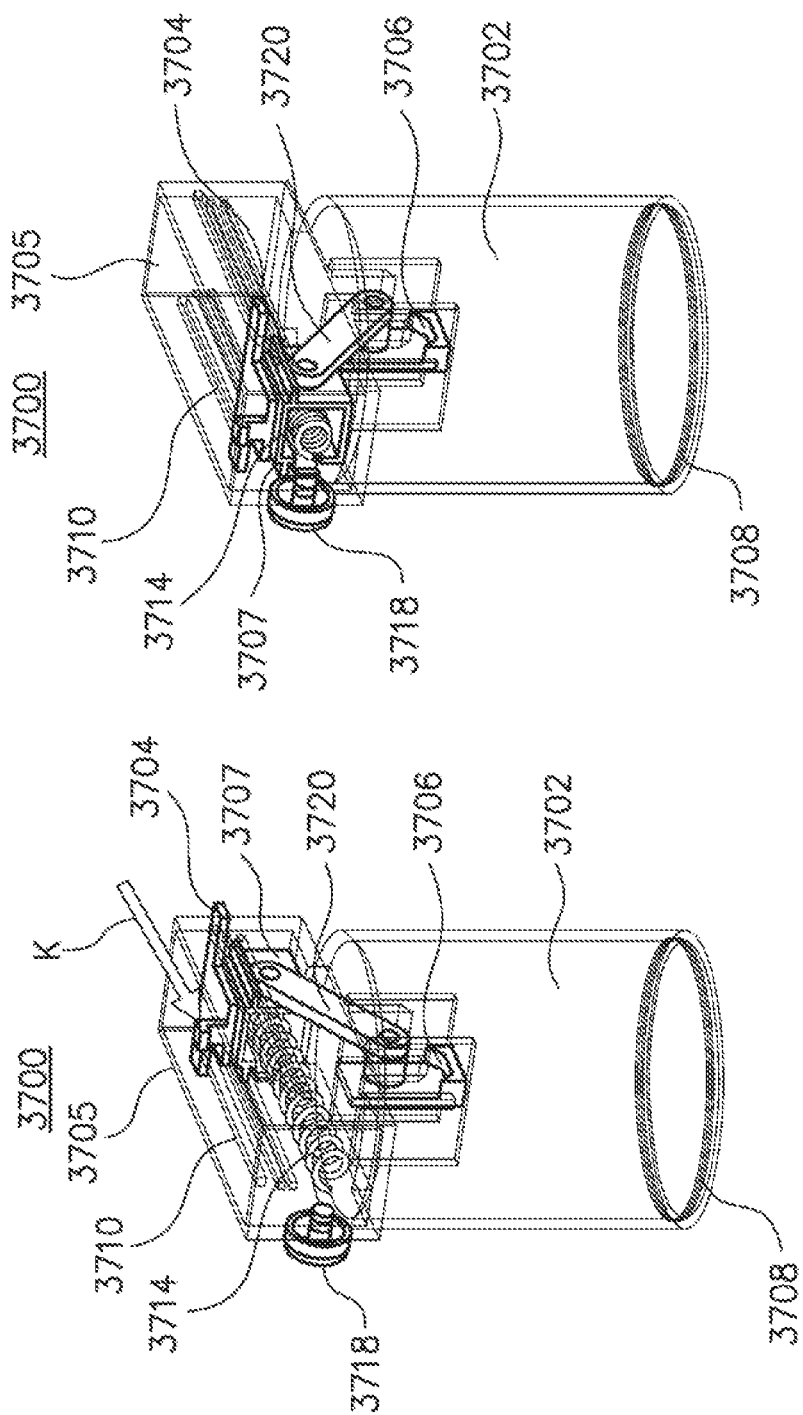

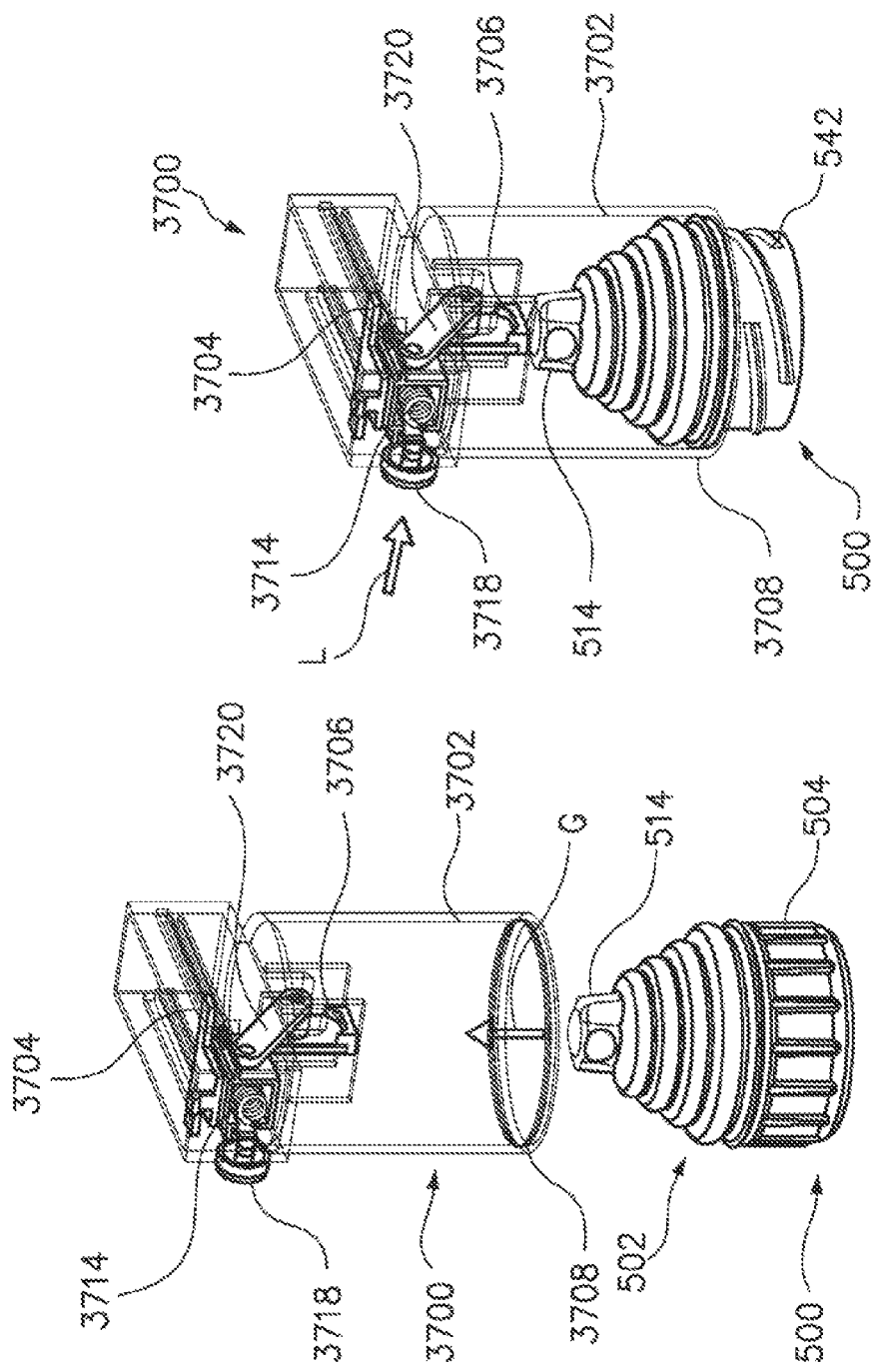

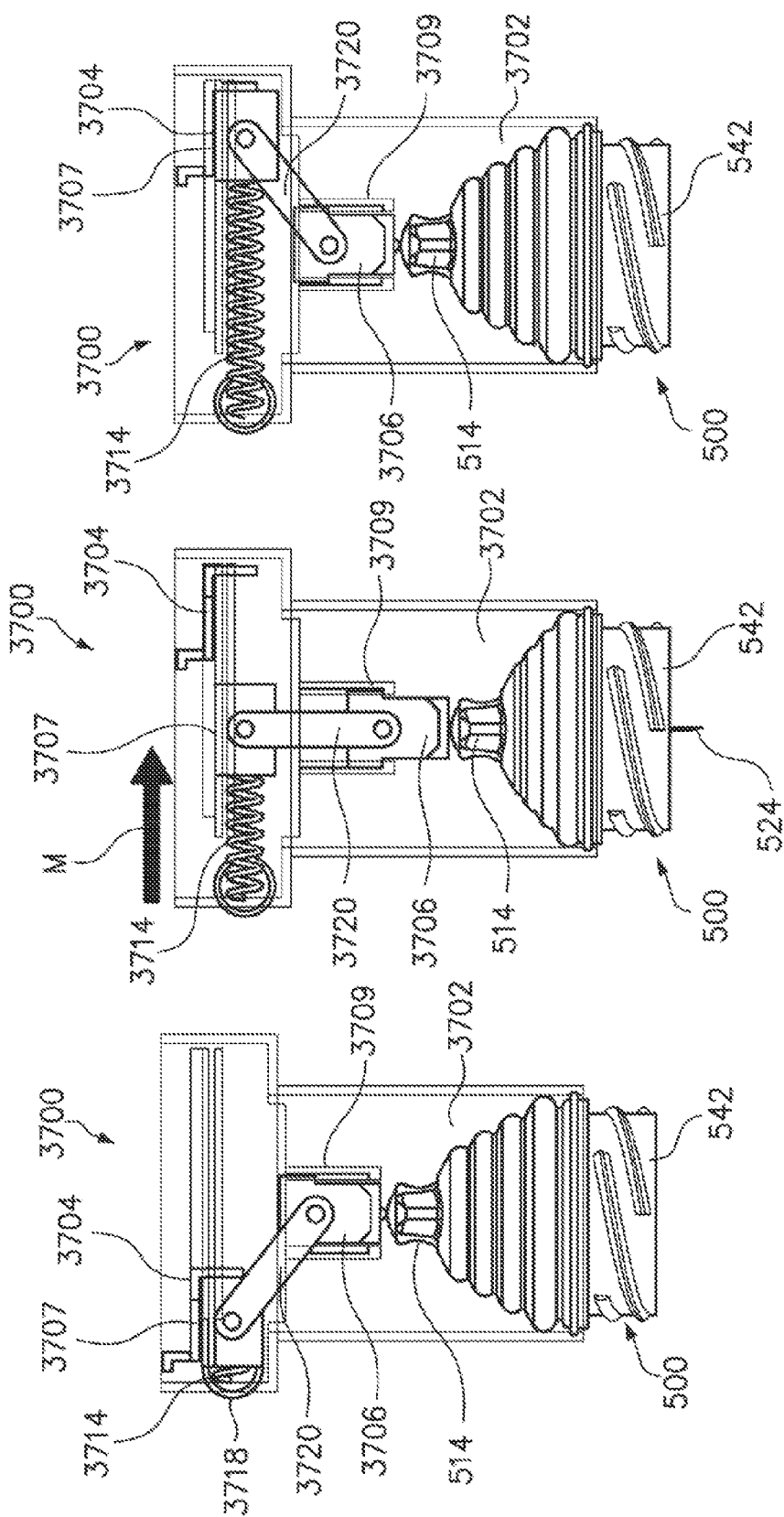

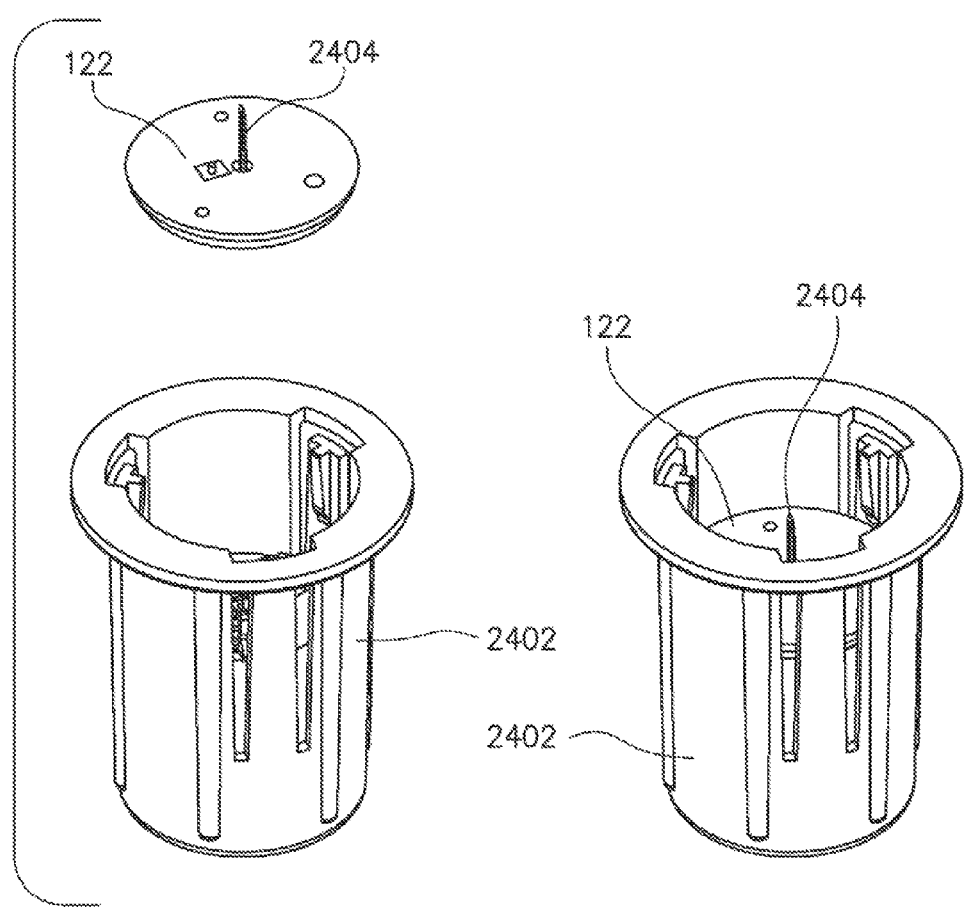
*FIG. 50*   *FIG. 51*

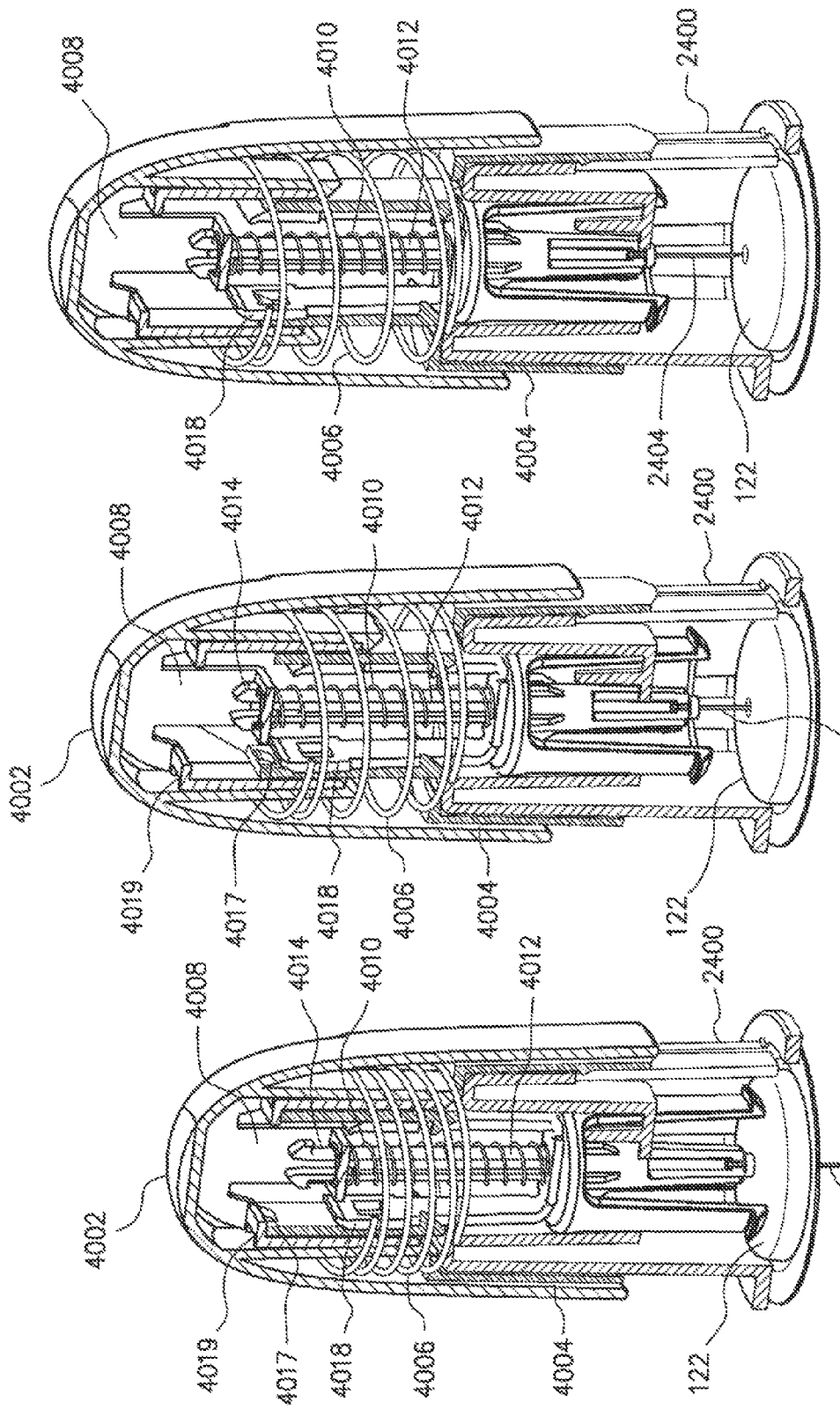

MEDICAL DEVICE INSERTERS AND PROCESSES OF INSERTING AND USING MEDICAL DEVICES

RELATED APPLICATIONS

The present application is a continuation of U.S. patent application Ser. No. 13/071,487 filed Mar. 24, 2011 entitled "Medical Device Inserters and Processes of Inserting and Using Medical Devices," which claims the benefit of U.S. Provisional Application Nos. 61/317,243, filed Mar. 24, 2010; 61/345,562, filed May 17, 2010; 61/361,374, filed Jul. 2, 2010; 61/411,262, filed Nov. 8, 2010, the disclosures of which are incorporated herein by reference for all purposes.

INCORPORATION BY REFERENCE

Patents, applications and/or publications described herein, including the following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; 7,381,184; 7,740,581; 7,811,231 U.S. Published Application Nos. 2005/0182306; 2006/0091006; 2007/0056858; 2007/0068807; 2007/0095661; 2007/0108048; 2007/0149873; 2007/0149875; 2007/0199818; 2007/0227911; 2007/0233013; 2008/0058625; 2008/0064937; 2008/0066305; 2008/0071157; 2008/0071158; 2008/0081977; 2008/0102441; 2008/0148873; 2008/0161666; 2008/0179187; 2008/0267823; 2008/0319295; 2008/0319296; 2009/0018425; 2009/0247857; 2009/0257911, 2009/0281406; 2009/0294277; 2009/0054748; 2009/0054749; 2010/0030052; 2010/0065441; 2010/0081905; 2010/0081909; 2010/0213057; 2010/0325868; 2010/0326842; 2010/0326843; 2010/0331643; 2011/0046466; U.S. patent application Ser. Nos. 12/624,767; 12/625,185; 12/625,208; 12/625,524; 12/625,525; 12/625,528; 12/628,177; 12/628,198; 12/628,201; 12/628,203; 12/628,210; 12/698,124; 12/698,129; 12/699,653; 12/699,844; 12/714,439; 12/730,193; 12/794,721; 12/807,278; 12/842,013; 12/870,818; 12/871,901; 12/873,301; 12/873,302; 13/011,897; and U.S. Provisional Application Nos. 61/238,646; 61/246,825; 61/247,516; 61/249,535; 61/317,243; 61/325,155; 61/345,562; and 61/359,265.

BACKGROUND OF THE INVENTION

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

SUMMARY

An apparatus for inserting a medical device at least partially through the skin of a subject is provided, which includes a first subassembly and a second subassembly. The first subassembly includes a sheath defining a distal surface for placement on the skin of the subject, a handle movable between a proximal position and distal position, a device support for supporting the medical device and defining an aperture therethrough, the device support coupled to the handle, a sharp support for supporting a sharp extending through said aperture and coupled to the device support, and a first driver for biasing the sharp support towards the proximal position. The second subassembly includes a housing configured for removable attachment to the first subassembly, and a second driver for advancing the sharp support towards the distal position.

In some embodiments, the first subassembly and the second subassembly are modular components. In some embodiments, the first subassembly is capable of independent operation without the second subassembly. In some embodiments, the driver of the first subassembly is capable of operation by a user without the second subassembly. In some embodiments, the driver of the first subassembly is actuable by depressing an actuation switch or button. In some embodiments, the second subassembly is configured to actuate the actuation switch or button of the first subassembly.

In some embodiments, the second driver includes a rotatable cam or a torsion spring. In some embodiments, the second driver includes either an axial driver and a crank assembly or a compression spring. In some embodiments, the first driver includes a compression spring, or a torsion spring.

In some embodiments, the handle is at least partially disposed surrounding the sheath. In some embodiments, a retention member for retaining the device support in the distal position is provided. The device support may be coupled to the handle until the device support reaches a distal position.

In some embodiments, the first subassembly is configured for a single use. In some embodiments, the second subassembly is configured for multiple uses.

Embodiments of analyte sensors are provided which include a body having a proximal section and a distal section. The distal section may be longitudinally aligned with the proximal section. An intermediate section may be included between the proximal and distal sections, and in some embodiments the intermediate section is laterally displaced from at least the distal member.

In some embodiments, the proximal end is received within a needle seat to create an anchor region to allow the sensor body to slide into an opening defined in the insertion sharp but prevent the sensor body from inadvertently slipping out of the insertion needle. In some embodiments, a width of the distal section of the sensor body is sized to fit within the opening of the insertion sharp. In certain embodiments, the opening in the sharp has a diameter of about 20 gauge to about 26 gauge, e.g., 21 gauge to about 25 gauge, where in certain embodiments the sharp is 21 gauge or 23 gauge or 25 gauge. Such sharp may be used with a sensor having a width or diameter —at least the portion that is carried by the sharp—of about 0.20 mm to about 0.80 mm, e.g., about 0.25 mm to about 0.60 mm, where in some embodiments the width or diameter of at least a portion of a sensor is 0.27 mm or 0.33 mm or 0.58 mm.

In some embodiments, the intermediate member includes a plane-altering portion. The plane-altering portion allows the proximal section of the sensor body to be in a plane different than the distal section of the sensor body. In some embodiments, the proximal section and the distal section are in planes substantially perpendicular to each other, e.g., the area may define an angle of about 120° to about 60°, e.g., about 90°.

In certain embodiments, apparatuses for inserting a medical device at least partially through the skin of a subject are provided which include a sheath defining a distal surface for placement on the skin of the subject; a handle movable between a proximal position and distal position; a device support for supporting the medical device and defining an aperture therethrough, the device support coupled to the handle; a sharp support for supporting a sharp extending through said aperture and coupled to the device support; and driver for biasing the sharp support towards the proximal position.

In some embodiments, the driver includes a compression spring. In some embodiments, the handle is at least partially disposed surrounding the sheath. In some embodiments, a stop portion for retaining the device support in the distal position is included. In some embodiments, the device support is coupled to the handle until the device support reaches a distal position. In some embodiments, the device support is uncoupled from the sharp support when the device support reaches the distal position.

In some embodiments, a second assembly interfaces with the insertion devices or first subassembly. The second assembly automates the insertion segment motion of the described inserter. The second assembly may include a housing configured for removable attachment to the first subassembly, a handle configured for longitudinal movement with respect to the housing, an actuator configured for longitudinal movement with respect to the housing, a release member either located on the actuator or handle which is actuated upon the handle reaching a predetermined position, a driver element coupled between the handle and the actuator, energized upon distal movement of the handle, which drives the actuator distally once the release member is actuated, and a second driver which is also energized upon distal movement of the handle, that applies a proximal force on the handle that returns the handle to a proximal position after pressure is relieved from the handle post insertion. The second driver, coupled through the handle, also provides a proximal force to return the actuator to its proximal position where the release member is reengaged.

In some embodiments, the first driver includes a compression spring, or a torsion spring. In some embodiments, the handle is at least partially disposed surrounding the sheath. In some embodiments, a retention member for retaining the device support in the distal position is provided. The device support may be coupled to the handle until the device support reaches a distal position.

In some embodiments, the first subassembly is configured for a single use. In some embodiments, the first subassembly is configured for multiple uses. In some embodiments, the second subassembly is configured for multiple uses.

These and other features, objects, and advantages of the disclosed subject matter will become apparent to those persons skilled in the art upon reading the detailed description as more fully described below.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 18-19 are perspective views of an inserter in accordance with another embodiment of the disclosed subject matter;

FIGS. 20-21 are perspective views of the inserter of the embodiment of FIG. 18 in combination with the inserter of FIG. 14 in accordance with another embodiment of the disclosed subject matter;

FIGS. 22-24 are side views of the inserter of the embodiment of FIG. 18 in combination with the inserter of FIG. 14 in accordance with another embodiment of the disclosed subject matter;

FIGS. 25-26 are perspective views of an inserter in accordance with another embodiment of the disclosed subject matter;

FIGS. 27-28 are perspective views of the inserter of the embodiment of FIG. 25 in combination with the inserter of FIG. 14 in accordance with another embodiment of the disclosed subject matter;

FIGS. 29-31 are side views of the inserter of the embodiment of FIG. 25 in combination with the inserter of FIG. 14 in accordance with another embodiment of the disclosed subject matter;

FIGS. 46-53 are perspective views of the inserter of FIG. 44 showing the assembly of various components in accordance with the disclosed subject matter;

FIGS. 72-79 are cross-sectional views of the inserter of FIG. 70 in accordance with the disclosed subject matter.

DETAILED DESCRIPTION OF THE EMBODIMENTS

Figure 1:
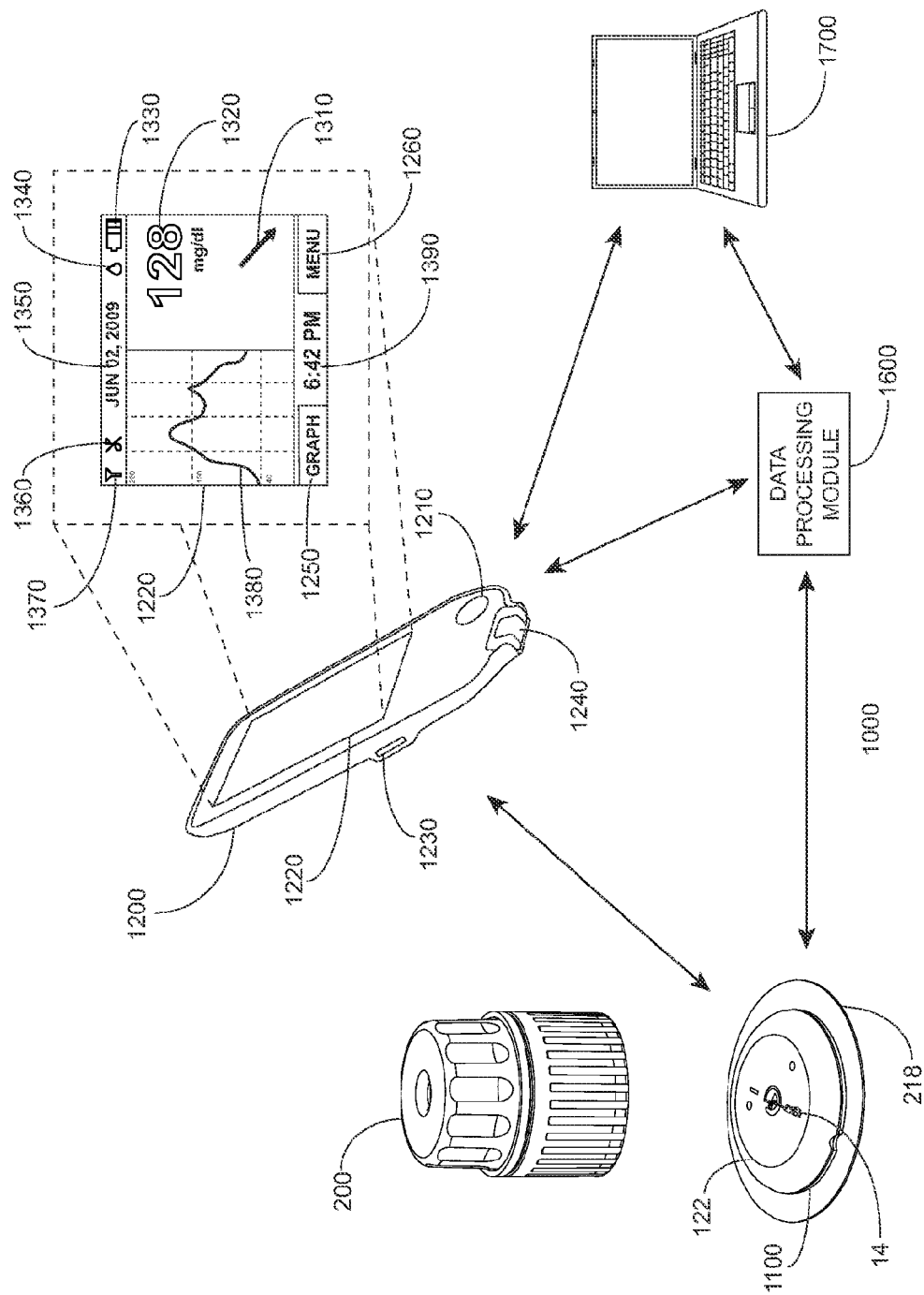
FIG. 1 illustrates an analyte monitoring system for real time analyte (e.g., glucose) measurement, data acquisition and/or processing in certain embodiments.

A detailed description of the disclosure is provided herein. It should be understood, in connection with the following description, that the subject matter is not limited to particular embodiments described, as the particular embodiments of the subject matter may, of course, vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range, and any other stated or intervening value in that stated range, is encompassed within the disclosed subject matter. Every range stated is also intended to specifically disclose each and every "subrange" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from," "to," "through," or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated by reference herein for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a," "an," and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible.

Reference to a singular item includes the possibility that there are plural of the same item present. When two or more items (for example, elements or processes) are referenced by an alternative "or," this indicates that either could be present separately or any combination of them could be present together except where the presence of one necessarily excludes the other or others.

Generally, embodiments of the present disclosure relate to an apparatus for inserting a medical device at least partially into the skin of the patient. Some embodiments relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user to process information obtained from the sensor.

In certain embodiments, analyte information is communicated from a first device such as an on body electronics unit to a second device which may include user interface features, including a display, and/or the like. Information may be communicated from the first device to the second device automatically and/or continuously when the analyte information is available, or may not be communicated automatically and/or continuously, but rather stored or logged in a memory of the first device. Accordingly, in many embodiments of the system, analyte information derived by the sensor/on body electronics (for example, on body electronics) is made available in a user-usable or viewable form only when queried by the user such that the timing of data communication is selected by the user. In some embodiments, the display of information is selected by the user, while the timing of data communication is not.

In this manner, analyte information is only provided or evident to a user (provided at a user interface device) in some embodiments when desired by the user even though an in vivo analyte sensor automatically and/or continuously monitors the analyte level in vivo, i.e., the sensor automatically monitors analyte such as glucose on a pre-defined time interval over its usage life. For example, an analyte sensor may be positioned in vivo and coupled to on body electronics for a given sensing period, e.g., about 14 days. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated and sensor-derived information is then sent from the on body electronics to the remote device or display device.

In still other embodiments, the information may be communicated from the first device to the second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments an inserter as described herein is used to place a sensor electronics assembly on the body so that at least a portion of the in vivo sensor is in contact with bodily fluid such as ISF. Once the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body electronics and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include inserters for in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc). For example, a display device communication port may enable charging a display device battery with a respective charging cable and/or data exchange between a display device and its compatible informatics software.

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc. Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

As described in detail below, embodiments include devices, systems, kits and/or methods to monitor one or more physiological parameters such as, for example, but not limited to, analyte levels, temperature levels, heart rate, or user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent application Ser. No. 12/698,129 filed on Feb. 1, 2010 and U.S. Provisional Application Nos. 61/238,646, 61/246,825, 61/247,516, 61/249,535, 61/317,243, 61/345,562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or maintained in a low power state including no power state, inactive mode, or all components may be in an inactive, powered down mode. Upon receipt of the command, the remaining portion (or all) of the components of the on body electronics is switched to active, fully operational mode.

Embodiments of on body electronics may include one or more printed circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on body electronics, but in many embodiments will be accomplished with display device electronics. In certain embodiments, glucose level is derived from the monitored analyte level in the ISF.

Analyte sensors may be insertable into a vein, artery, or other portion of the body containing analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments include analyte monitors that are provided in small, lightweight, battery-powered and electronically-controlled systems. Such systems may be configured to detect physical parameters of subjects, such as signals indicative of in vivo analyte levels using an electrochemical sensor, and collect such signals, with or without processing. Any suitable measurement technique may be used to obtain signals from the sensors, e.g., may detect current, may employ potentiometry, etc. Techniques may include, but are not limited to amperometry, coulometry, and voltammetry. In some embodiments, sensing systems may be optical, colorimetric, and the like. In some embodiments, the portion of the system that performs this initial processing may be configured to provide the raw or at least initially processed data to another unit for further collection and/or processing. Such provision of data may be affected, for example, by a wired connection, such as an electrical, or by a wireless connection, such as an IR or RF connection.

In certain systems, the analyte sensor is in communication with on body electronics. The on-body unit may include a housing in which the on body electronics and at least a portion of the sensor are received.

Certain embodiments are modular. The on-body unit may be separately provided as a physically distinct assembly from a monitor unit, e.g., which displays or otherwise indicates analyte levels to a user. The on-body unit may be configured to provide the analyte levels detected by the sensor and/or other information (such as temperature, sensor life, etc.) over a communication link to the monitor unit. The monitor unit, in some embodiments, may include, e.g., a mobile telephone device, an in vitro glucose meter, a personal digital assistant, or other consumer electronics such as MP3 device, camera, radio, personal computer, etc., or other communication-enabled data-processing device.

The display unit may perform a variety of functions such as but not limited to data storage and/or processing and/or analysis and/or communication, etc., on the received analyte data to generate information pertaining to the monitored analyte levels and/or process the other information. The monitor unit may incorporate a display screen, which can be used, for example, to display measured analyte levels, and/or an audio component such as a speaker to audibly provide information to a user, and/or a vibration device to provide tactile feedback to a user. It is also useful for a user of an analyte-monitoring system to be able to see trend indications (including the magnitude and direction of any ongoing trend, e.g., the rate of change of an analyte or other parameter, and the amount of time a subject is above and/or below a threshold, such as a hypoglycemic and/or hyperglycemic threshold, etc.); such data may be displayed either numerically, or by a visual indicator such as an arrow that may vary in visual attributes, like size, shape, color, animation, or direction. The monitor unit may further be adapted to receive information from or about an in vitro analyte test strip, which may be manually or automatically entered into the monitor unit. In some embodiments a monitor unit may incorporate an in vitro analyte test strip port and related electronics in order to be able to make discrete (e.g., blood glucose) measurements using an in vitro test strip (see, e.g., U.S. Pat. No. 6,175,752, the disclosure of which is incorporated by reference herein for all purposes).

The modularity of these systems may vary where one or more components may be constructed to be single use and one or more may be constructed to be re-useable. In some embodiments the sensor is designed to be attachable and detachable from the on body electronics (and the on-body unit may be reusable), e.g., so that one or more of the components may be reused one or more times, while in other embodiments, the sensor and on body electronics may be provided as an integrated, undetachable package, which may be designed to be disposable after use, i.e., not re-used.

Embodiments of In Vivo Monitoring Systems

For purpose of illustration, and not limitation, the inserters described herein may be used in connection with an exemplary analyte monitoring system as depicted in FIG. 1. It is understood that the inserters described herein may be used with any medical device on its own or in connection with a system. FIG. 1 shows an exemplary in vivo-based analyte monitoring system 1000 in accordance with embodiments of the present disclosure. As shown, in certain embodiments, analyte monitoring system 1000 includes on body electronics 1100 electrically coupled to in vivo analyte sensor 14 (a proximal portion of which is shown in FIG. 1), and attached to adhesive layer 218 for attachment on a skin surface on the body of a user. On body electronics 1100 includes on body housing 122 that defines an interior compartment.

Also shown in FIG. 1 is insertion device 200 (or insertion devices 300, 400, 2400, 2500, 2700, 3700 described herein) that, when operated, transcutaneously positions a portion of analyte sensor 14 through a skin surface and in fluid contact with ISF, and positions on body electronics 1100 and adhesive layer 218 on a skin surface, as will be described in greater detail herein. In certain embodiments, on body electronics 1100, analyte sensor 14 and adhesive layer 218 are sealed within the housing of insertion device 200 before use, and in certain embodiments, adhesive layer 218 is also sealed within the housing or the adhesive layer can provide a seal for preserving the sterility of the apparatus. Additional details regarding insertion devices are discussed, e.g., in U.S. patent application Ser. No. 12/698,129 and U.S. Provisional Application Nos. 61/238,646, 61/246,825, 61/247,516, 61/249,535, and 61/345,562, the disclosures of each of which are incorporated herein by reference for all purposes.

Referring back to the FIG. 1, analyte monitoring system 1000 includes display device 1200 which includes a display 1220 to output information to the user, an input component 1210 such as a button, actuator, a touch sensitive switch, a capacitive switch, pressure sensitive switch, jog wheel or the like, to input data or command to display device 1200 or otherwise control the operation of display device 1200. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 1100 may be configured to store some or all of the monitored analyte related data received from analyte sensor 14 in a memory during the monitoring time period, and maintain it in memory until the usage period ends. In such embodiments, stored data is retrieved from on body electronics 1100 at the conclusion of the monitoring time period, for example, after removing analyte sensor 14 from the user by detaching on body electronics 1100 from the skin surface where it was positioned during the monitoring time period. In such data logging configurations, real time monitored analyte level is not communicated to display device 1200 during the monitoring period or otherwise transmitted from on body electronics 1100, but rather, retrieved from on body electronics 1100 after the monitoring time period.

In certain embodiments, input component 1210 of display device 1200 may include a microphone and display device 1200 may include software configured to analyze audio input received from the microphone, such that functions and operation of the display device 1200 may be controlled by voice commands. In certain embodiments, an output component of display device 1200 includes a speaker for outputting information as audible signals. Similar voice responsive components such as a speaker, microphone and software routines to generate, process and store voice driven signals may be provided to on body electronics 1100.

In certain embodiments, display 1220 and input component 1210 may be integrated into a single component, for example a display that can detect the presence and location of a physical contact touch upon the display such as a touch screen user interface. In such embodiments, the user may control the operation of display device 1200 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 1200 also includes data communication port 1230 for wired data communication with external devices such as remote terminal (personal computer) 1700, for example. Example embodiments of the data communication port 1230 include USB port, mini USB port, RS-232 port, Ethernet port, Firewire port, or other similar data communication ports configured to connect to the compatible data cables. Display device 1200 may also include an integrated in vitro glucose meter, including in vitro test strip port 1240 to receive an in vitro glucose test strip for performing in vitro blood glucose measurements.

Referring still to FIG. 1, display 1220 in certain embodiments is configured to display a variety of information— some or all of which may be displayed at the same or different time on display 1220. In certain embodiments the displayed information is user-selectable so that a user can customize the information shown on a given display screen. Display 1220 may include but is not limited to graphical display 1380, for example, providing a graphical output of glucose values over a monitored time period (which may show important markers such as meals, exercise, sleep, heart rate, blood pressure, etc, numerical display 1320, for example, providing monitored glucose values (acquired or received in response to the request for the information), and trend or directional arrow display 1310 that indicates a rate of analyte change and/or a rate of the rate of analyte change, e.g., by moving locations on display 1220.

As further shown in FIG. 1, display 1220 may also include date display 1350 providing for example, date information for the user, time of day information display 1390 providing time of day information to the user, battery level indicator display 1330 which graphically shows the condition of the battery (rechargeable or disposable) of the display device 1200, sensor calibration status icon display 1340 for example, in monitoring systems that require periodic, routine or a predetermined number of user calibration events, notifying the user that the analyte sensor calibration is necessary, audio/vibratory settings icon display 1360 for displaying the status of the audio/vibratory output or alarm state, and wireless connectivity status icon display 1370 that provides indication of wireless communication connection with other devices such as on body electronics, data processing module 1600, and/or remote terminal 1700. As additionally shown in FIG. 1, display 1220 may further include simulated touch screen button 1250, 1260 for accessing menus, changing display graph output configurations or otherwise for controlling the operation of display device 1200.

Referring back to FIG. 1, in certain embodiments, display 1220 of display device 1200 may be additionally, or instead of visual display, configured to output alarms notifications such as alarm and/or alert notifications, glucose values etc, which may be audible, tactile, or any combination thereof. In one aspect, the display device 1200 may include other output components such as a speaker, vibratory output component and the like to provide audible and/or vibratory output indication to the user in addition to the visual output indication provided on display 1220. Further details and other display embodiments can be found in, e.g., U.S. patent application Ser. No. 12/871,901, U.S. provisional application Nos. 61/238,672, 61/247,541, 61/297,625, the disclosures of each of which are incorporated herein by reference for all purposes.

After the positioning of on body electronics 1100 on the skin surface and analyte sensor 14 in vivo to establish fluid contact with ISF (or other appropriate body fluid), on body electronics 1100 in certain embodiments is configured to wirelessly communicate analyte related data (such as, for example, data corresponding to monitored analyte level and/or monitored temperature data, and/or stored historical analyte related data) when on body electronics 1100 receives a command or request signal from display device 1200. In certain embodiments, on body electronics 1100 may be configured to at least periodically broadcast real time data associated with monitored analyte level which is received by display device 1200 when display device 1200 is within communication range of the data broadcast from on body electronics 1100, i.e., it does not need a command or request from a display device to send information.

For example, display device 1200 may be configured to transmit one or more commands to on body electronics 1100 to initiate data transfer, and in response, on body electronics 1100 may be configured to wirelessly transmit stored analyte related data collected during the monitoring time period to display device 1200. Display device 1200 may in turn be connected to a remote terminal 1700 such as a personal computer and functions as a data conduit to transfer the stored analyte level information from the on body electronics 1100 to remote terminal 1700. In certain embodiments, the received data from the on body electronics 1100 may be stored (permanently or temporarily) in one or more memory of the display device 1200. In certain other embodiments, display device 1200 is configured as a data conduit to pass the data received from on body electronics 1100 to remote terminal 1700 that is connected to display device 1200.

Referring still to FIG. 1, also shown in analyte monitoring system 1000 are data processing module 1600 and remote terminal 1700. Remote terminal 1700 may include a personal computer, a server terminal a laptop computer or other suitable data processing devices including software for data management and analysis and communication with the components in the analyte monitoring system 1000. For example, remote terminal 1700 may be connected to a local area network (LAN), a wide area network (WAN), or other data network for uni-directional or bi-directional data communication between remote terminal 1700 and display device 1200 and/or data processing module 1600.

Remote terminal 1700 in certain embodiments may include one or more computer terminals located at a physician's office or a hospital. For example, remote terminal 1700 may be located at a location other than the location of display device 1200. Remote terminal 1700 and display device 1200 could be in different rooms or different buildings. Remote terminal 1700 and display device 1200 could be at least about one mile apart, e.g., at least about 100 miles apart, e.g., at least about 1000 miles apart. For example, remote terminal 1700 could be in the same city as display device 1200, remote terminal 1700 could be in a different city than display device 1200, remote terminal 1700 could be in the same state as display device 1200, remote terminal 1700 could be in a different state than display device 1200, remote terminal 1700 could be in the same country as display device 1200, or remote terminal 1700 could be in a different country than display device 1200, for example.

In certain embodiments, a separate, optional data communication/processing device such as data processing module 1600 may be provided in analyte monitoring system 1000. Data processing module 1600 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 1600 may further include communication ports, drivers or connectors to establish wired communication with one or more of display device 1200, on body electronics 1100, or remote terminal 1700 including, for example, but not limited to USB connector and/or USB port, Ethernet connector and/or port, FireWire connector and/or port, or RS-232 port and/or connector.

In certain embodiments, data processing module 1600 is programmed to transmit a polling or query signal to on body electronics 1100 at a predetermined time interval (e.g., once every minute, once every five minutes, or the like), and in response, receive the monitored analyte level information from on body electronics 1100. Data processing module 1600 stores in its memory the received analyte level information, and/or relays or retransmits the received information to another device such as display device 1200. More specifically in certain embodiments, data processing module 1600 may be configured as a data relay device to retransmit or pass through the received analyte level data from on body electronics 1100 to display device 1200 or a remote terminal (for example, over a data network such as a cellular or WiFi data network) or both.

In certain embodiments, on body electronics 1100 and data processing module 1600 may be positioned on the skin surface of the user within a predetermined distance of each other (for example, about 1-12 inches, or about 1-10 inches, or about 1-7 inches, or about 1-5 inches) such that periodic communication between on body electronics 1100 and data processing module 1600 is maintained. Alternatively, data processing module 1600 may be worn on a belt or clothing item of the user, such that the desired distance for communication between the on body electronics 1100 and data processing module 1600 for data communication is maintained. In a further aspect, the housing of data processing module 1600 may be configured to couple to or engage with on body electronics 1100 such that the two devices are combined or integrated as a single assembly and positioned on the skin surface. In further embodiments, data processing module 1600 is detachably engaged or connected to on body electronics 1100 providing additional modularity such that data processing module 1600 may be optionally removed or reattached as desired.

Referring again to FIG. 1, in certain embodiments, data processing module 1600 is programmed to transmit a command or signal to on body electronics 1100 at a predetermined time interval such as once every minute, or once every 5 minutes or once every 30 minutes or any other suitable or desired programmable time interval to request analyte related data from on body electronics 1100. When data processing module 1600 receives the requested analyte related data, it stores the received data. In this manner, analyte monitoring system 1000 may be configured to receive the continuously monitored analyte related information at the programmed or programmable time interval, which is stored and/or displayed to the user. The stored data in data processing module 1600 may be subsequently provided or transmitted to display device 1200, remote terminal 1700 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 1600 transmits a command or signal to on body electronics 1100 to receive the analyte related data in response to a user activation of a switch provided on data processing module 1600 or a user initiated command received from display device 1200. In further embodiments, data processing module 1600 is configured to transmit a command or signal to on body electronics 1100 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 1600 may be programmed to automatically transmit a request command or signal to on body electronics 1100. Alternatively, data processing module 1600 may be programmed to activate an alarm to notify the user that a predetermined time period of time has elapsed since the last communication between the data processing module 1600 and on body electronics 1100. In this manner, users or healthcare providers may program or configure data processing module 1600 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 14 that is outside a predetermined acceptable range indicating a physiological condition) which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 1100 and output to the user on a user interface of on body electronics 1100 so that corrective action may be timely taken. In addition to or alternatively, if display device 1200 is within communication range, the output indications or alarm data may be communicated to display device 1200 whose processor, upon detection of the alarm data reception, controls the display 1220 to output one or more notification.

In certain embodiments, control logic or microprocessors of on body electronics 1100 include software programs to determine future or anticipated analyte levels based on information obtained from analyte sensor 14, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 1200, or the on body electronics 1100, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 1200, data processing module 1600, and/or remote terminal 1700, and/or on body electronics 1100. Such information may be displayed as, for example, a graph (such as a line graph) to indicate to the user the current and/or historical and/or predicted future analyte levels as measured and predicted by the analyte monitoring system 1000. Such information may also be displayed as directional arrows (for example, see trend or directional arrow display 1310) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 1000 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 1600 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 1100, remote terminal 1700 or display device 1200. In a further aspect, software algorithms for execution by data processing module 1600 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 1700 may be configured to provide the executable application software to the one or more of the communication devices described above when communication between the remote terminal 1700 and the devices are established.

In still further embodiments, executable software applications may be provided over-the-air (OTA) as an OTA download such that wired connection to remote terminal 1700 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 1600 and/or display device 1200.

Referring back to remote terminal 1700 of FIG. 1, in certain embodiments, new software and/or software updates such as software patches or fixes, firmware updates or software driver upgrades, among others, for display device 1200 and/or on body electronics 1100 and/or data processing module 1600 may be provided by remote terminal 1700 when communication between the remote terminal 1700 and display device 1200 and/or data processing module 1600 is established. For example, software upgrades, executable programming changes or modification for on body electronics 1100 may be received from remote terminal 1700 by one or more of display device 1200 or data processing module 1600, and thereafter, provided to on body electronics 1100 to update its software or programmable functions. For example, in certain embodiments, software received and installed in on body electronics 1100 may include software bug fixes, modification to the previously stalled software parameters (modification to analyte related data storage time interval, resetting or adjusting time base or information of on body electronics 1100, modification to the transmitted data type, data transmission sequence, or data storage time period, among others). Additional details describing field upgradability of software of portable electronic devices, and data processing are provided in U.S. application Ser. Nos. 12/698,124, 12/794,721, now U.S. Pat. No. 8,595,607, Ser. Nos. 12/699,653, and 12/699,844, and U.S. Provisional Application Nos. 61/359,265 and 61/325,155 the disclosures of which are incorporated by reference herein for all purposes.

The Sensor

The analyte sensor 14 of the analyte measurement system 1000 may be used to monitor levels of a wide variety of analytes. Analytes that may be monitored include, for example, acetylcholine, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid-stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. One or more analyte may be monitored by a given sensor. In those embodiments that monitor more than one analyte, the analytes may be monitored at the same or different times, which may use the same on body electronics (e.g., simultaneously) or with different on body electronics.

In one embodiment of the present disclosure, sensor 14 is physically positioned in or on the body of a user whose analyte level is being monitored. Sensor 14 may be configured to continuously sample the analyte level of the user and convert the sampled analyte level, e.g., glucose concentration into a corresponding data signal, e.g., a current or voltage, for input into on body electronics. Alternatively, sensor 14 may be configured to sample analyte levels on demand. The on body electronics may amplify, filter, average, and/or otherwise process signal provided by the sensor.

Figure 2:
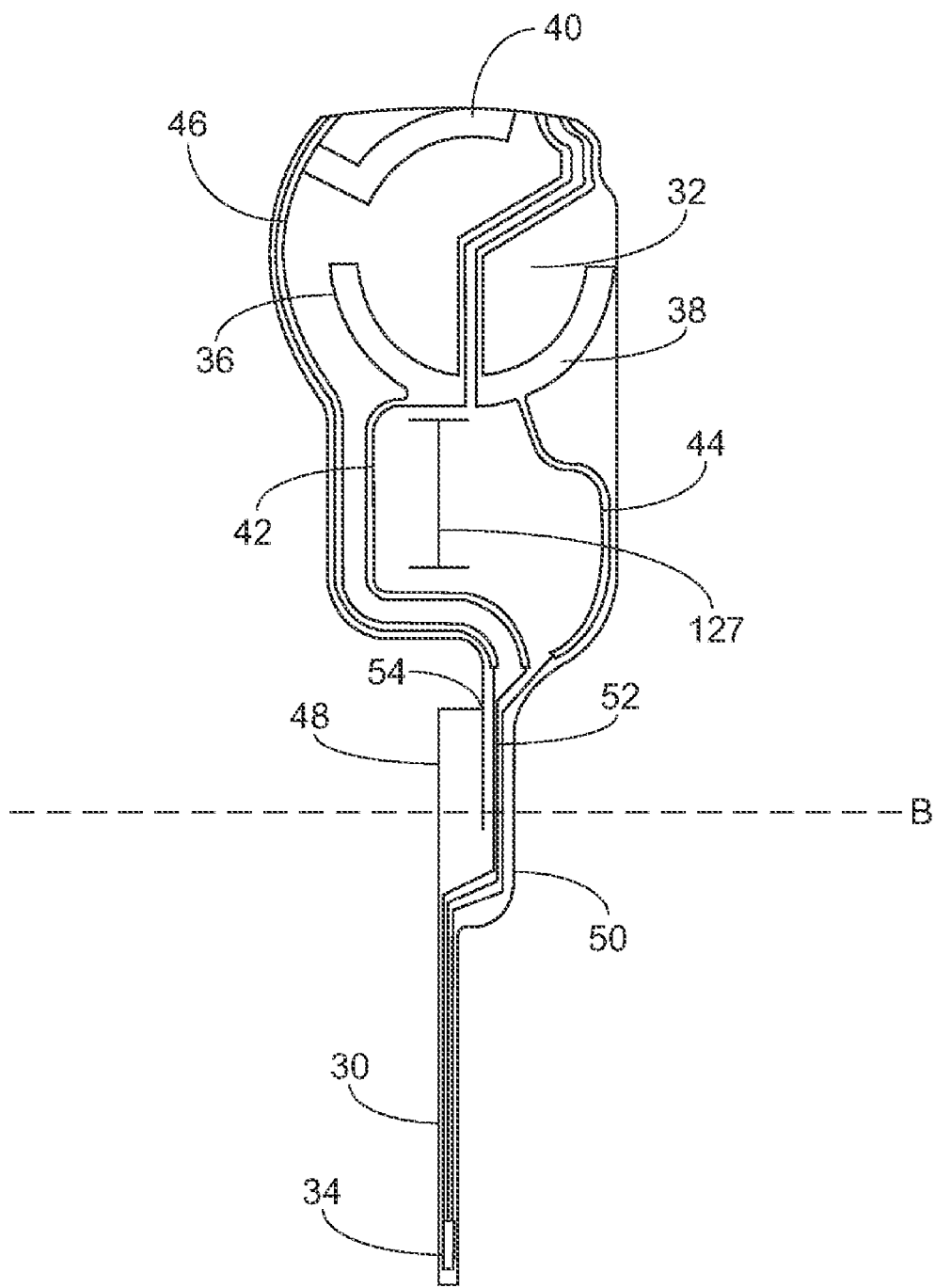
FIGS. 2-3 are views of an electrochemical sensor in accordance with a further embodiment of the disclosed subject matter.

An embodiment of the sensor 14 is illustrated in FIG. 2. It is understood that the inserters described herein can be used with other medical devices. The shape(s) described herein are exemplary only. Other sensor shapes are contemplated. In some embodiments, sensor 14 includes a substrate which is a dielectric, e.g., a polymer or plastic material, such as polyester or polyamide. In this embodiment, the sensor is constructed so that a portion is positionable beneath skin and a portion is above skin. Accordingly, sensor 14 includes an insertion or internal portion 30 and an external or electrical contact portion 32. In some embodiments, the contact portion 32 includes several conductive contacts 36, 38, and 40 (herein shown as three contacts) for connection to other electronics, e.g., at the on body electronics 1100. (See FIG. 1.) The contacts provided in this embodiment are for a working electrode, a reference electrode, and a counter electrode. In some embodiments, two or more working electrodes are provided. The operative portions of these electrodes, that is, working electrode, reference electrode, and counter electrode (not individually shown), are provided at the insertion portion, e.g., at the distal end of insertion portion 30, e.g., portion 34. In some embodiments, one or more electrodes may be external to the body, e.g., an external counter electrode. The contact and operative portions of the electrodes are connected by circuit traces 42, 44, and 46 running on the surface of the substrate. In some embodiments, the traces are provided in channels, or may be embedded within the substrate, or may traverse different sides of the substrate. The conductive contacts, conductive traces, and electrodes are fabricated from conductive material, such as platinum, palladium, gold, carbon, or the like. More than one material may be used for a given sensor. Further details of sensors are described, e.g., in U.S. Pat. Nos. 6,175,572 and 6,103,033, which are incorporated by reference herein for all purposes.

Sensor 14 may include a proximal retention portion 48. The insertion portion 30 and the proximal retention portion 48 are sized and configured to be positioned with a sharp for installation into the skin of a subject, as described herein. In use, the sensor 14 may be configured to bend (e.g., along the line B) and therefore be positioned in two substantially perpendicular, intersecting planes. Such bending may occur prior to or during coupling to the on body electronics as described below. (See FIG. 17).

Figure 3:
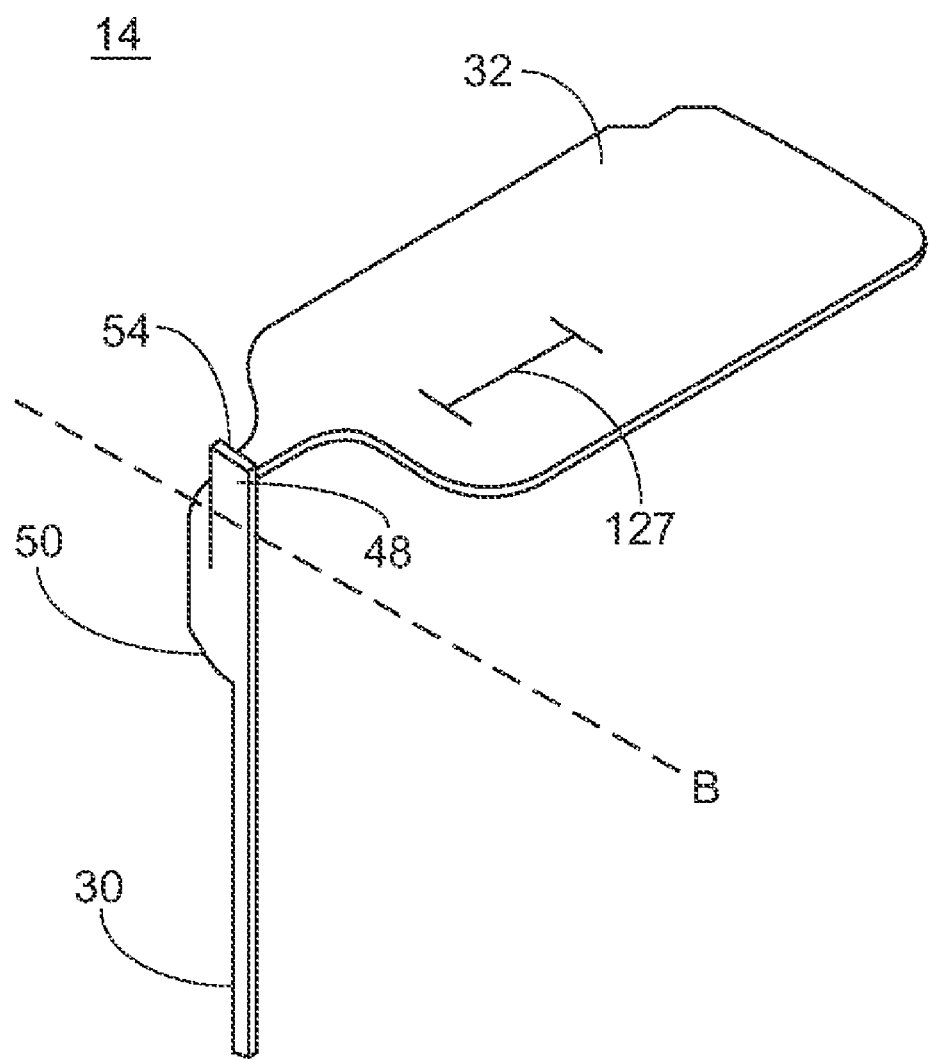

Portions 48 and 52 provide a path for electrical connections, e.g., the conductive traces, between the proximal and distal portions of the sensor. Sensor 14 is further provided with a notch or cut-out 54. Such configuration facilitates the sensor 14 to bend (e.g., along the line indicated by line B) such that retention portion 48 remains upright and therefore be positioned in two substantially perpendicular, intersecting planes, as illustrated in FIG. 3. As will be described below, the sensor tab 50 can be encased in the on body housing 122 to aid in securing and positioning the sensor 14. Proximal retention portion 48 maintains its longitudinal alignment with insertion portion 30 for positioning within an insertion sharp.

Embodiments of analyte sensors have been described herein to operate electrochemically, through an arrangement of electrodes having chemical sensing layers applied thereto, by generating an electrical current proportional to the volume of a redox reaction of the analyte (and indicative of analyte concentration), catalyzed by an analyte-specific oxidizing enzyme. Embodiments exist in which the number of electrodes provided to bring about and detect the level of these reactions is two, three, or a greater number. However, other types of sensors may be employed as described herein.

A portion of sensor 14 may be situated above the surface of the skin, with a distal portion 30 penetrating through the skin and into the subcutaneous space in contact with the user's biofluid, such as ISF. Further details regarding the electrochemistry of sensor 14 is provided in U.S. Pat. Nos. 5,264,104; 5,356,786; 5,262,035; 5,320,725; and 6,990,366, each of which is incorporated by reference herein for all purposes.

In some embodiments, the sensor is implantable into a subject's body for a usage period (e.g., a minute or more, at least one day or more, about one to about 30 days or even longer, about three to about fourteen days, about three to about seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity.

In some embodiments, sensor 14 is employed by insertion and/or implantation into a user's body for some usage period. In such embodiments, the substrate may be formed from a relatively flexible material.

While the embodiments illustrated in FIGS. 2-3 have three electrodes, other embodiments can include a fewer or greater number of electrodes. For example, a two-electrode sensor can be utilized. The sensor 14 may be externally-powered and allow a current to pass which is proportional to the amount of analyte present. Alternatively, the sensor 14 itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference herein for all purposes. The level of current provided by a self-powered sensor may be low, for example, on the order of nanoamperes, in certain embodiments.

Insertion Assembly

Insertion assemblies are provided, which are used to install a medical device to the subject. In some embodiments, an insertion assembly includes an inserter and the medical device itself. The inserter can be configured to insert various medical devices into the subject, such as for example, an analyte sensor, an infusion set, or a cannula. In some embodiments, the inserter can be configured to install a combination of such devices, e.g., a combined sensor/infusion set, etc., at the same or different times or locations. For example, in certain embodiments a given inserter can be configured to install a first device and a second device at different times. In this regard, the inserter can be reusable. For example, an inserter may be modifiable to be used with more than one medical device, to include more than one type of medical device, e.g., by attaching an adapter and/or detaching a portion of an inserter. The inserter can install the medical device in, under, or through the skin of the subject, or place the medical device on the surface of the skin. The medical device can include features or structures, e.g., barbs, tabs, adhesive, etc., to maintain the device in position with respect to the skin after insertion. The inserter device may also be used as a lancet, e.g., to pierce the skin without inserting or installing a medical device.

In some embodiments, an insertion assembly includes an inserter, an analyte sensor, and a power supply. The power supply may be inserted simultaneously with the analyte sensor by the inserter. In other embodiments, the battery is installed after or before installation of the analyte sensor. In such case the power supply may be applied by the inserter or separately. The power supply may be used to provide a current or a potential to the sensor and/or to provide power for communication of one or more signals to the monitor unit.

In some embodiments, an insertion assembly includes an inserter, a medical device such as an analyte sensor, and on-body electronics. The on-body electronics may be deployed and/or installed simultaneously with the analyte sensor by the inserter. In other embodiments, the on-body electronics are installed after or before installation of the analyte sensor. For example, the analyte sensor may be installed by the inserter, and the on-body electronics may be subsequently installed.

In some embodiments, the on-body electronics provide a voltage or current to the analyte sensor. In some embodiments, the on-body electronics process signals provided by the analyte sensor. In further embodiments, the on-body electronics may include communications functionality for providing signal relating to signal provided by the analyte sensor to a further component, such as, e.g., a monitor unit, a computer, or other component. In some embodiments, communications circuitry, such as an RFID antenna, is provided. The power supply may be used to power some or all of these functions. In some embodiments, power is provided from the monitor unit, e.g., via inductive coupling.

An inserter can include a plurality of different components. For example, an inserter may include one or more components for advancing a sharp towards the skin of the subject. The sensor and on-body electronics may be supported by a support structure, such as a carriage. A driver may be provided for advancing the sharp and/or the analyte sensor/support structure. In some embodiments, the actuator is directly or indirectly coupled to the sharp and/or support structure, such that manual force applied by the user to the actuator is transferred to the sharp and/or support structure. In some embodiments, the applied force drives the sharp and/or support structure between a retracted position (within the inserter) and an advanced position (towards the skin of the subject). In some embodiments, the sensor and on-body electronics is maintained in a retracted position prior to installation by contacting projections extending inwardly from a sheath. In accordance with this embodiment, the sensor and on-body electronics are temporarily maintained operatively between the support structure and the projections disposed on the interior wall of the sheath.

An inserter can also include one or more components for retracting the sharp, while allowing the analyte sensor and optional on-body electronics to remain on the subject. The components for retracting the sharp can include a retractor. It is understood that the retractor and the actuator may be the same structure or include some common components. In some embodiments, the retractor is directly or indirectly coupled to the sharp such that the manual force applied by the user is transferred from the retractor to the sharp to retract the sharp from the skin. In other embodiments, a drive assembly may be provided to retract the sharp. For example, the drive assembly may include a spring, motor, hydraulic piston, etc., to retract the sharp away from the skin of the subject. The drive assembly may also include a linear drive component.

In some embodiments, the retractor withdraws the sharp upon actuation by the user. In such cases, the user actuates the retractor when it is desired to withdraw the sharp. For example, the retractor may include a release switch. Upon activation of the release switch, the drive assembly, e.g., the spring or other driver, retracts the sharp from the skin. In other embodiments, the retractor and the actuator include common components. After activating the actuator to advance the sharp and the analyte sensor, the user releases the actuator, which allows the drive assembly to withdraw the sharp from the skin.

In some embodiments, the retractor withdraws the sharp without further user interaction after actuation of insertion. For example, the inserter may include features or components which automatically retract the sharp upon advancement of the sharp and support structure by a predetermined amount. Inserter devices, in which no further action by the user is required to initiate withdrawal of the sharp after insertion, are referred to herein as having "automatic" withdrawal of the sharp.

Inserter Devices

Figure 4:
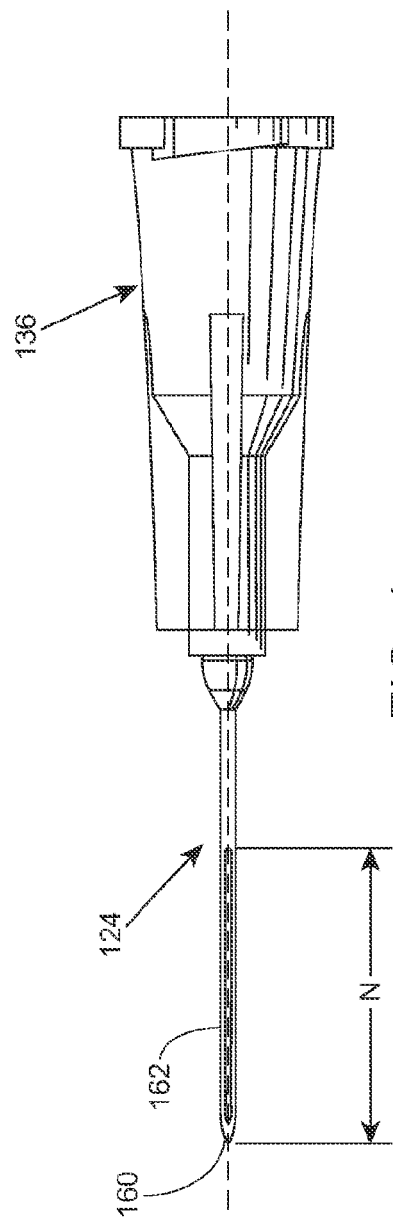
FIGS. 4-5 are schematic views of a needle hub in accordance with one embodiment of the disclosed subject matter.
Figure 5:
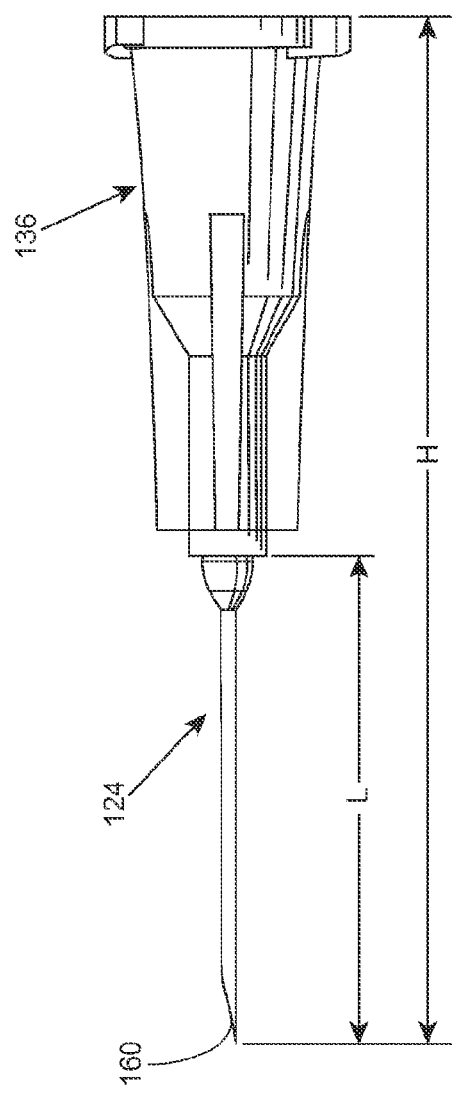

One embodiment of a needle hub for an inserter is illustrated in FIGS. 4-5. Needle hub 136 supports sharp 124, having a sharpened distal portion 160. In some embodiments, as discussed herein, a longitudinal wall opening or gap 162 is provided in at least a portion of the wall of the sharp 124. The length N of the gap 162 is selected to be commensurate with the length of the insertion portion 30 through to the proximal retention portion 48 of the sensor, and in certain embodiments may be about 3 mm to about 50 mm, e.g., about 5 mm, or about 10 mm, or about 15 mm, or about 20 mm. The length L of the sharp 124 may be about 3 mm to about 50 mm, e.g., 5 mm or more, or about 10 mm, or about 20 mm, or about 30 mm, or about 50 mm, and is selected based upon the length of the insertion portion 30 of a sensor and the desired depth of the insertion portion 30 of the sensor 14. In some embodiments, the distance or spacing between the two edges of the gap is about 0.2 mm to about 0.5 mm, e.g., about 0.22 mm, about 0.25 mm, etc.

Figure 7:
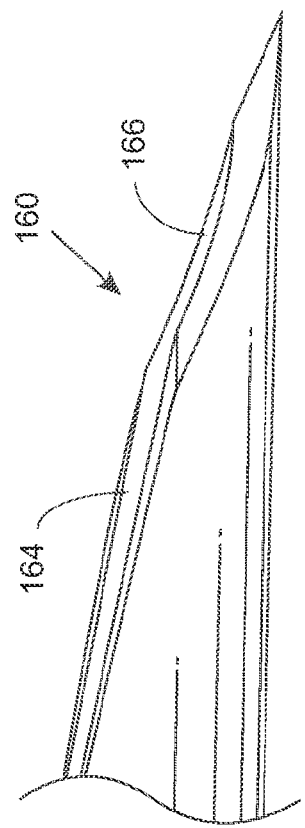
FIG. 7 is a side view of a sharp in accordance with one embodiment of the disclosed subject matter.
Figure 8:
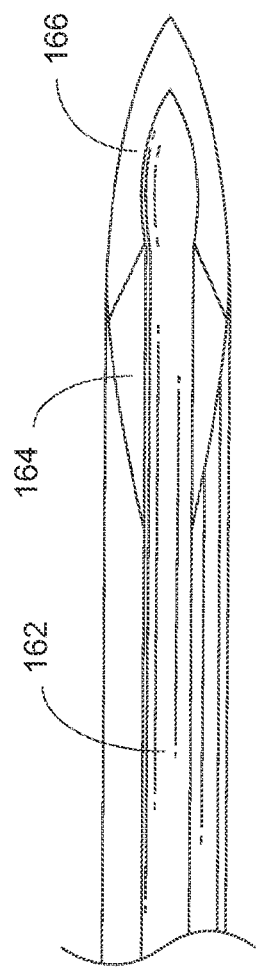
FIG. 8 is a side view of a sharp in accordance with one embodiment of the disclosed subject matter.
Figure 6:
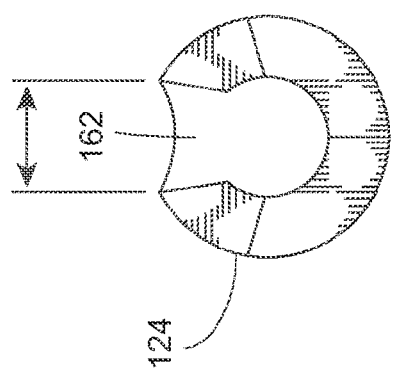
FIG. 6 is a distal end view of a sharp in accordance with one embodiment of the disclosed subject matter.
Figure 9:
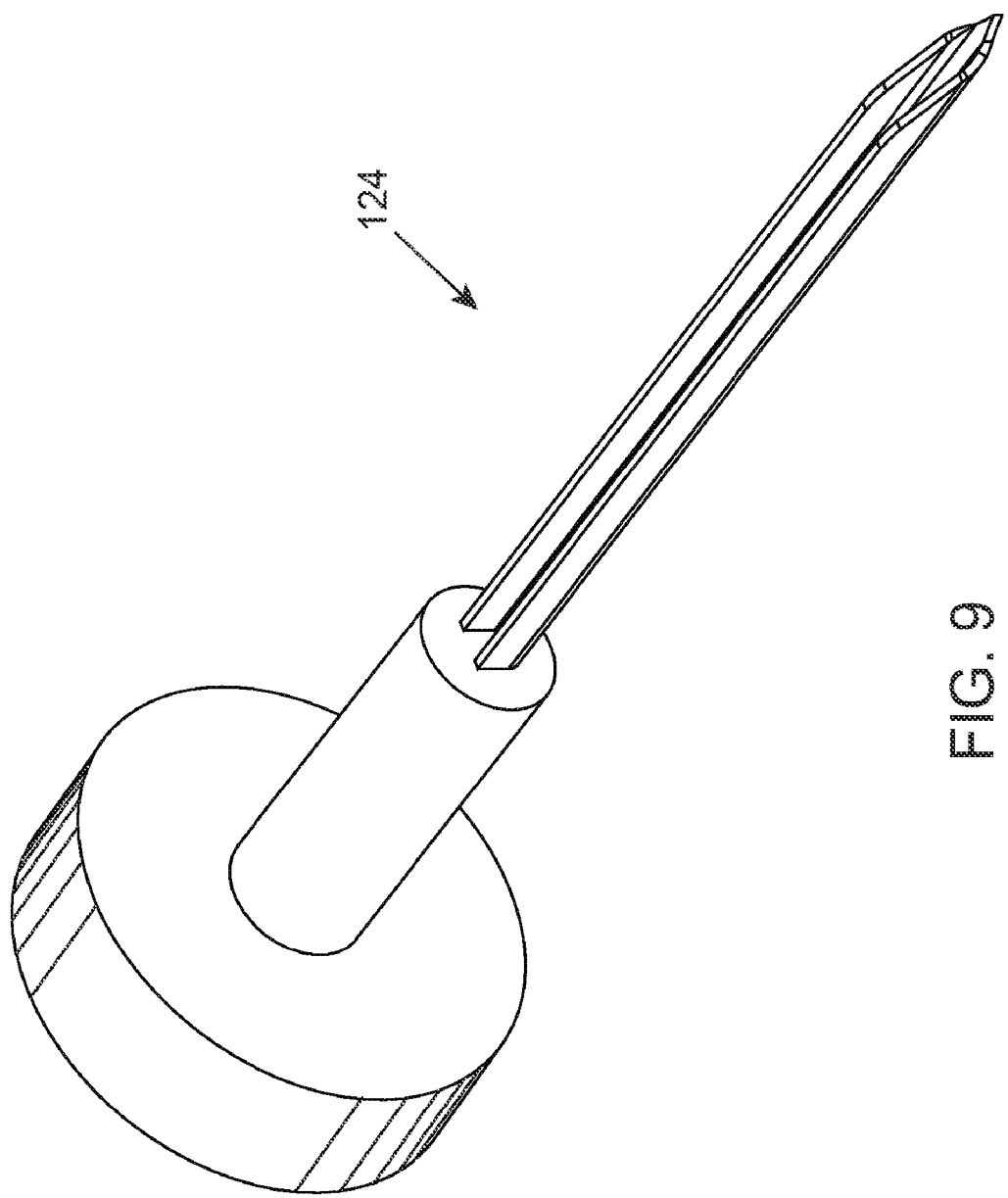
FIG. 9 is a perspective view of a sharp in accordance with one embodiment of the disclosed subject matter.

The distal portion 160 of sharp 124 is illustrated in greater detail in FIGS. 6-8. As illustrated in FIG. 6, sharp 124 has a substantially "C"- or "U"-shaped profile in this embodiment, but may have other configurations, e.g., substantially "V"-shaped. A longitudinal gap 162 is provided in the wall of the sharp 124. FIG. 7 illustrates distal portion 160 is provided with an angled tip. In some embodiments, the angled tip may be provided with a first angled tip portion 164 and a second steep-angled tip portion 166. The exemplary configuration, which includes multiple edges and faces, provides a sharp point to reduce penetration force, trauma, and bleeding for the subject. The distal section of the sensor body has a width sized to fit within the gap 162 of the insertion sharp 124 having a diameter less than about 20 to about 26 gauge, e.g., 21 gauge to about 25 gauge, where in certain embodiments the sharp is 21 gauge or 23 gauge or 25 gauge. Such sharp may be used with a sensor having a width or diameter —at least the portion that is carried by the sharp—of about 0.20 mm to about 0.80 mm, e.g., about 0.25 mm to about 0.60 mm, where in some embodiments the width or diameter of at least a portion of a sensor is 0.27 mm or 0.33 mm or 0.58 mm. In some embodiments, sharp 124 is fabricated from a sheet of metal and folded into a substantially "V," "U" or "C" configuration in cross-section. Various technologies can be used to manufacture a folded sheet of metal to form sharp 124. For example, etched-sheet metal technology can be used to form the sharp 124. In this manner, the sharp can be formed having a very sharp edge so that penetration through the skin during insertion is less painful. In other embodiments, a progressive die technology may be utilized to form a complex sheet-metal shape that has a sharp edge as depicted in FIG. 9. In some embodiments, the sharp 124 can be molded with a plastic cap so that the sharp can be handled during the inserter assembly process. Further, the die cut sharp may be molded with plastic to reinforce the "V," "U" or "C" shaped sheet metal configuration. In other embodiments, a laser-cut sharp can be formed. In this manner, the laser can be used to form the wall opening or gap 162 and first-angled tip portion 164 and a second, steep-angled tip portion 166.

Figure 10:
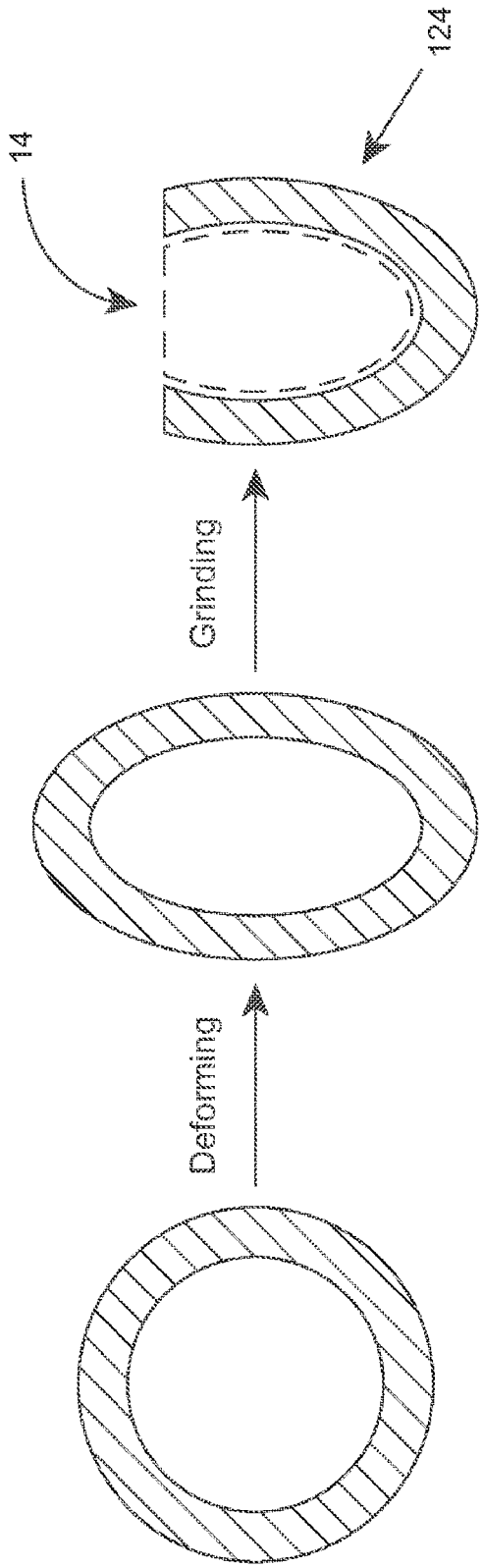
FIG. 10 is a schematic view of an alternate embodiment for forming a sharp to be used in an inserter in accordance with one embodiment of the disclosed subject matter.

In another embodiment, a sharp 124 may be formed from a standard hypodermic needle utilizing the method depicted in FIG. 10. First, the hypodermic needle (having a circular cross-section) is cut to the desired length for sharp 124. Next, the hypodermic needle is compressed so that its cross-section is permanently deformed from a circular shape to an oval shape. The tip of the hypodermic needle is then ground to a bevel to produce a sharp point to reduce the required penetration force, as previously discussed. Finally, the top section of the needle is removed by appropriate techniques (e.g., grinding, electropolishing, etc.). The resulting sharp 124 has a "U"-shaped configuration and provides ample space for the insertion of sensor 14. In some embodiments, the tip-grinding step and the compression step may be carried out in reversed order.

Due to the compression step, a user may initially start with a larger diameter hypodermic needle so that the finished sharp 124 will have similar dimensions to the previously described sharps.

Figure 11:
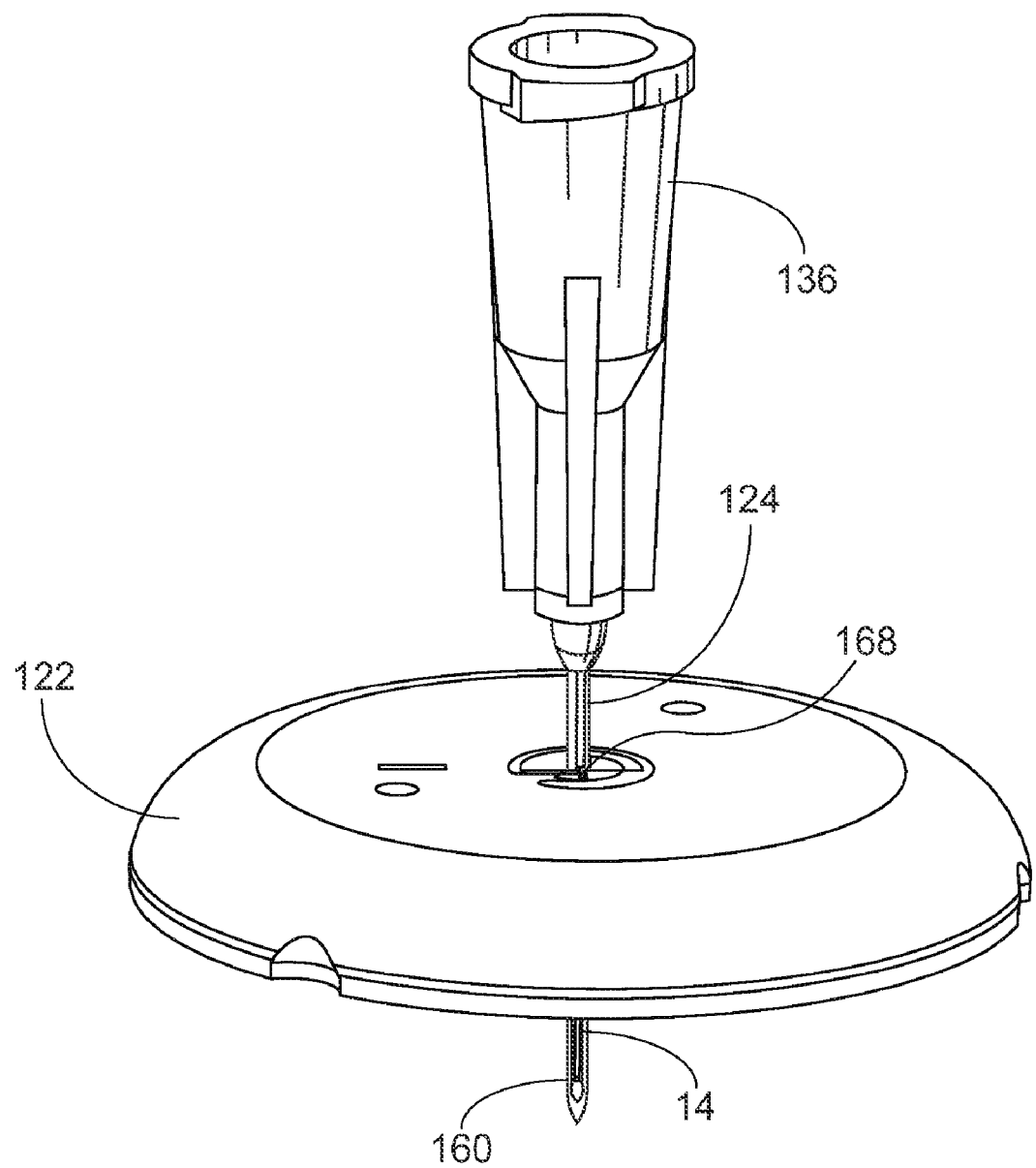
FIG. 11 is a perspective view of an inserter in accordance with one embodiment of the disclosed subject matter.
Figure 12:
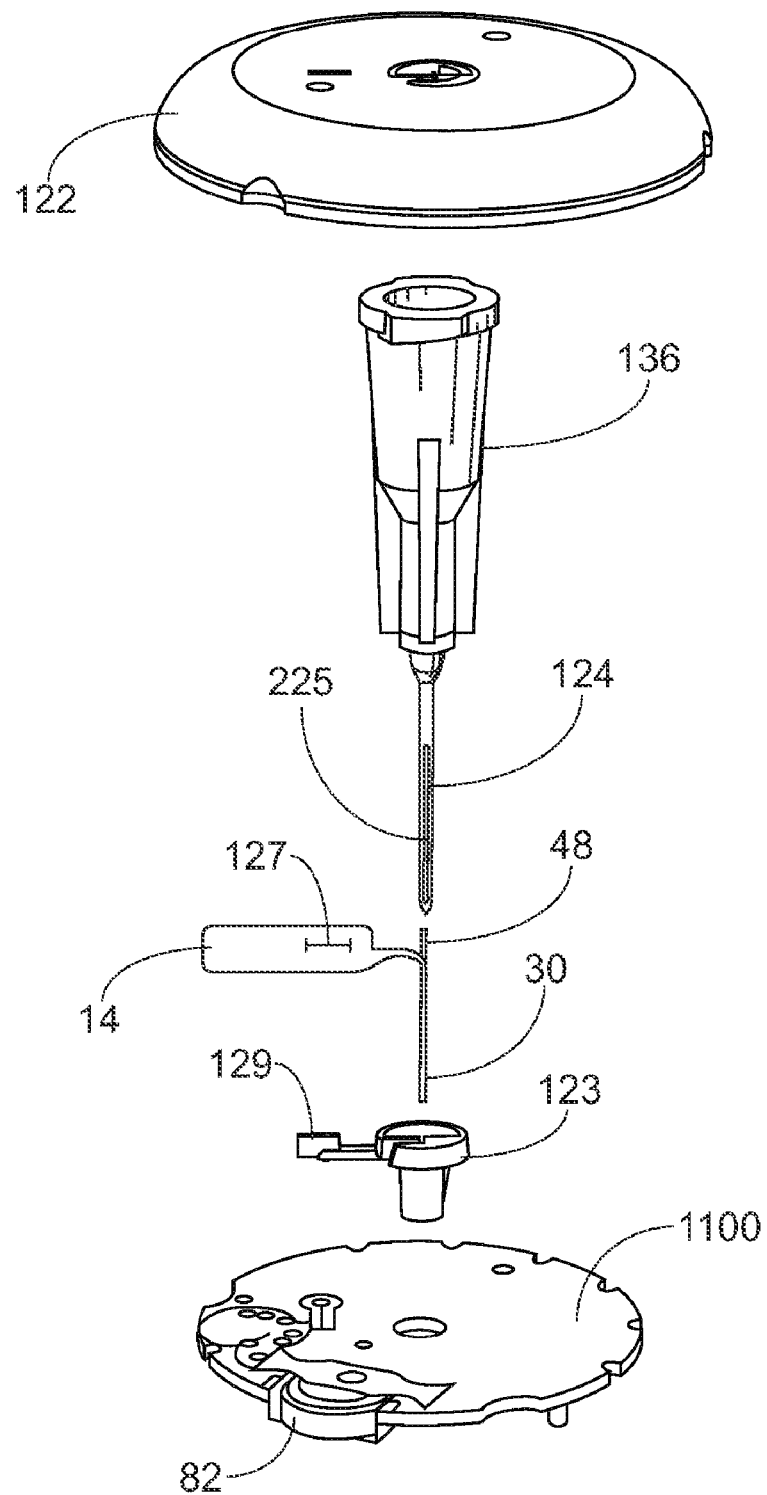
FIG. 12 is a perspective view with parts separated of an inserter in accordance with one embodiment of the disclosed subject matter.

FIGS. 11-12 illustrate the position of on body housing 122 with respect to the needle hub 136 and sharp 124. The on body housing 122 can be configured to hold at least a portion of sensor 14 and sensor control unit. As illustrated in FIG. 11, the sharp 124 extends through an aperture 168 in the on body housing 122. Thus, in some embodiments, the sharp 124 is uncoupled to on body housing 122. The distal portion of sensor 14 is positioned within the sharp 124. As further illustrated in FIG. 12, electronics of the sensor control unit (e.g., a printed circuit board containing electronics components of the on-body unit) and sensor hub 123 are positioned within on body housing 122. Sensor 14 may include a positioning structure, or slit 127, which receives a positioning member, such as tab 129 of sensor hub 123. A power supply 82, such as a battery, e.g., a single-use disposable battery or rechargeable battery, is provided. The power supply 82 is used to provide potential or current to the sensor in some embodiments. In embodiments where a passive communications protocol such as passive RFID is used, no power supply is provided for the communications. Such power is provided by the monitor unit. In some embodiments, where the sensor control unit is used to transmit one or more signals, one or more power supplies may be used to provide power for such communications circuitry. In some embodiments, the active operational life of the battery may exceed the active operational life of the sensor 14.

Figure 13:
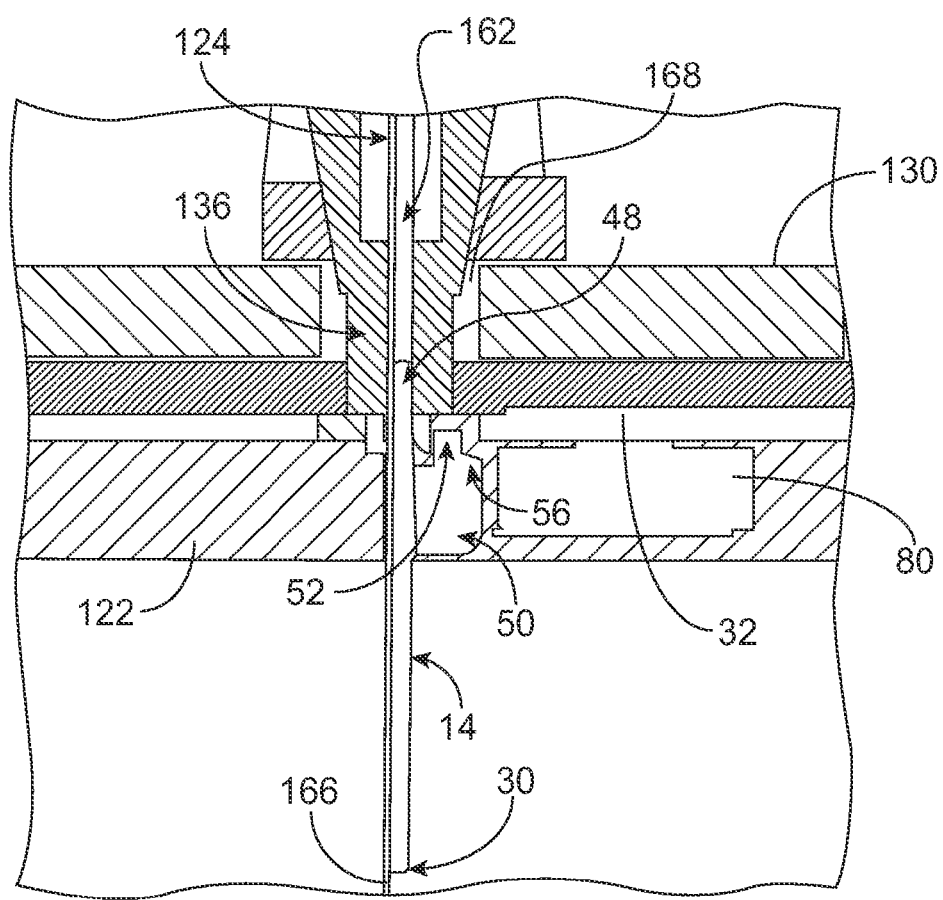
FIG. 13 is an enlarged sectional view with parts separated of an inserter in accordance with one embodiment of the disclosed subject matter.

FIG. 13 illustrates in cross-section the orientation of the on body housing 122 with respect to the sharp 124 of an inserter, such as inserter 500 depicted in FIGS. 14-17. As discussed herein, sensor 14 is disposed in a substantially bent configuration in some embodiments, such that a portion of the sensor, e.g., the insertion portion 30 and the proximal retention portion 48, are substantially vertical (i.e., substantially aligned with the longitudinal axis of an inserter and substantially perpendicular to the skin surface) and the contact portion 32 (shown in profile) is oriented in a substantially horizontal configuration, and in electrical contact with the data-processing unit electronics, such as circuit 80. The sensor tab 50 can be encased in the plastic of the on body housing 122 ("overmolded") and secured in place. The notch 56 provides further stability to the sensor 14, e.g., by allowing the sensor tab 50 to be encased by the material of the on body housing 122, and further provides a means for vertically orienting the sensor 14 during mounting, by allowing vertical positioning of the notch 56 with respect to a vertical landmark of the on body housing 122.

The sensor 14, mounted with the on body housing 122, can be disposed within a recess of the carriage 130 such as a concave recess in the carriage 130. Alternatively, the sensor 14, mounted with the on body housing 122, can be disposed between the support structure and one or more projections extending from the wall of the sheath. In yet another alternative, the sensor 14, mounted with the on body housing 122, can be held in position by a releasable friction fit coupling to the sharp 124. In this manner, the carriage need not have a recess within which the sensor mounted with the sensor housing is disposed. In the initial configuration of the inserter, the sharp 124 extends through a longitudinal aperture 168 formed in a carriage 130. In some embodiments, the aperture 168 is appropriately sized, such that neither the sharp 124 nor needle hub 136 is in contact with the carriage 130. Accordingly, the needle hub 136 (and sharp 124) on the one hand, and the carriage 130 (FIG. 13) and the on body housing 122, on the other hand, move simultaneously but independently from one another. In other embodiments, a friction fit may be provided between the aperture and the sharp.

The insertion portion 30 and proximal retention portion 48 of the sensor 14 are disposed within a longitudinal bore 162 within the sharp 124 (See, e.g., FIG. 6). The proximal retention portion 48 is disposed within the longitudinal bore of the sharp 124 and provides additional stability to the mounting of the sensor 14 within the sharp 124. The longitudinal wall gap or opening 162 of sharp 124 is aligned with the sensor 14, such that the tab 50 and the contact portion 32 extend laterally outward from the sharp 124.

An embodiment of an inserter is illustrated in FIGS. 14-17 and is designated inserter 500. In some embodiments, inserter 500 has a maximum diameter of about 30 mm to about 60 mm, e.g., about 40 mm, about 43 mm, about 43.5 mm, about 50.5 mm, about 54.5 mm, etc. In some embodiments, inserter 500 has a maximum height of about 40 mm to about 80 mm, e.g., about 44 mm, about 46 mm, about 50 mm, about 53 mm, about 67 mm, about 71 mm, etc. In some embodiments, inserter 500 has a volume of about 35 $cm^3$ to about 110 $cm^3$, e.g., about 40 $cm^3$, about 41 $cm^3$, about 50 $cm^3$, about 60 $cm^3$, about 61 $cm^3$, about 62 $cm^3$, about 69 $cm^3$, about 70 $cm^3$, about 79 $cm^3$, about 90 $cm^3$, about 106 $cm^3$, etc. The maximum height is measured from actuator 514 to the distal surface 512 of sheath 542. The volume is measured as the bellows portion 502 and the portion of the sheath 542 that protrudes from bellows portion 502.

Figure 15:
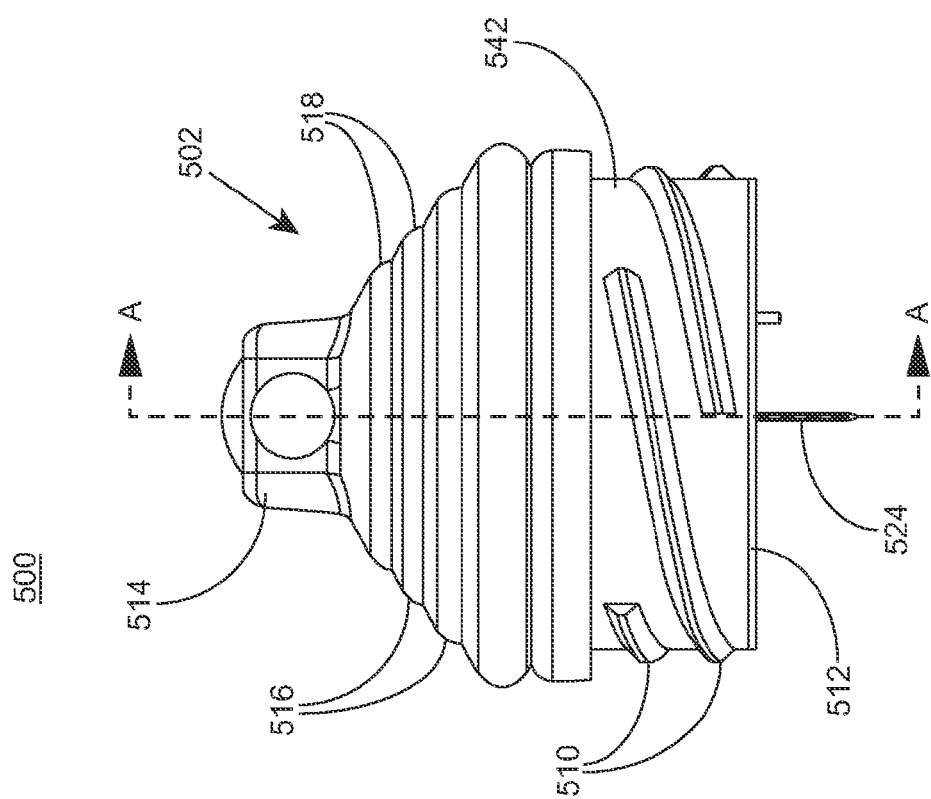
FIG. 15 is a side view of the inserter of FIG. 14 in accordance with the disclosed subject matter.
Figure 14:
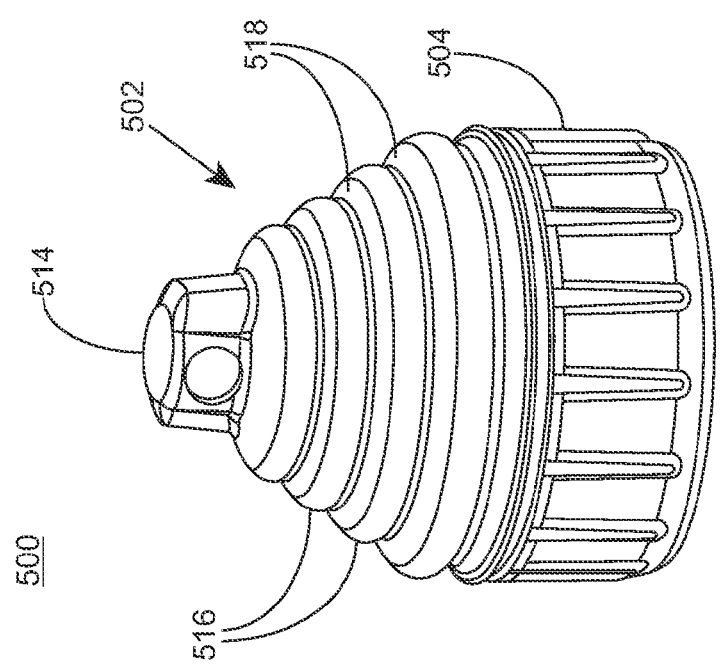
FIG. 14 is a perspective view of another embodiment of an inserter in accordance with the disclosed subject matter.

Inserter 500 includes, a bellows portion 502, a sheath 542, and a removable distal cap 504 for maintaining a sterile environment for the medical device and sharp housed therein. As illustrated in FIG. 15, distal cap 504 is shown removed from sheath 542. Sheath 542 defines a distal surface 512 for placement on the skin of a subject. Inserter 500 may be utilized to advance a medical device into the skin of the subject. In some embodiments, bellows portion 502 is compressed in order to advance the medical device into the skin of the subject. Bellows portion 502 includes a series of concentric folds, including raised portions 516 and folded portions 518.

Figure 16:
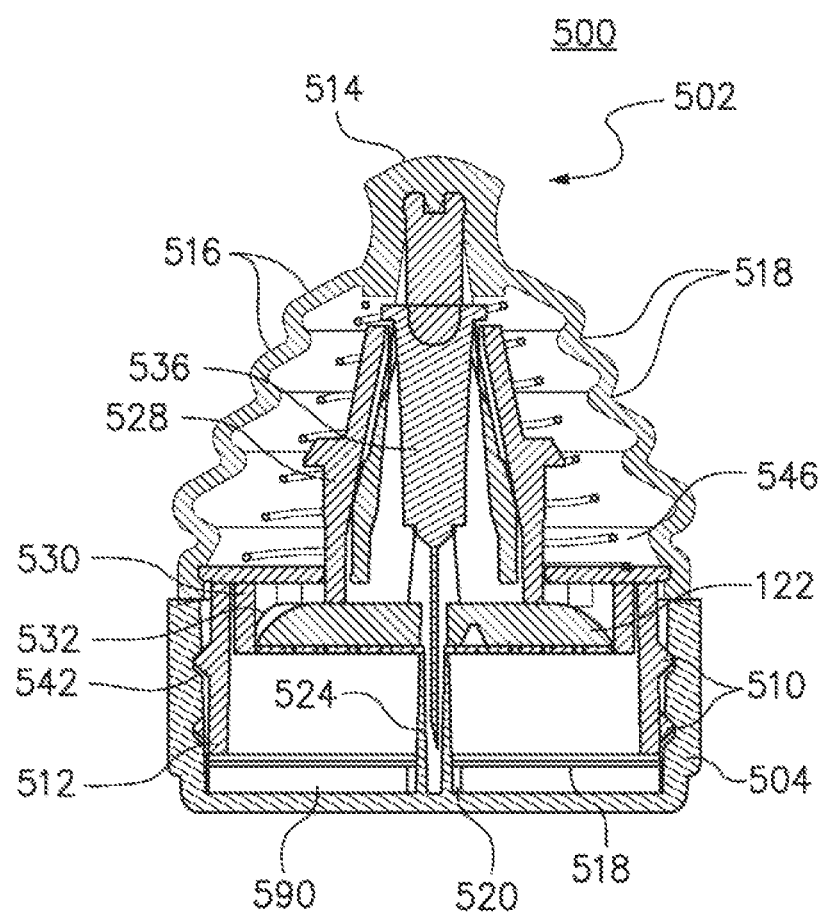
FIGS. 16-17 are cross-sectional views of the inserter of FIG. 14 in accordance with the disclosed subject matter.

Inserter 500 is illustrated in cross-sectional view in FIG. 16 prior to use and prior to removal of cap 504, which is attached to sheath 542 via inter-engagement of threads 510 on sheath and threads on cap 504. Cap 504 includes a desiccant tablet 590. Cap 504 may further include a receptacle for maintaining the position of the sharp 524 within the sheath 542 prior to use.

As illustrated in FIG. 16, the inserter 500 includes an initial configuration in which the bellows portion 502 is disposed in a relaxed, extended position. In such configuration, the sharp 524 is disposed in a position spaced apart from the aperture 520 of the adhesive layer 518. The proximal end portion of the bellows portion 502 includes a button or actuator portion 514. Extending distally from the actuator portion 514 are side walls 528 and needle hub 536. Downward force on the actuator portion 514 causes a downward force on the needle hub 536 and on the carriage 530 (through coupling to side walls 528). Carriage 530 includes a recess 532 for reception of the on body housing 122 therein. Additionally, carriage 530 includes laterally acting spring arms that engage detent features on the on body housing 122 periphery and allow for easy release of on body housing 122 upon completion of insertion. Sharp 524 extends longitudinally from needle hub 536 within the inserter 500. In some embodiments, the sharp is supported at an oblique angle, between about 0° and 90° with respect to the skin surface.

Figure 17:
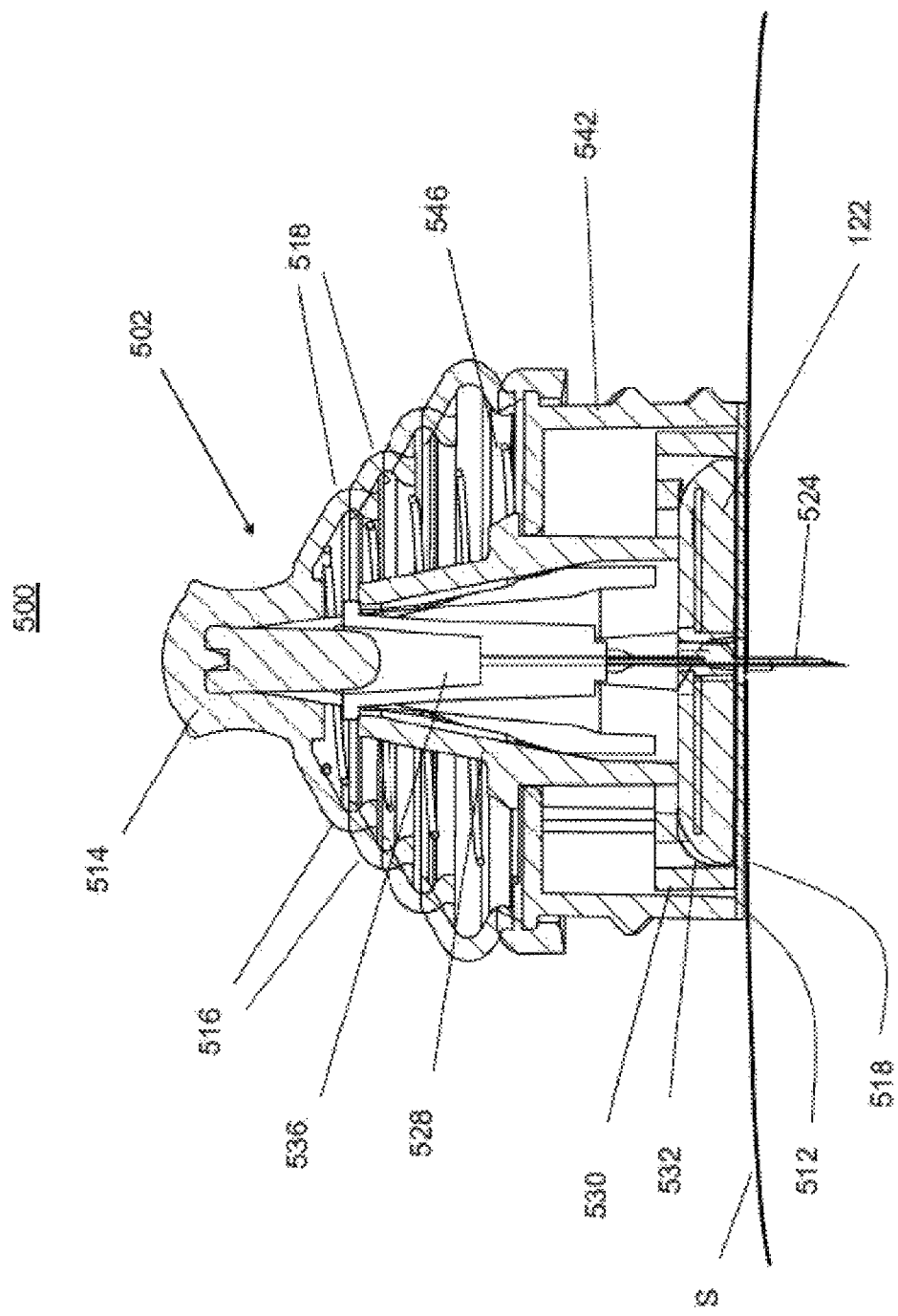

FIG. 17 illustrates inserter 500 in cross-section during insertion. Depression of bellows portion 502 with respect to sheath 542 against the bias of spring 546 causes distal longitudinal movement of the carriage 530 and sharp 524 from a proximal position toward a distal position. During such downward, proximal movement, spring 546 is compressed between an upper (proximal) portion adjacent to actuator 514 and a lower (distal) portion adjacent to sheath 542. As the sharp 524 is urged distally, it carries the sensor insertion portion 30 of sensor 14 (FIG. 12) into the subcutaneous portion of the subject's skin S. In some embodiments, a layer of adhesive between carriage 530 and sheath 542 may be used, requiring the user to exceed a minimum force threshold to break the adhesive bond, thus allowing distal motion of carriage to occur.

By removing downward force on the actuator portion 514, the bias of spring 546 provides an upward (proximal) force, which permits sharp 524 to withdraw from the skin S of the subject. In some embodiments, bellows 502 may provide the entire upward (proximal) force to withdraw sharp 524 from the skin S.

An exemplary driver apparatus is illustrated in FIGS. 18-24 and designated driver apparatus 3600. It is understood that driver apparatus 3600 as described herein (as well as driver apparatuses 3700, 3800, 3900, and 4000) is designed for use with any inserter described herein, such as, e.g., inserter 500 (see FIGS. 14-17) or alternatively inserter 2400 (see FIGS. 44-58). Moreover, in certain embodiments, driver apparatus 3600 (and 3700, 3800, 3900, and 4000) may be configured for use with any inserter apparatus which includes an actuator button or driver for advancing a medical device at least partially into the skin of a patient. Thus, although driver apparatus 3600 (and 3700) is illustrated in cooperation with inserter 500, it is understood that such combination of devices is not intended to encompass all combinations of driver apparatuses and inserters. Similarly, although driver apparatus 3900 (and 4000) is illustrated with inserter 2400, it is understood that such combination of devices is not intended to encompass all combinations of driver apparatuses and inserters. For example, the driver apparatuses disclosed herein provide, among other features, a "button pushing" capability in which the driver apparatus which may be coupled to the actuator button or driver of the inserter to which the driver apparatus is attached.

Another feature of the driver apparatuses described herein is modularity. In some embodiments, the driver apparatus and the inserter may each be capable of independent operation. For example, the inserter may include an actuator button or switch to advance the medical device into the skin of the patient without use of the driver apparatus. The driver apparatus, to the extent provides an actuation capability, may be used with any inserter which has an actuation button that may be contacted by the driver of the driver apparatus. In some embodiments, the modularity allows the driver apparatus to be designed for multiple uses, and the inserter device is capable of a single use. In other embodiments, the inserter is also capable of multiple uses, for example, by replacing the sensor and/or on-body housing with each use.

Driver apparatus 3600 includes a housing 3602 for positioning with respect to an inserter. A loading element 3604—longitudinally movable with respect to housing 3602—is provided. In some embodiments, driver apparatus 3600 is provided with an actuator, e.g., rotating cam 3606, which provides automatic actuation of an inserter. In use, arming button 3620 is pressed (in direction of arrow E) to connect rack 3610 with pinion 3612 (FIG. 18). As illustrated in FIG. 18, once arming button 3620 is pressed, loading element 3604 is depressed downwardly (direction of arrow D) to rotate cam 3606 in a first direction F against the bias of torsion spring 3614. Firing button 3618 maintains the spring in the loaded position until pressed.

As illustrated in FIG. 20, the driver apparatus 3600 is positioned with respect to an inserter 500. Although inserter 500 is illustrated in FIGS. 20-24, it is understood that any inserter may be used with driver apparatus 3600. In some embodiments, the dimensions of the housing 3602 and the location and shape of cam 3606 are selected to interact with the dimensions of the inserter. For example, the housing 3602 may be designed for snap-fit or friction-fit cooperation with the sheath 542 of inserter 500.

As illustrated in FIG. 21, cap 504 of inserter 500 is removed (not shown), thereby allowing placement of adhesive 518 (not shown) on the skin of the subject. To insert sharp 524 (not shown), release button 3618 may be depressed (arrow H).

FIGS. 22-24 illustrate the sequence of motions of the driver apparatus 3600 to drive sharp 524 into the skin of the subject. As illustrated in FIG. 22, upon depressing release button 3618, torsion spring 3614 is released, thereby driving rotation of cam 3606 in the direction J with the bias of the torsion spring 3614. Cam 3606 includes a surface having a protrusion 3607. As illustrated in FIG. 23, further rotation of cam 3606 causes protrusion 3607 to engage actuator button 514 of inserter 500. Consequently, bellows 502 and spring 546 are compressed, and needle hub 536 and carriage 530 are advanced distally (downwardly towards the skin of the subject (Not shown in FIGS. 22-24. See, e.g., FIG. 16). Sharp 524 containing sensor 14 therein is driven into the skin of the subject and on body housing 122 is adhered to the adhesive 518 (not shown). Further unwinding of the torsion spring causes the cam 3606 to further rotate, which results in protrusion 3607 being spaced from the actuator button 514, as illustrated in FIG. 24. As a result, the spring bias of retraction spring 546 (not shown) returns bellows 502 to its expanded configuration, and retracts the sharp 524 from the skin of the subject, leaving the sensor at least partially implanted in the skin.

Another exemplary driver apparatus for actuation of inserters is illustrated in FIGS. 25-31 and designated driver apparatus 3700. In some embodiments, driver apparatus 3700 is a reusable apparatus, whereas the inserter may be a disposable device. Driver apparatus 3700 is substantially identical to driver apparatus 3600, with the substantial differences noted herein and indicated in the accompanying figures.

As illustrated in FIGS. 25 and 26, driver apparatus 3700 includes a housing 3702 for positioning with respect to an inserter. A loading element 3704—longitudinally movable with respect to an upper housing 3705—is provided. In some embodiments, actuator 3706 is a reciprocal element that provides automatic actuation of an inserter. In use, loading element 3704 is advanced laterally (direction of arrow K) along a track 3710 against the normal bias of a drive spring 3714. Upon loading of the drive spring 3714, a locking mechanism 3718 maintains the loading of spring 3714.

As illustrated in FIG. 27, the driver apparatus 3700 is positioned with respect to an inserter 500. Although inserter 500 is illustrated in FIGS. 27-31, it is understood that any inserters may be used with driver apparatus 3700. As illustrated in FIG. 28, cap 504 of inserter 500 is removed (not shown), thereby allowing placement of adhesive 518 (not shown) on the skin of the subject. To insert the sharp 524 (not shown), release button 3718 may be depressed (arrow L).

FIGS. 29-31 illustrate the sequence of motions of the driver apparatus 3700 to drive the sharp 524 into the skin of the subject (see FIG. 16). As illustrated in FIGS. 29-31, upon depressing release button 3718, drive spring 3714 is released, thereby driving sliding member 3707 in the direction M with the bias of the spring 3714. Sliding member 3707 is restrained to lateral motion due its positioning in track 3710. Similarly, actuator 3706 is restrained to longitudinal motion due to its positioning in track 3709. Sliding member 3707 is coupled to actuator 3706 by a crank member 3720, which is pivotally connected to one end to sliding member 3707 and at the other end to actuator 3706. As illustrated in FIG. 30, further lateral movement of sliding member 3707 causes the actuator 3706 to advance distally and to engage the actuator button 514 of inserter 500. Consequently, bellows 502 (not shown) is compressed and needle hub 536 and carriage 530 are advanced distally, thereby driving sharp 524 into the skin of the subject and adhering on body housing 122 (see FIG. 16) to the adhesive 518 (not shown). See, e.g., FIG. 16, for adhesive 518. Further lateral movement of sliding member 3707 causes the actuator 3706 to advance proximally, as illustrated in FIG. 31. As a result, the spring bias of retraction spring 546 (See, e.g., FIG. 16) returns bellows 502 to its expanded configuration, and retracts the sharp 524 from the skin of the subject.

A driver apparatus for actuation of inserters is illustrated in FIGS. 32-43 and designated driver apparatus 3800. In some embodiments, driver apparatus 3800 is a reusable apparatus, whereas the inserter may be inserter 500 described herein. Driver apparatus 3800 is substantially identical to actuators 3600 and 3700, with the substantial differences noted herein and indicated in the accompanying figures.

Figure 33:
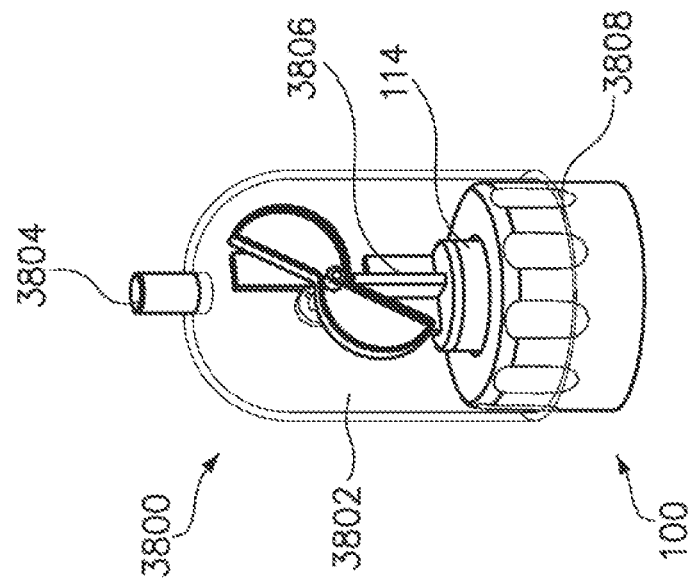
FIG. 33 is a perspective view of an inserter in accordance with another embodiment of the disclosed subject matter.
Figure 32:
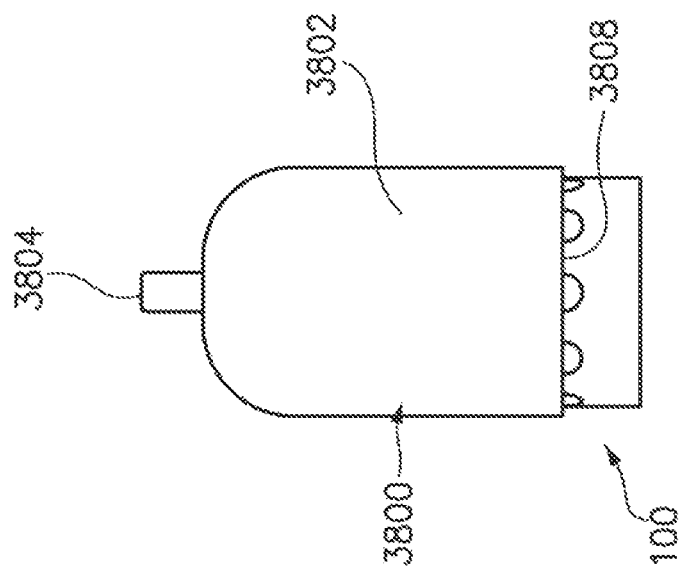
FIG. 32 is a side view of an inserter in accordance with another embodiment of the disclosed subject matter.

As illustrated in FIGS. 32 and 33, driver apparatus 3800 includes a housing 3802 for positioning with respect to an inserter, such as inserter 500 described herein. A loading element 3804 is provided which is longitudinally movable with respect to housing 3802. Depression of the loading element causes a rotor 3808 to rotate against the bias of a torsion spring (not shown). A locking element (not shown) maintains the loading of the torsion spring.

Figure 34:
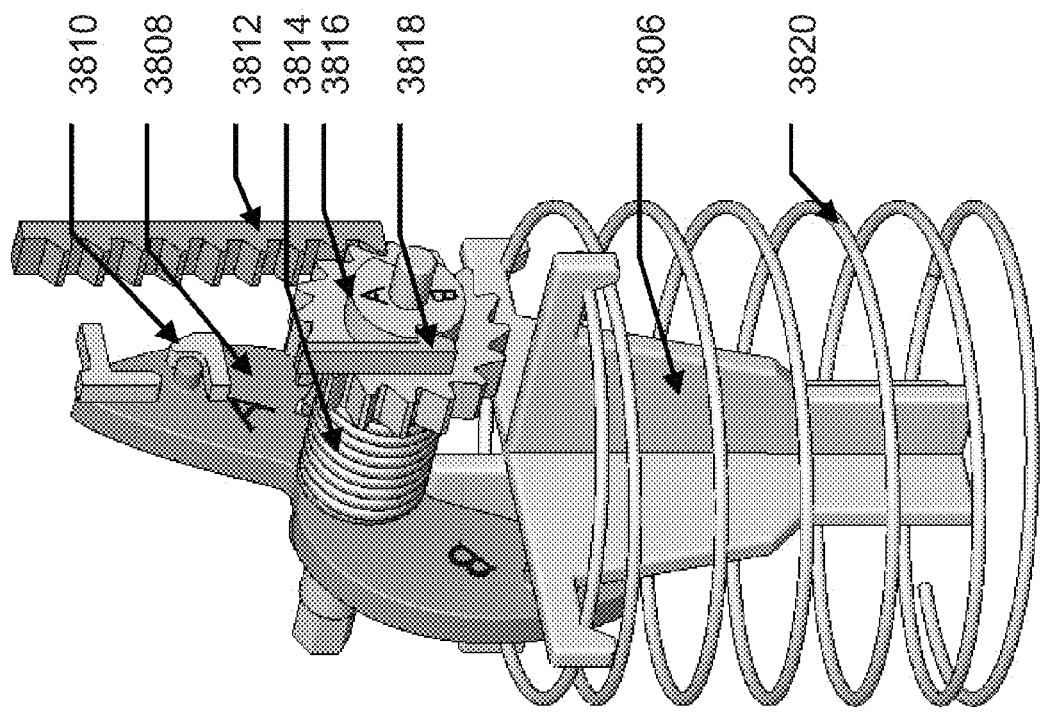
FIGS. 34-43 are views of the inserter of FIGS. 32-33 showing the inserter actuation process.
Figure 35:
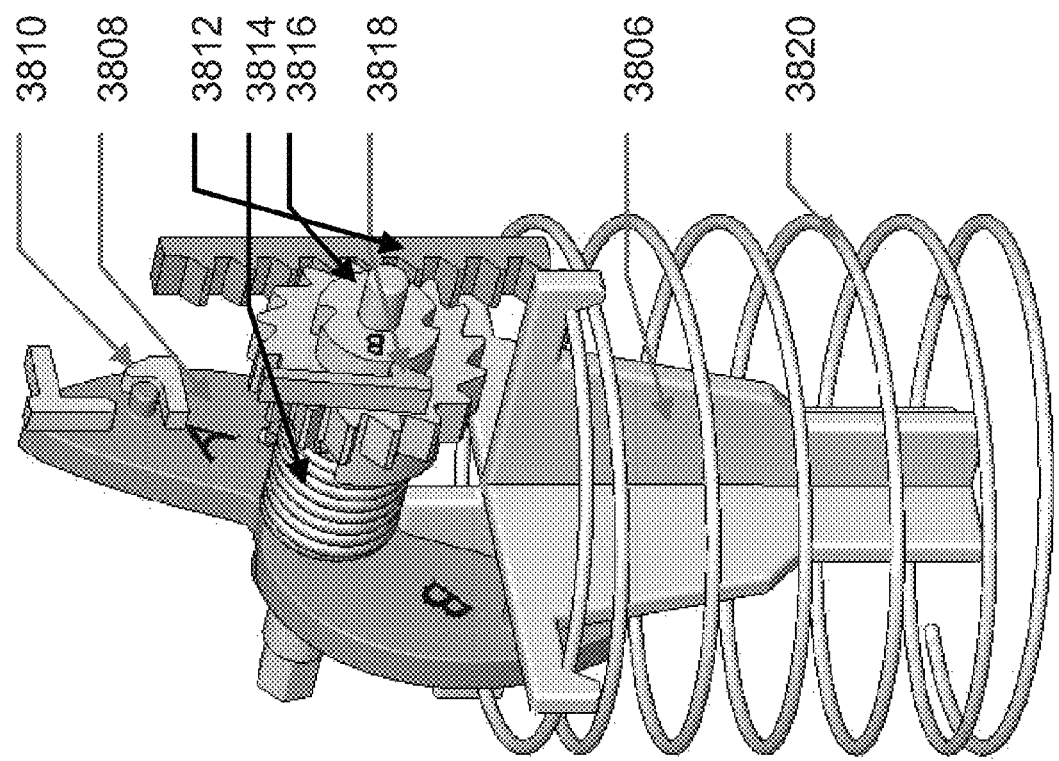
Figure 36:
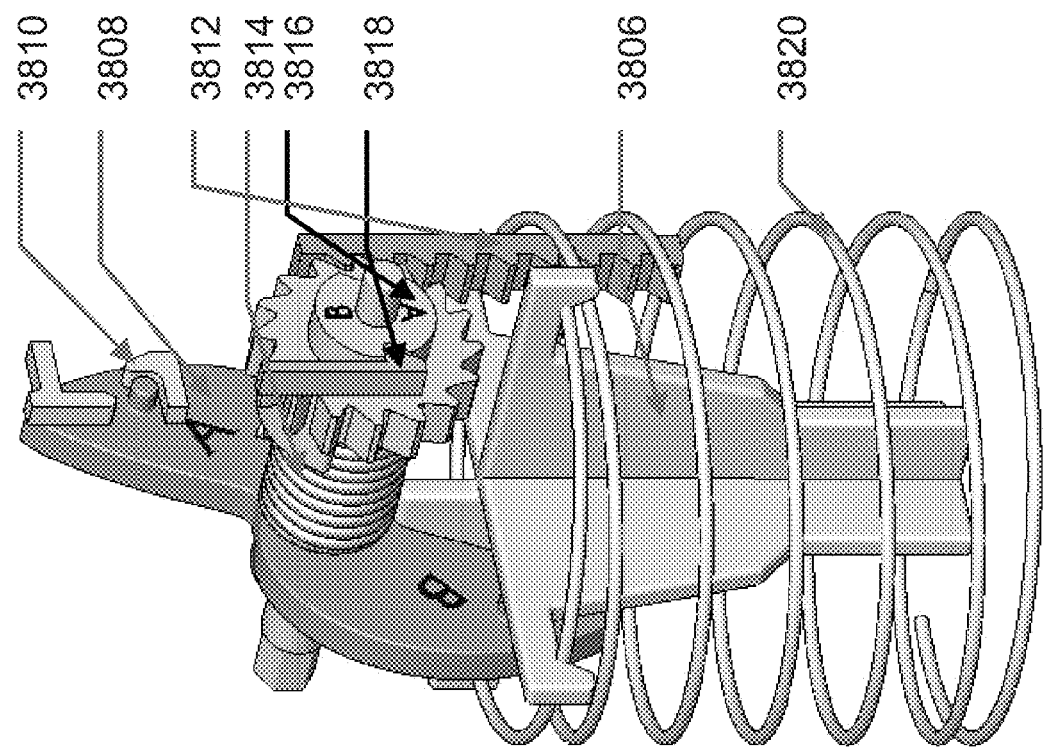
Figure 37:
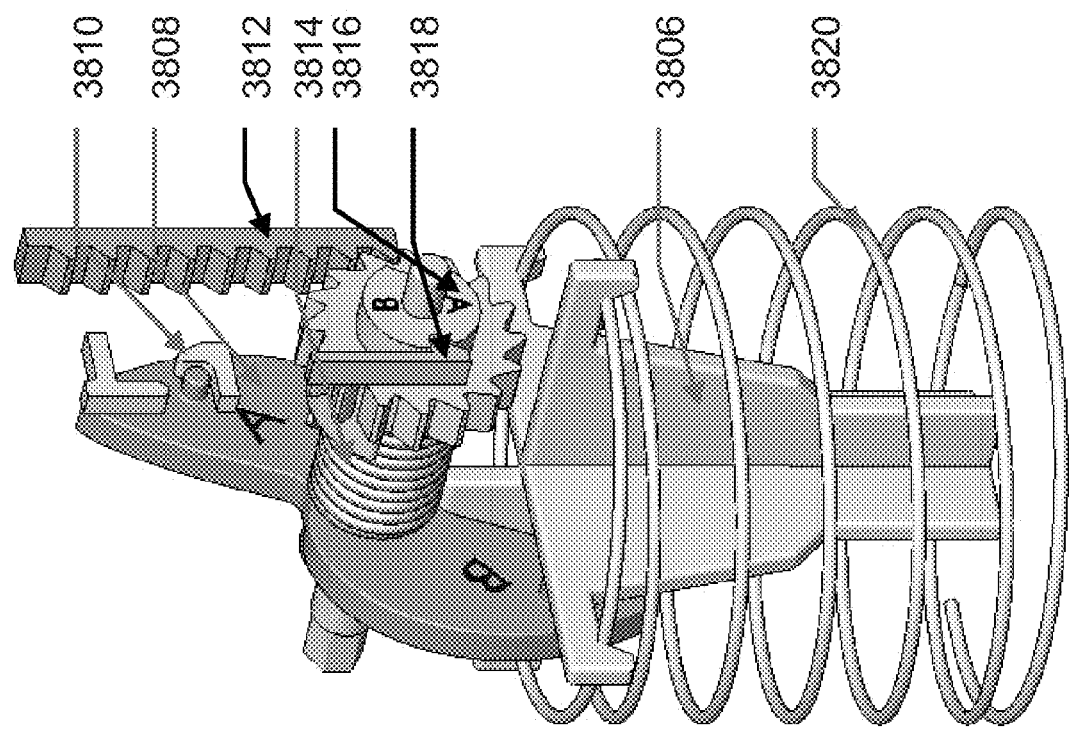

An enhanced view of the actuation of driver apparatus 3800 is depicted in FIGS. 34-43. As depicted in FIG. 34, driver apparatus 3800 includes trigger 3810, cam 3808, arming button 3812, torsion spring 3814, shaft 3816, pawl 3818, actuator 3806, and return spring 3820. To arm driver apparatus 3800, loading element 3804 (not shown) is pressed, causing arming button 3812 to be pushed down, winding shaft 3816 and thus torsion spring 3814 (FIG. 35). Pawl 3818 locks shaft 3816 into place (FIG. 36). After a user depresses loading element 3804, arming button 3812 returns to its original position while shaft 3816 is held in place by pawl 3818 (FIG. 37).

Figure 38:
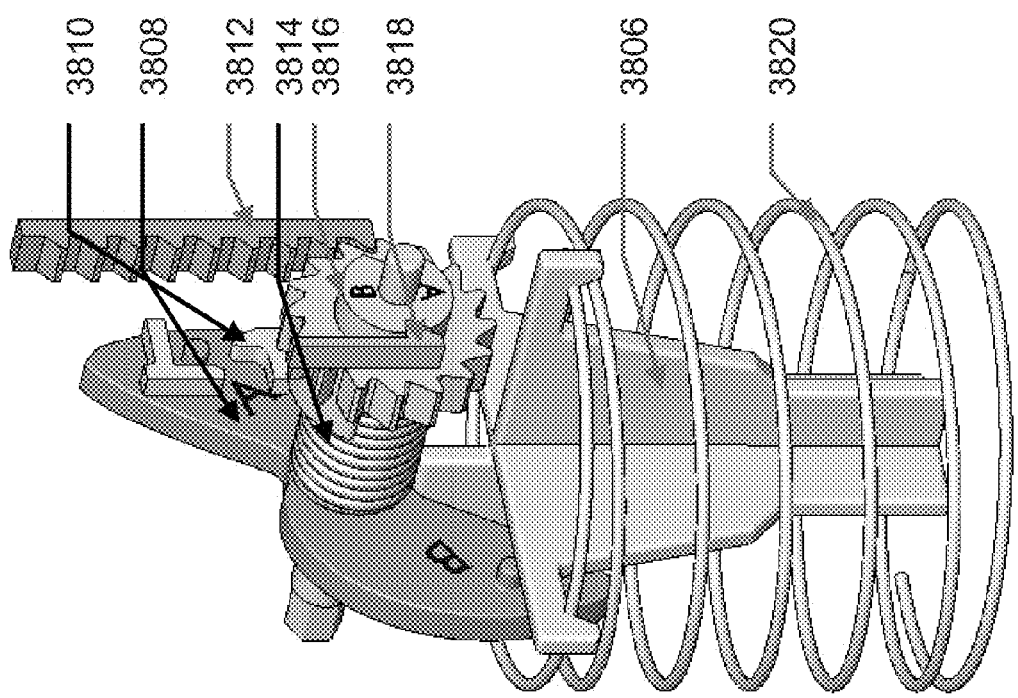

In order to actuate driver apparatus 3800, a user again pushes loading element 3804. This causes trigger 3810 to move in a downward motion, causing cam 3808 to be released. In some embodiments, loading element 3804 is used to alternately depress arming button 3812 and trigger 3810. Cam 3808 is then driven forward by torsion spring 3814 (FIG. 38). In some embodiments, a first loading element is used to depress arming button 3812, and a second loading element is used to depress trigger 3810 (not shown).

Figure 39:
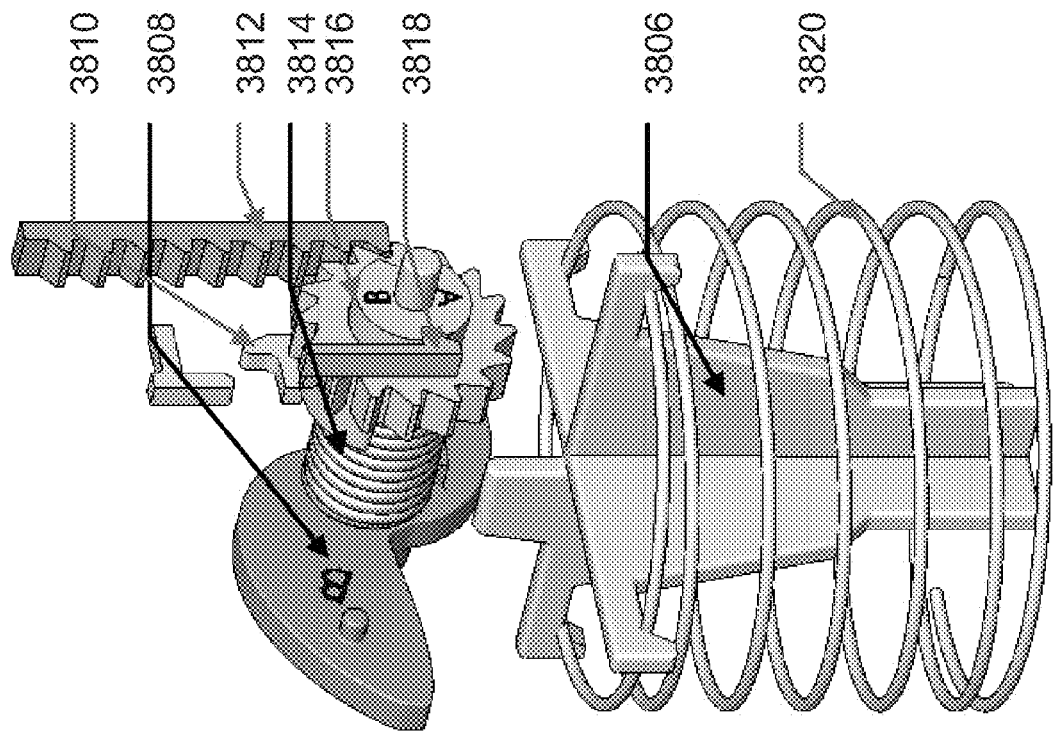
Figure 40:
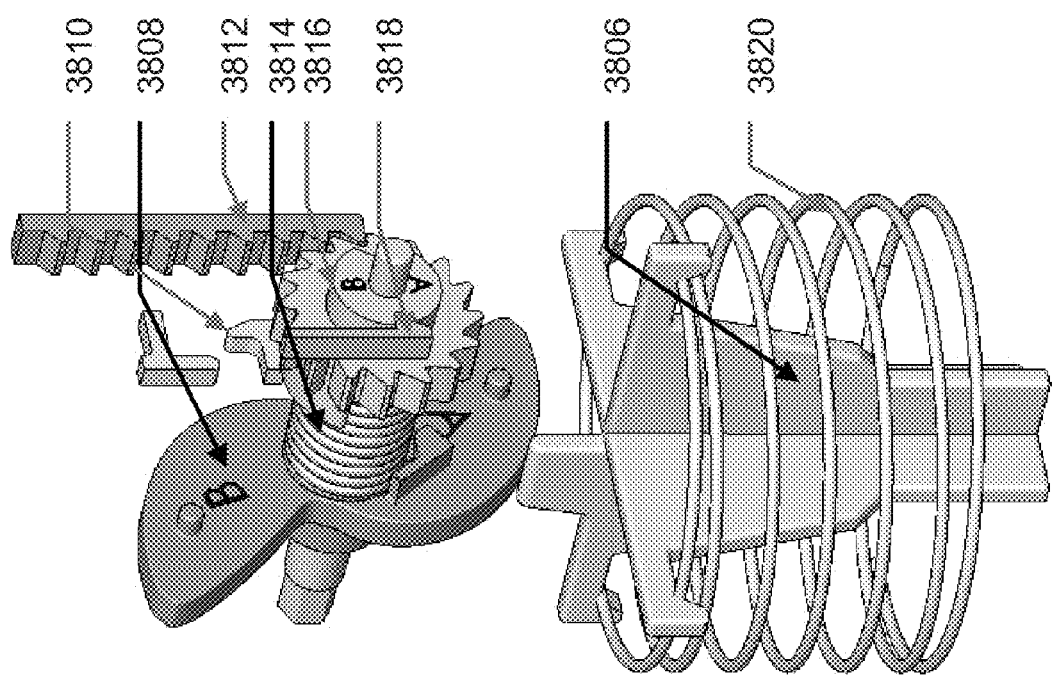
Figure 41:
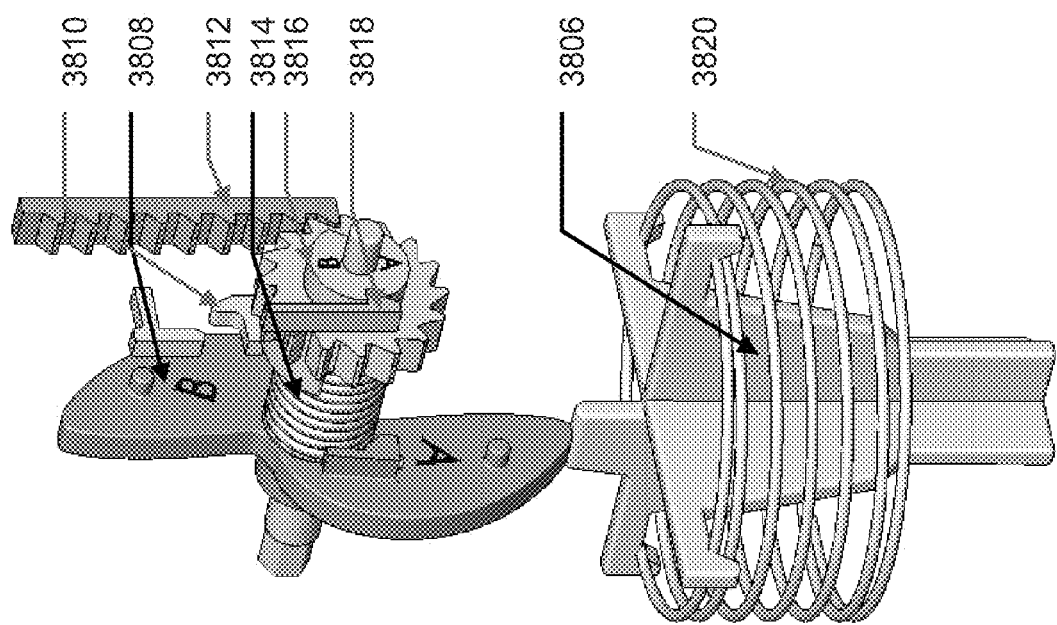
Figure 42:
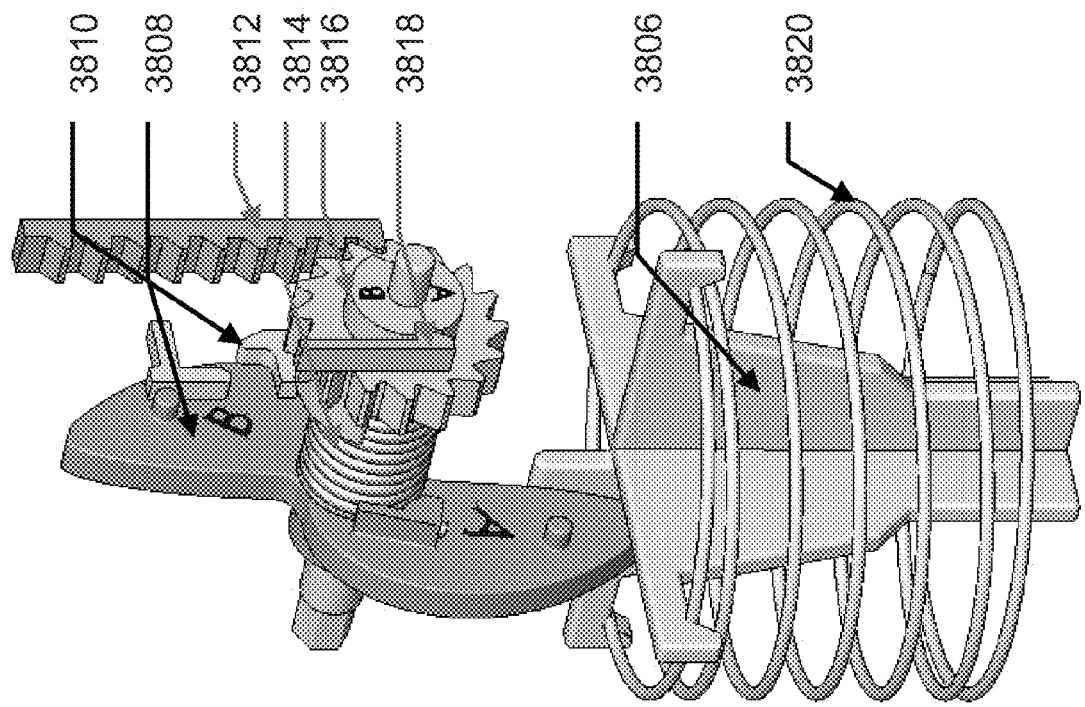
Figure 43:
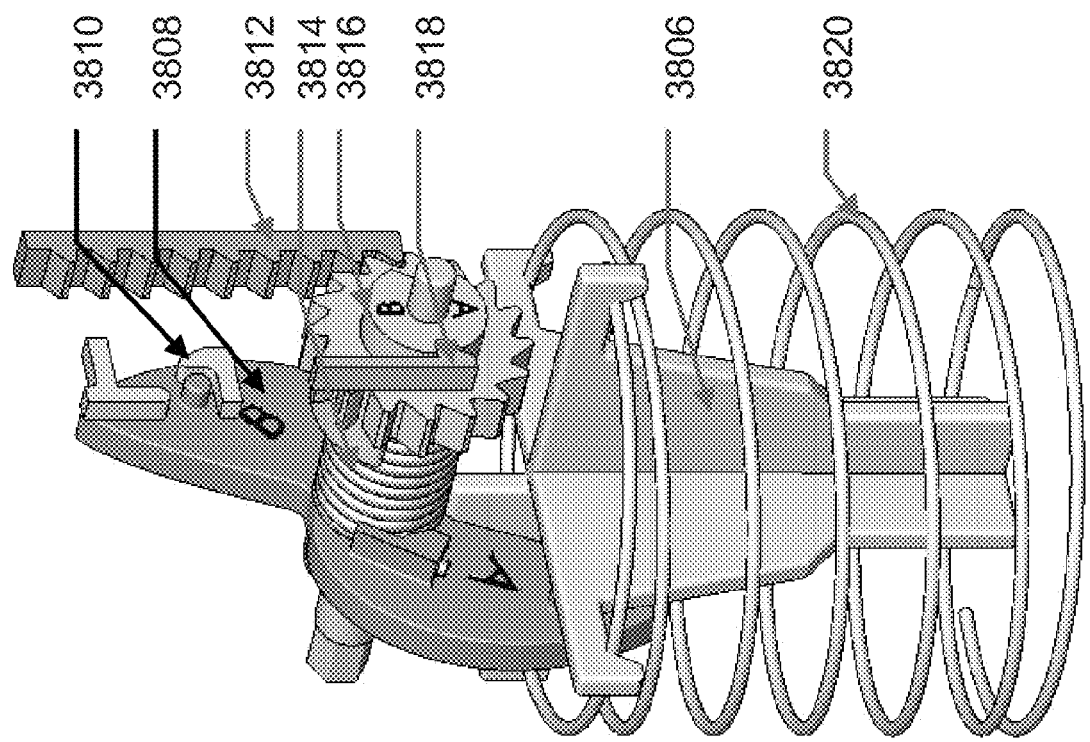

As cam 3808 rotates, it pushes down on actuator 3806 (FIGS. 39-40). At the end of the stroke, there is a slight dwell. This allows the sensor body to be held and pressed onto the adhesive skin patch (FIG. 41). After a full rotation, cam 3808 is stopped by trigger 3810 as shown in FIG. 43. Return spring 3820 pushes actuator 3806 back up, releasing pressure on the inserter. When trigger 3810 is released by the subject, cam 3808 continues to rotate until it is in the home position, thereby allowing driver apparatus 3800 to be used again (FIG. 43).

With continued reference to FIG. 33, inserter 500 supports an on body housing 122 and sensor 14. A sharp (not shown) is used to advance the sensor into the skin of the patient. Actuator 3806 contacts actuator 114 (substantially identical to actuator 514) of inserter 500 to drive the sharp and sensor downward towards the subject's skin.

Figure 44:
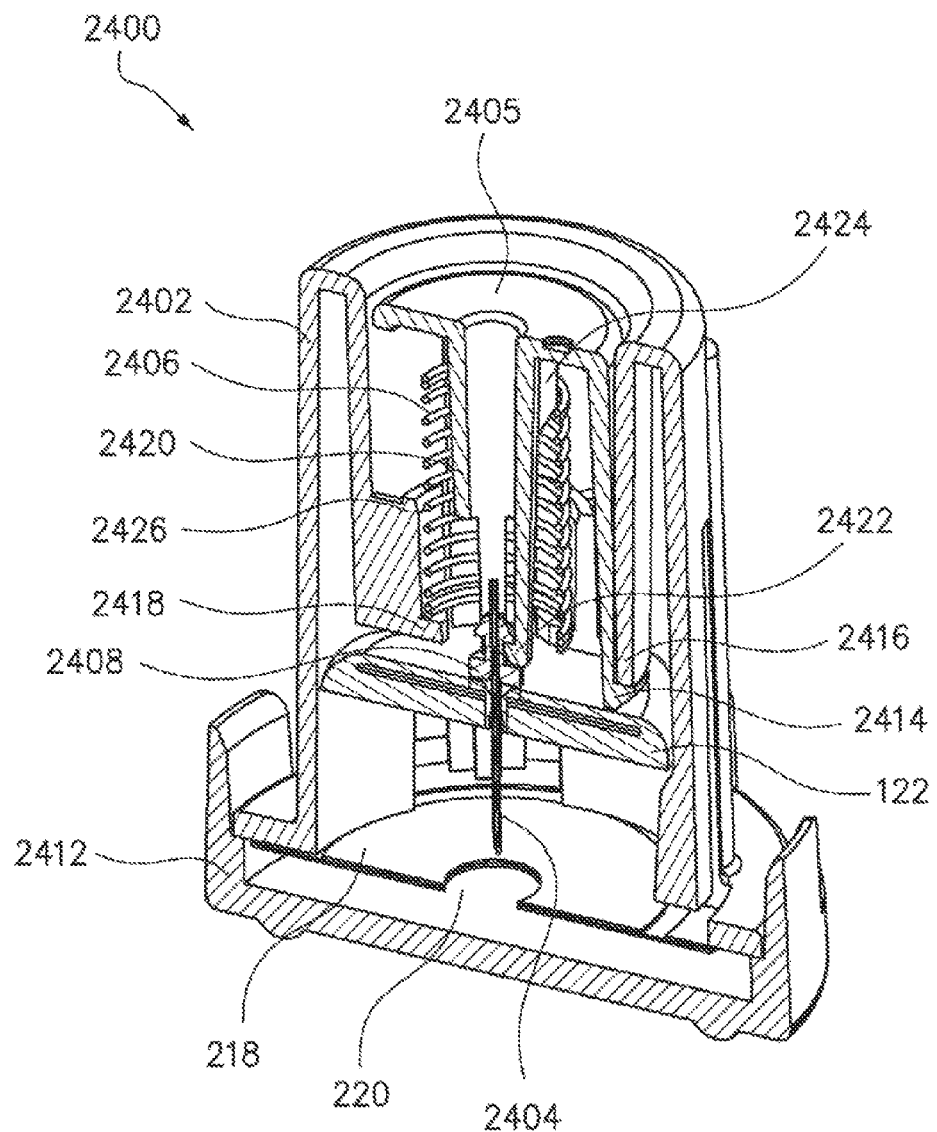
FIG. 44 is a cross-sectional view of another inserter in accordance with the disclosed subject matter.

An inserter 2400 in accordance with another exemplary embodiment is illustrated in FIG. 44. In some embodiments, inserter 2400 has a maximum diameter of about 30 mm to about 60 mm, e.g., about 40 mm, about 43 mm, about 43.5 mm, about 50.5 mm, about 54.5 mm, etc. In some embodiments, inserter 2400 has a maximum height of about 40 mm to about 80 mm, e.g., about 44 mm, about 46 mm, about 50 mm, about 53 mm, about 67 mm, about 71 mm, etc. In some embodiments, inserter 2400 has a volume of about 35 $cm^3$ to about 110 $cm^3$, e.g., about 40 $cm^3$, about 41 $cm^3$, about 50 $cm^3$, about 60 $cm^3$, about 61 $cm^3$, about 62 $cm^3$, about 69 $cm^3$, about 70 $cm^3$, about 79 $cm^3$, about 90 $cm^3$, about 106 $cm^3$, etc. The maximum height is measured from top of housing 2402 to the bottom of housing 2402. The volume is measured as the volume of housing portion 2402.

With reference to FIG. 44, inserter 2400 includes a housing 2402 and a removable distal cap 2412 for protecting the medical device and sharp housed therein. Housing 2402 and distal cap 2412 may be fabricated from any suitable materials such as metal, plastic, etc. In some embodiments, cap 2412 may be fabricated from a polymer or plastic material.

Figure 45:
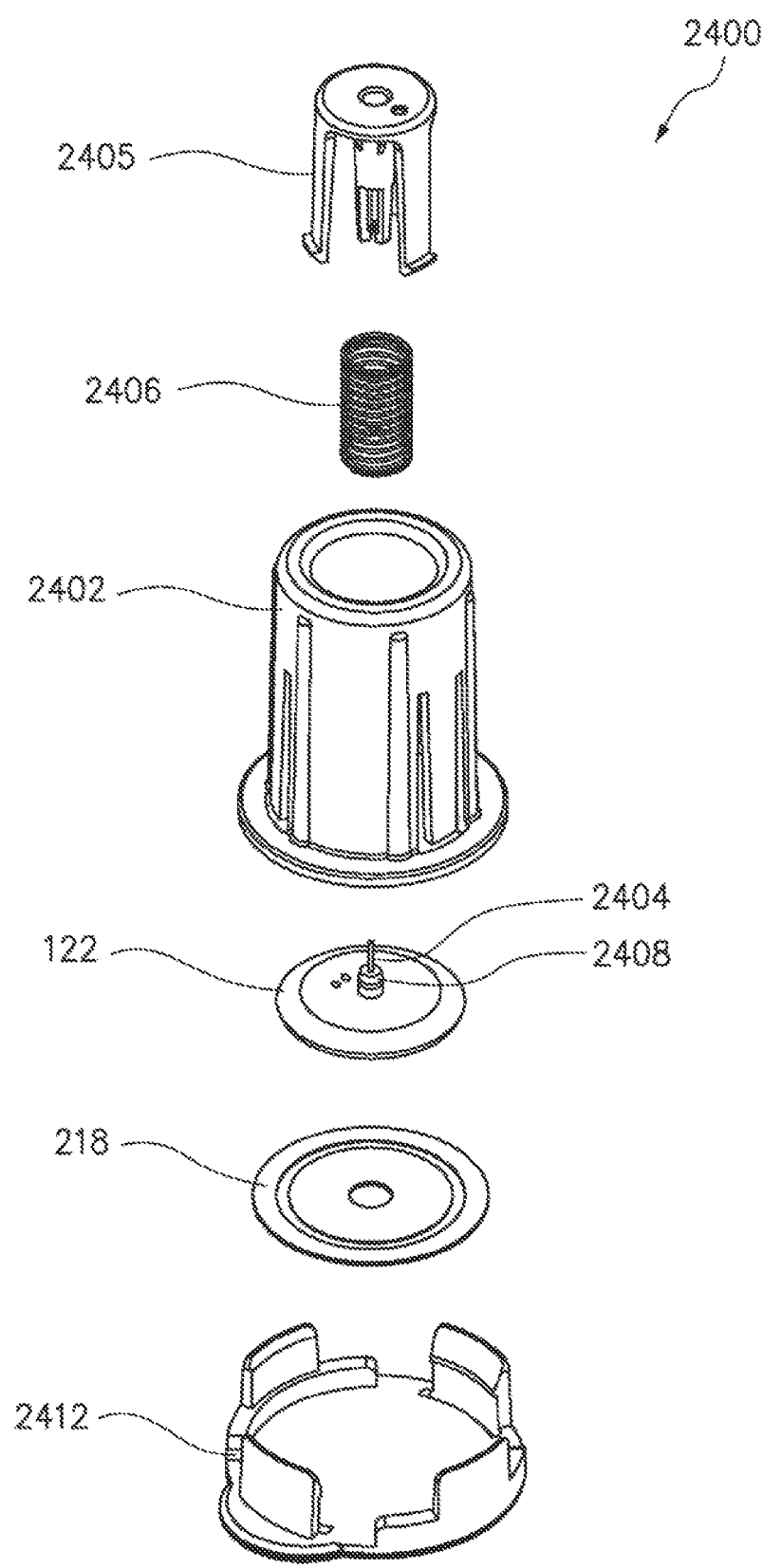
FIG. 45 is an exploded perspective view of the inserter of FIG. 44 in accordance with the disclosed subject matter.

An exploded view of the components of inserter 2400 is illustrated in FIG. 45. As shown, inserter 2400 generally comprises plunger 2405, spring 2406, housing 2402, sharp 2404, on body housing 122, sharp holder 2408, adhesive patch 218, and cap 2412 when fully assembled.

Figure 46:
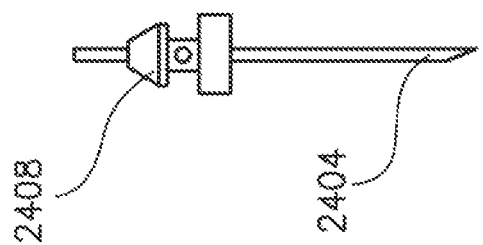

A more detailed view of sharp holder 2408 is shown in FIG. 46. Needle holder 2408 retains sharp 2404 in a fixed position with respect to itself within inserter 2400, thereby allowing it to safely penetrate a subject's skin during later use.

Figure 47:
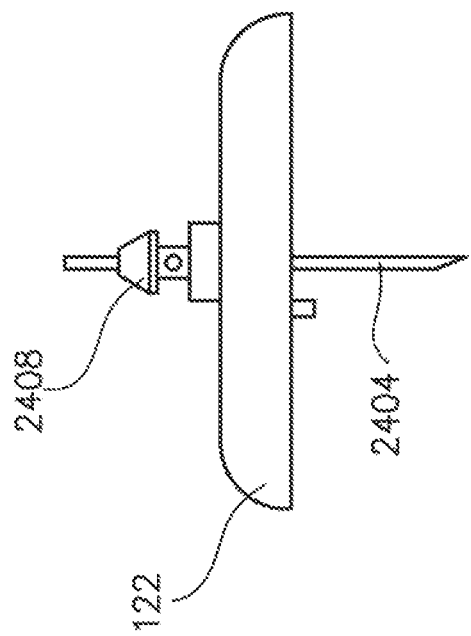

To assemble inserter 2400, sharp 2404 is inserted through an opening in on body housing 122 as shown in FIG. 47. Needle holder 2408 prevents sharp 2404 from being fully inserted through on body housing 122. In some embodiments, on body housing 122 includes an analyte sensor 14 and a sensor control unit.

Figure 48:
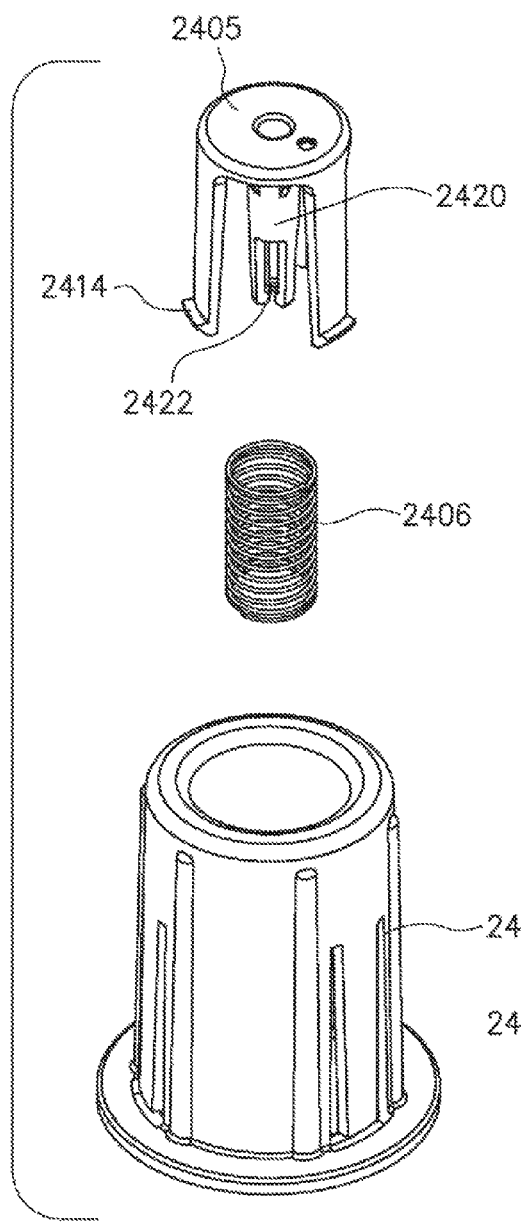
Figure 49:
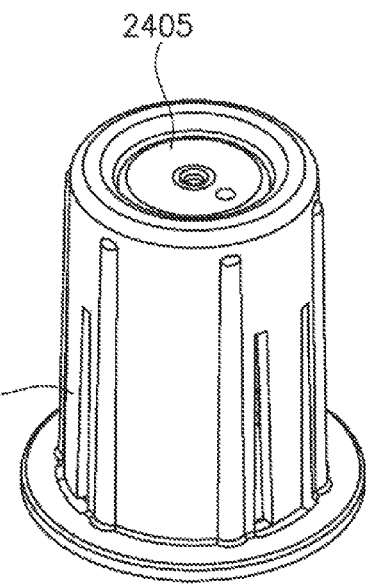

Next, plunger 2405, spring 2406, and housing 2402 are assembled as shown in FIGS. 48-50. Plunger 2405 contains a spring retention member which is inserted through the center of spring 2406. Lip 2414 of plunger 2405 engages inner wall 2416 (not shown) of housing 2402 when assembled (FIG. 44). This causes spring 2406 to be contained between lip 2418 of housing member 2402 and the bottom surface 2424 (not shown) of plunger 2405. The resulting sub-assembly of inserter 2400 allows plunger 2405 to move between a proximal position, with spring 2406 fully extended, and a distal position, wherein bottom surface 2424 engages wall 2426 of housing 2402.

The sensor housing assembly shown in FIG. 47 is then inserted into the inserter sub-assembly shown in FIGS. 48-50. As shown in FIG. 50, on body housing 122 is inserted into housing 2402 with the tip of sharp 2404 pointing away from plunger 2405. The resulting assembly is depicted in FIG. 51. As shown in FIG. 44, grooves on sharp holder 2408 engage tabs 2422 on plunger 2405. The on body housing 122 is axially retained in the housing 2402 by the housing arms detent features 2440 (not shown).

Figure 52:
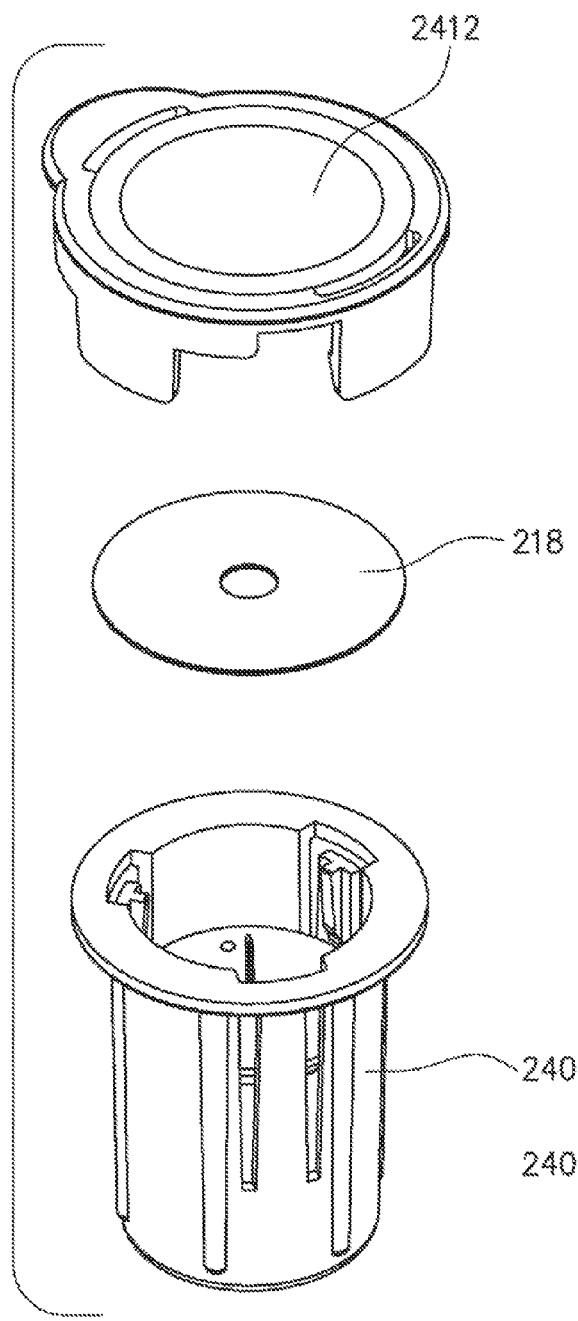
Figure 53:
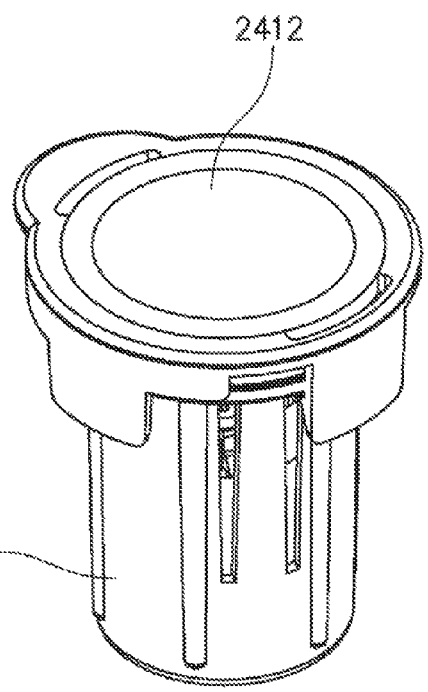

Finally, adhesive patch 218 is placed over the opening of housing 2402 and cap 2412 is snap fit over housing 2402 as shown in FIG. 52. The fully assembled inserter 2400 is depicted in FIG. 53. In some embodiments, adhesive pad 218 has an adhesive material on both faces. A central aperture 220 may be provided in adhesive pad 218 to allow sharp 2404 to be deployed into the skin of a subject. During insertion, sharp 2404 passes through aperture 220 and into the skin of the subject carrying at least the sensor with it.

Figure 54:
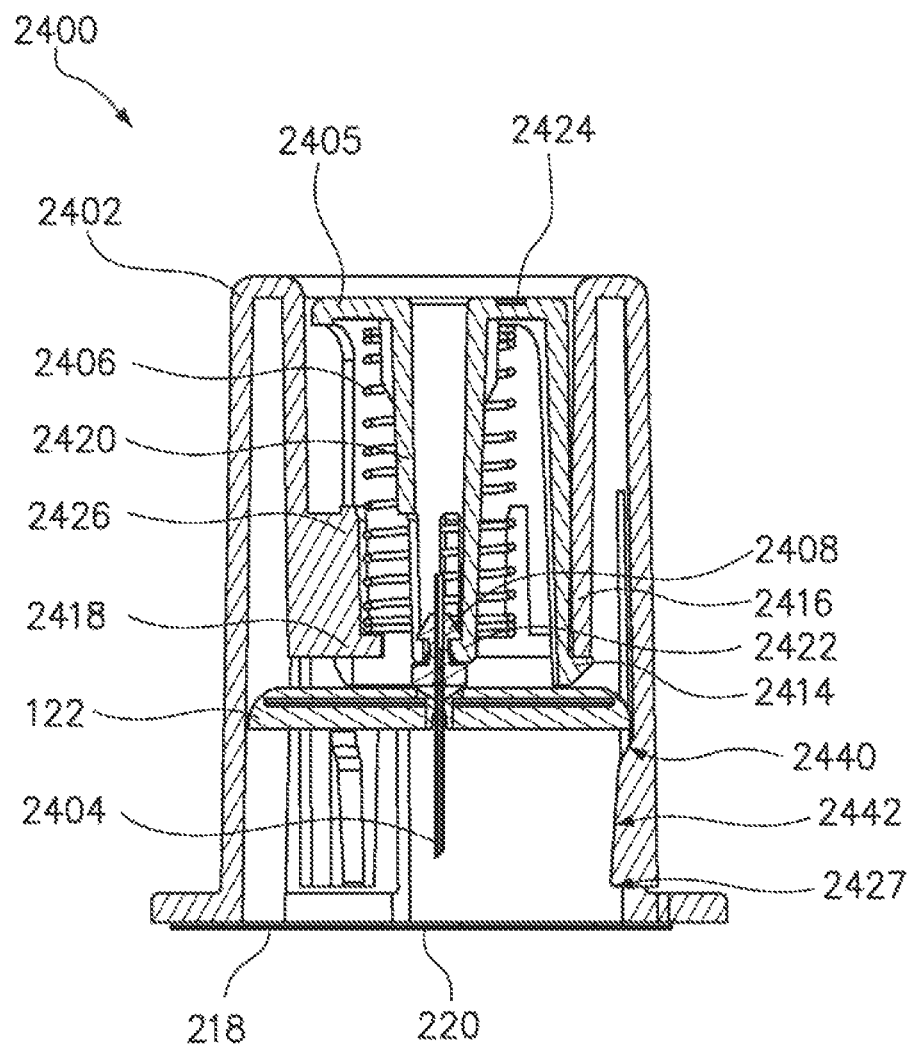
FIGS. 54-58 are cross-sectional views of the inserter of FIG. 44 in accordance with the disclosed subject matter.

FIG. 54 illustrates inserter 2400 in cross-section, in an initial configuration prior to use, after removal of the distal cap 2412. As shown, sharp 2404 extends longitudinally within the inserter 2400. In some embodiments, sharp 2404 is supported at an oblique angle, e.g., between about 0° and 90° with respect to the skin surface.

In some embodiments, sharp 2404 is a solid needle. In some embodiments, sharp 2404 is provided with a substantially cylindrical configuration defining an interior bore, e.g., a rigid cylindrical member or a hypodermic-style needle. Sharp 2404 may also be provided with an elongated longitudinal opening or gap in the wall. In some embodiments, sharp 2404 is fabricated from a sheet of metal and folded into a substantially "V," "U" or "C" configuration in cross-section to define the longitudinal recess.

Depression of plunger 2405 causes distal longitudinal movement of on body housing 122 and sharp 2404 from a proximal position to a distal position. During such downward, distal movement, spring 2406 is further compressed between lip 2418 and bottom surface 2424. Detent 2440 provides a minimum force threshold to overcome before on body housing 122 can continue on its downward distal movement. Beyond a minimum force threshold, detent 2440 is pushed outward by on body housing 122, and on body housing 122 then transitions onto ramp 2442. The friction between on body housing 122 and ramp 2442 of the housing hold the on body housing 122 up against plunger 2405.

Figure 55:
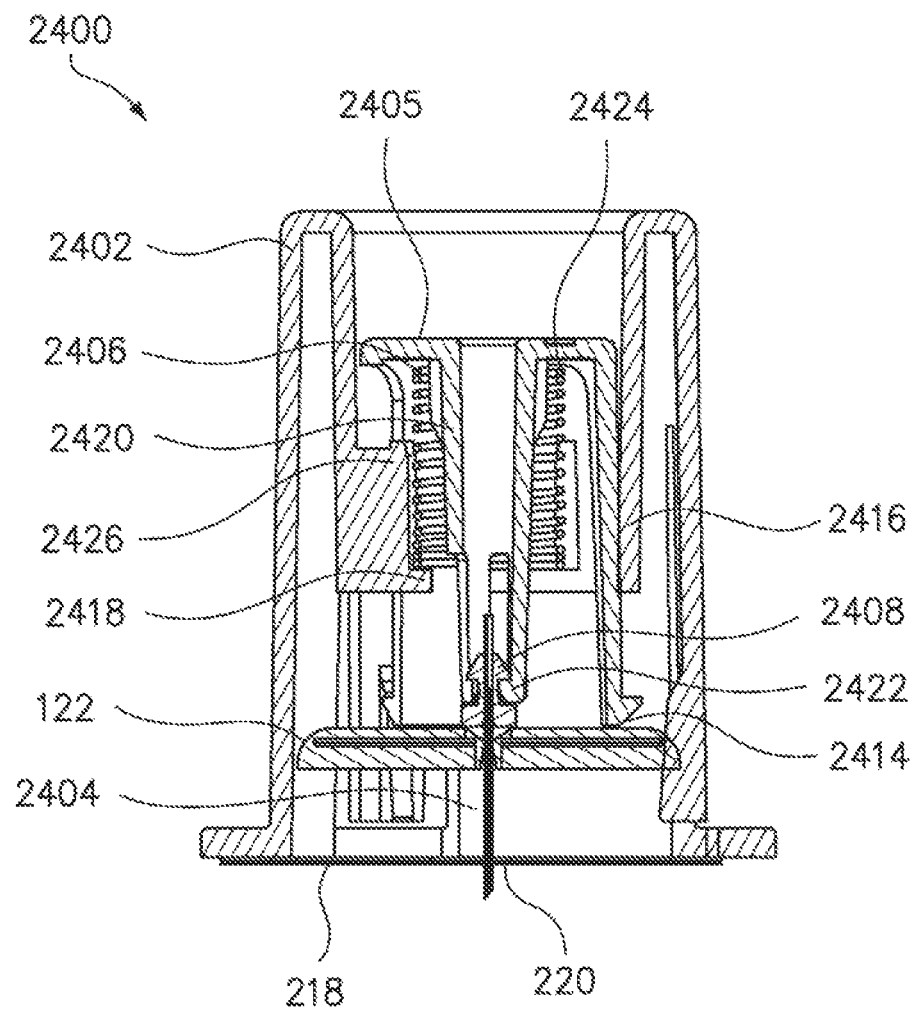

As illustrated in FIG. 55, depression of plunger 2405 advances the inserter 2400 from an initial configuration to a deployed configuration. Contact of plunger 2405 and hub 2408 during depression of plunger 2405 imposes a downward force and consequential distal movement of sharp 2404. As the sharp 2404 is urged distally, it carries the sensor insertion portion 30 into the subcutaneous portion of the subject's skin S (not shown). Contact of plunger 2405 and on body housing 122 during depression of plunger 2405 imposes a downward force and consequential distal movement of on body housing 122. Lip features 2414 of plunger 2405 maintain parallelism of on body housing 122 to subject skin S during distal movement.

Figure 56:
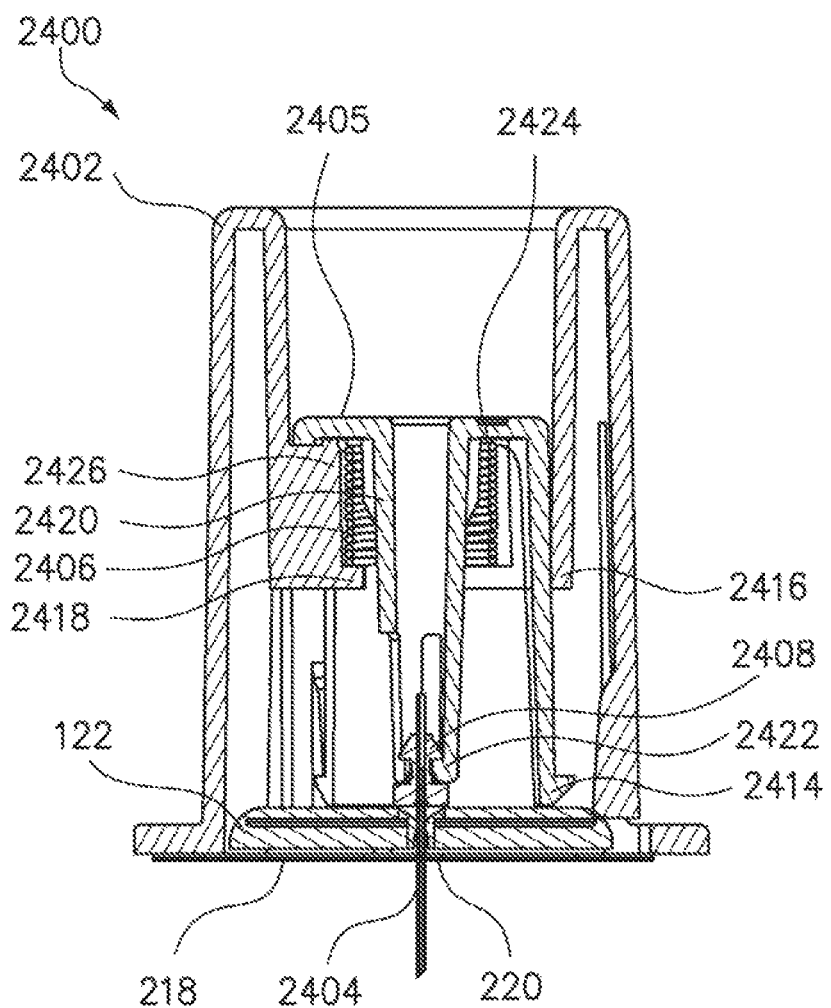

When plunger 2405 reaches a distal position, as shown in FIG. 56, bottom surface 2424 engages wall 2426 and prevents further downward movement. The distal (lower) surface of on body housing 122 engages the upper surface of adhesive pad 218, thereby becoming adhered to the skin surface S of the subject.

Figure 57:
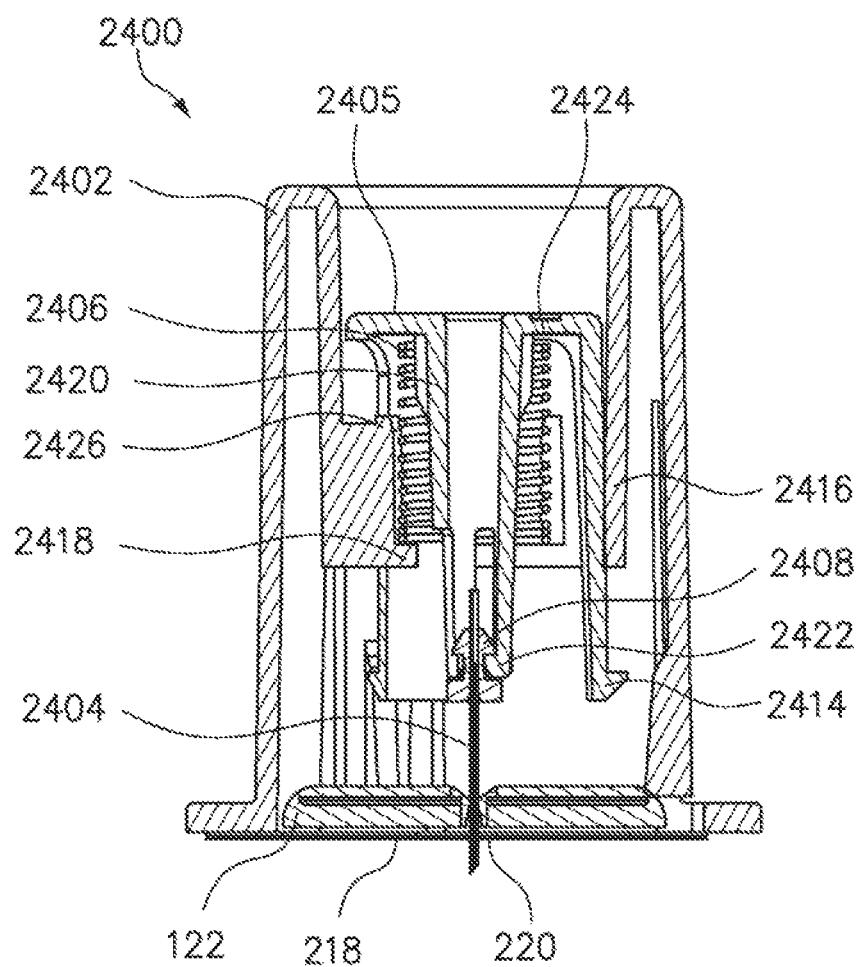
Figure 58:
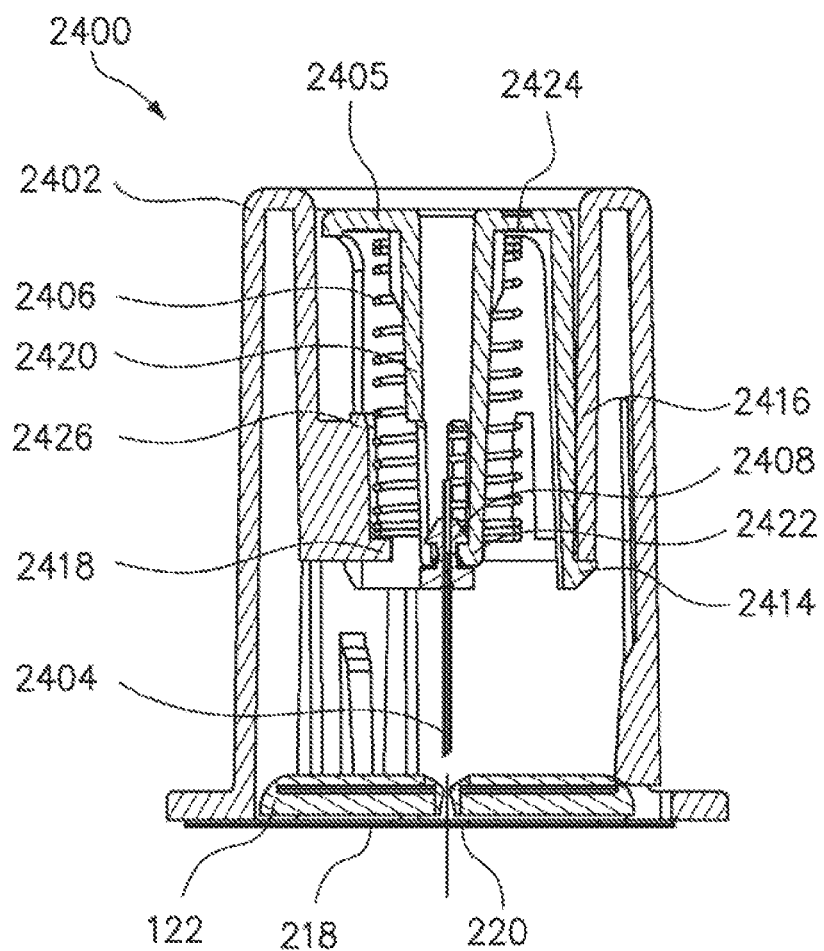

As the subject or some apparatus removes force from plunger 2405, spring 2406 urges plunger 2405 toward its proximal position as shown in FIG. 57, leaving on body housing 122 adhered to the skin surface S of the subject. Tabs 2427 (not shown) provide additional force on on body housing 122 to assist holding it to adhesive patch 218 while the sharp 2404 is withdrawn through on body housing 122. Eventually, the upward force exerted by spring 2406 returns inserter 2400 to its initial configuration as illustrated in FIG. 58.

Figure 59:
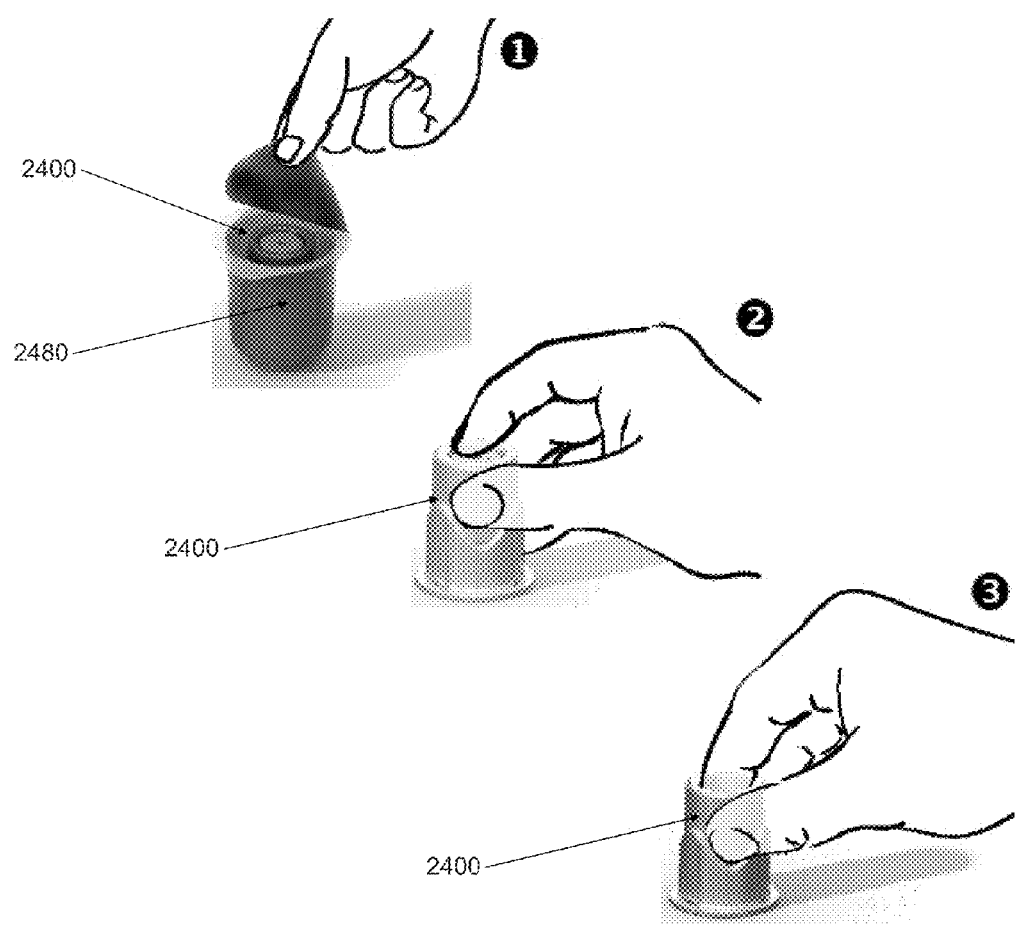
FIG. 59 illustrates a process for utilizing a sterilized version of the inserter of FIG. 44 in accordance with the disclosed subject matter.

In some embodiments, inserter 2400 may be distributed in a sterilized package 2480 as depicted in FIG. 59. To use inserter 2400 in this configuration, a user would first clean the insertion site on the skin with alcohol. The subject would then remove inserter 2400 from sterilized package 2480 as shown in step 1. Next a subject would place the inserter on the insertion site and push down on plunger 2405 until on body housing 122 is adhered to the subject's skin as shown in steps 2-3. The subject would then release the plunger 2405. Finally, the subject would remove inserter 2400 from the insertion site and dispose of the inserter.

Figure 60:
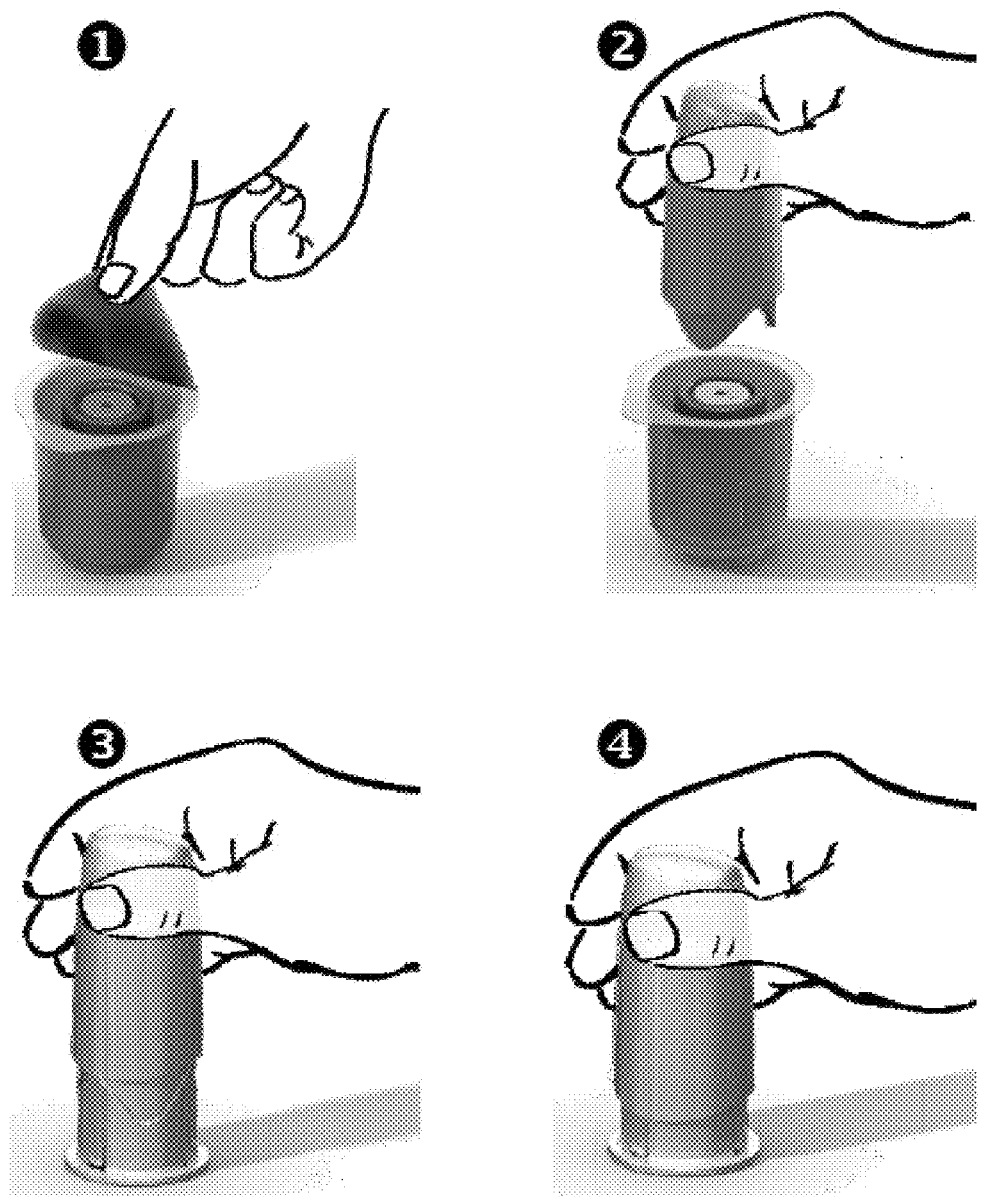
FIG. 60 illustrates an alternate process for utilizing a sterilized version of the inserter of FIG. 44 in accordance with the disclosed subject matter.

In another embodiment, the sterilized inserter 2400 shown in FIG. 59 may be utilized with driver apparatus 3900 (FIGS. 61-79) as shown in FIG. 60. In this manner, insertion of sensor housing unit is semi-automated which may deliver a more consistent user experience and reduce the risk of user error. An exemplary driver apparatus is illustrated in FIGS. 61-79 and designated driver apparatus 3900.

Driver apparatus 3900 includes a housing 3902 for positioning with respect to an inserter. A release button 3904—longitudinally movable with respect to housing 3902—is provided. The force exerted by return spring 3906 allows release button 3904 to be moved between a proximal and distal position, as shown in FIGS. 62-65.

Figure 61:
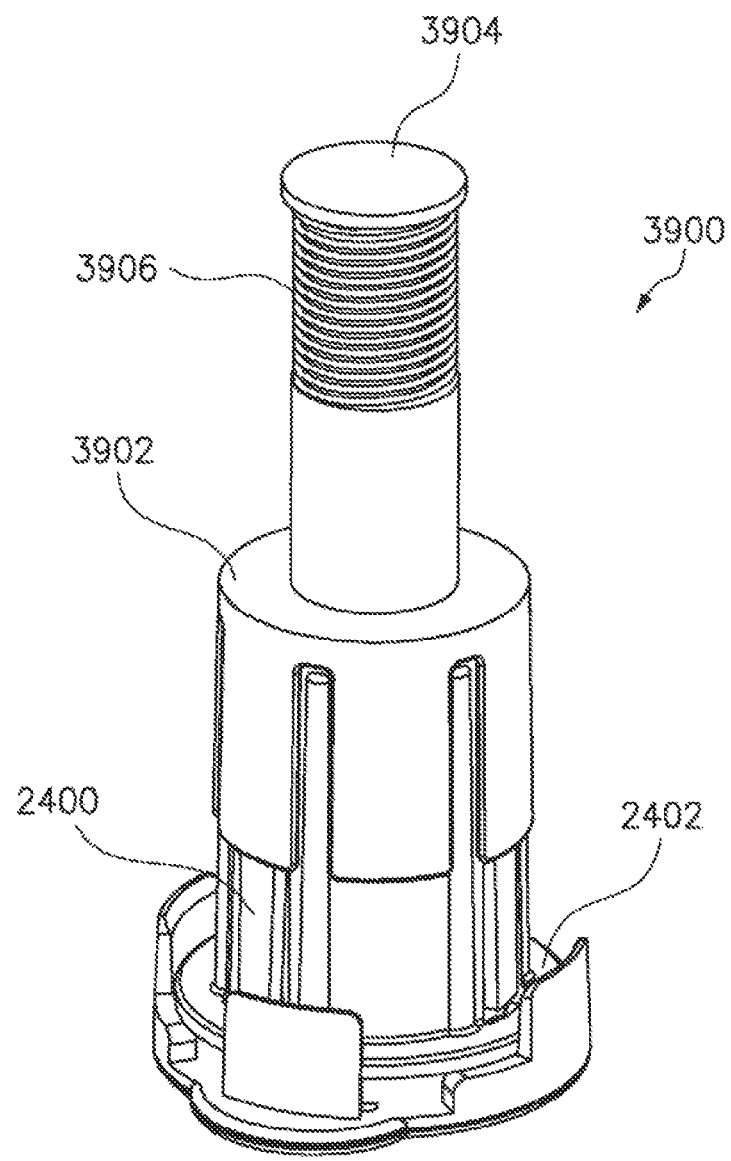
FIG. 61 is a perspective view of an inserter in accordance with the disclosed subject matter.

As illustrated in FIG. 61, the driver apparatus 3900 is positioned with respect to an inserter 2400. Although inserter 2400 is illustrated in FIGS. 44-60, it is understood that any inserter may be used with driver apparatus 3900. Since driver apparatus 3900 and the appropriate inserter may be modular, the dimensions of the housing 3902 and the location and shape of release button 3904 are selected to interact with the dimensions of the inserter. For example, the housing 3902 may be designed for snap-fit or friction-fit cooperation with the sheath 2402 of inserter 2400.

Figure 62:
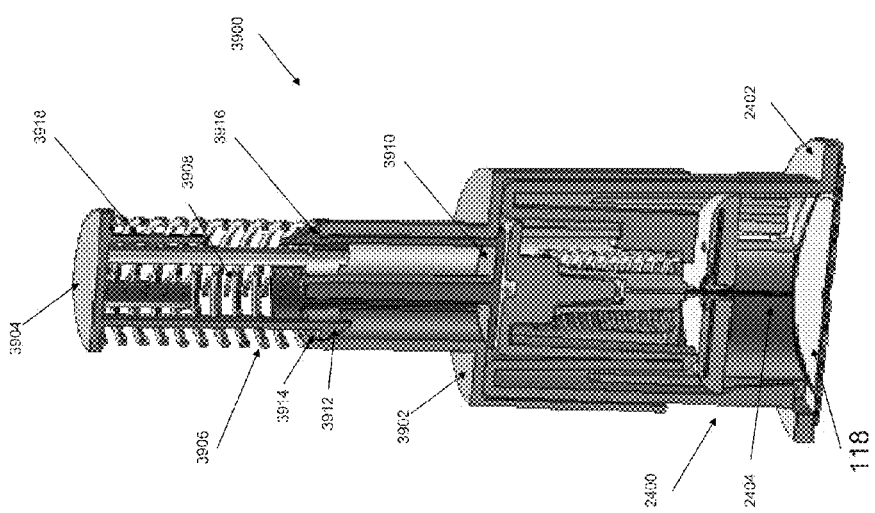
Figure 67:
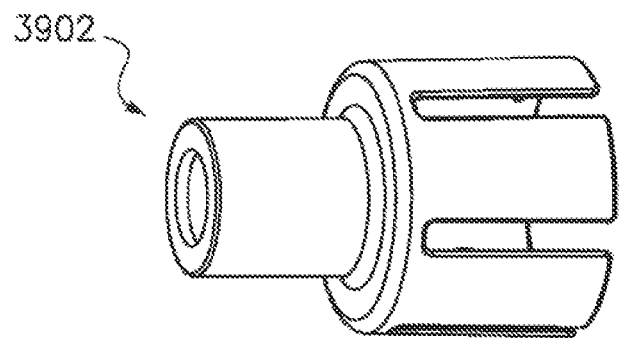
FIGS. 67-69 are perspective views of components of the inserter of FIG. 61 in accordance with the disclosed subject matter.
Figure 68:
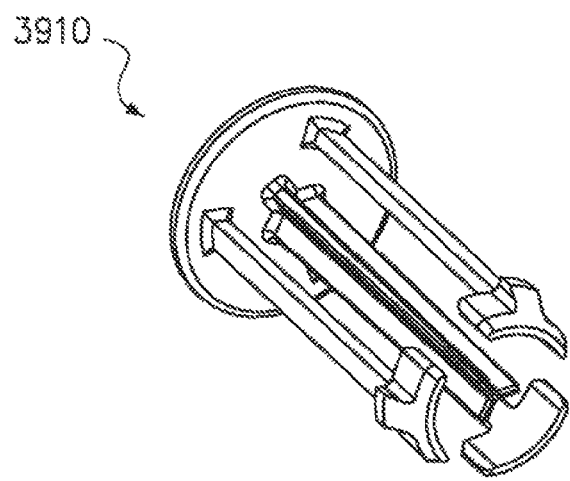
Figure 69:
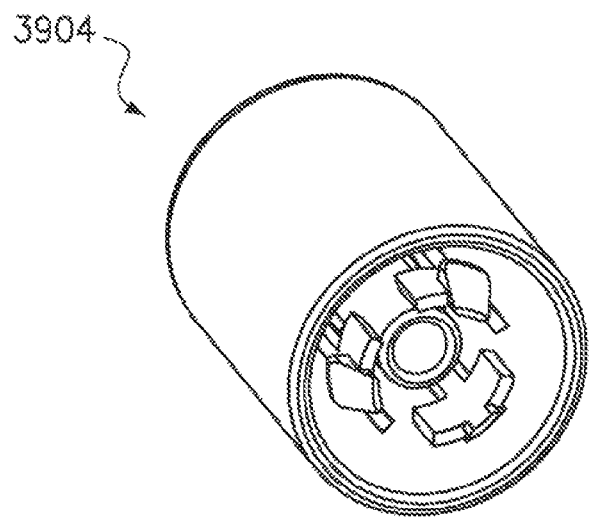

FIGS. 62-65 illustrate the sequence of motions of the driver apparatus 3900 to drive sharp 2404 into the skin of the subject. FIG. 62 illustrates driver apparatus 3900 before firing. As shown, driver apparatus 3900 comprises housing 3902, release button 3904, return spring 3906, driver spring 3908, and plunger 3910. Three-dimensional perspective views of housing 3902, plunger 3910, release button 3904, are depicted in FIGS. 67-69, respectively. Release button 3904 comprises tabs 3912 which engage lip 3914 on housing 3902 which prevent the upward force of return spring 3906 from disengaging release button 3904 and housing 3902 (see FIG. 66). Release button 3904 also comprises protrusion 3918.

Plunger 3910 comprises tabs 3916 (not shown) which confine plunger 3910 to housing 3902. Driver spring 3908 is disposed between the bottom of release button 3904 and the top of plunger 3910. Alternatively, the driver spring 3908 could be around the post shown of plunger 3910 and compressed by the cylinder of button 3904.

Figure 63:
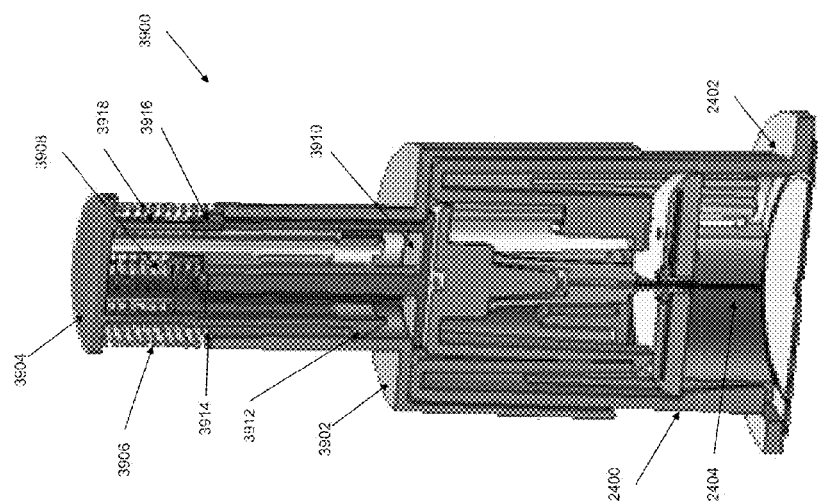
FIGS. 62-66 are cross-sectional views of the inserter of FIG. 61 in accordance with the disclosed subject matter.
Figure 64:
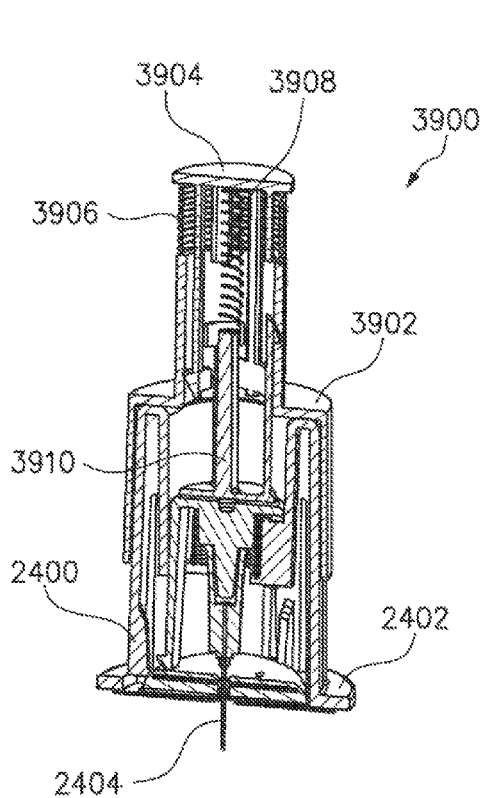

As illustrated in FIG. 63, upon depressing release button 3904 towards housing 3902, return spring 3906 and drive spring 3908 become compressed. Concurrently, protrusion 3918 causes tab 3916 to become disengaged from housing 3902. This allows drive spring 3908 to advance plunger 3910 towards inserter 3900 as shown in FIG. 64. Sharp 2404 which contains sensor therein is driven into the skin of the subject and on body housing 122 is adhered to adhesive pad 118.

Figure 65:
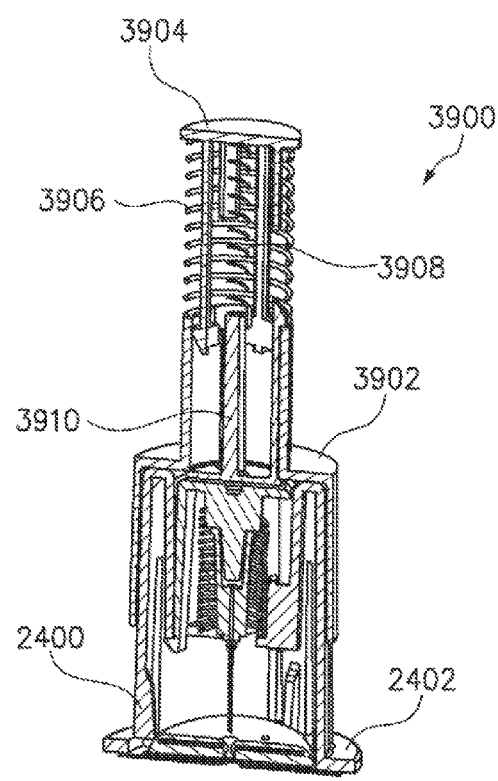
Figure 66:
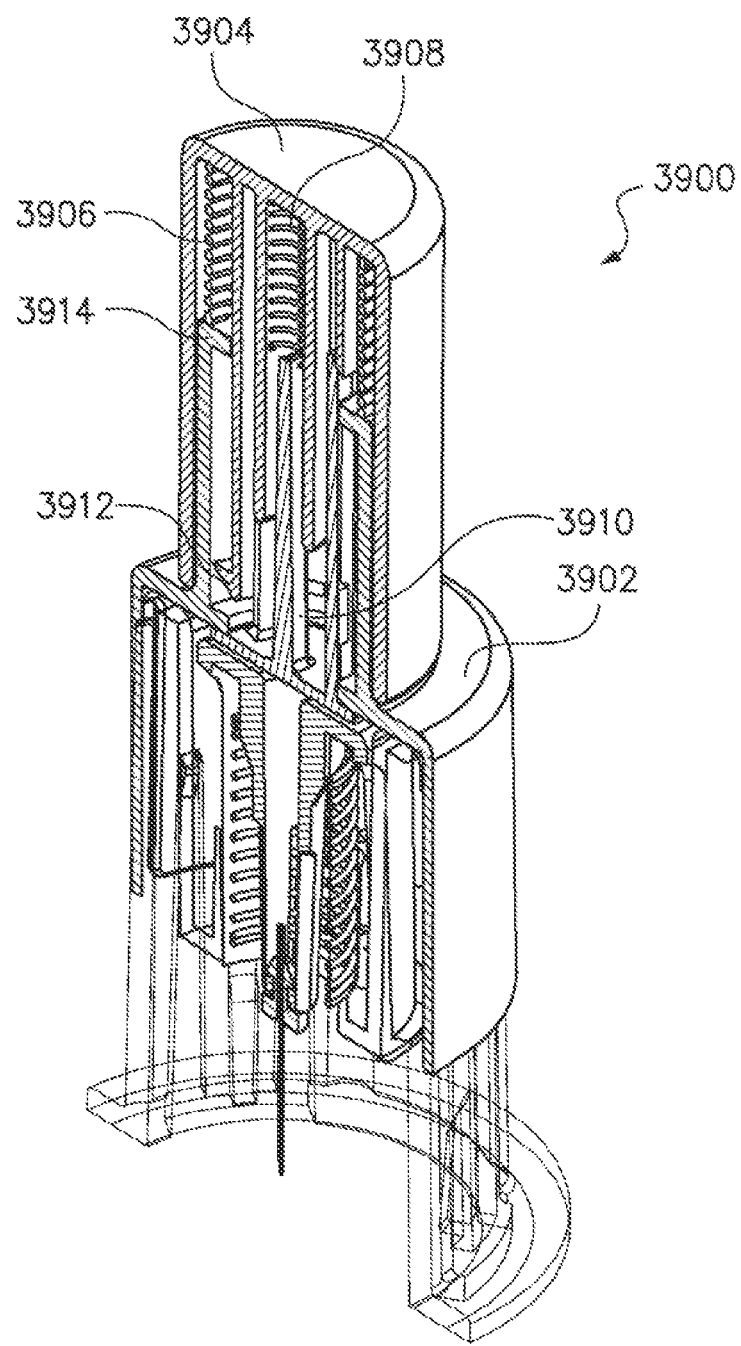

As the subject releases pressure on the button 3904, the return spring 3906 pushes it back to its initial position. As the button 3904 returns, the arms of the button pull the arms of the plunger 3910 back to its initial position, automatically re-engaging the tabs 3916 with the housing 3902 (FIG. 65). The sensor remains inserted in the subject's skin.

An exemplary driver apparatus is illustrated in FIGS. 70-79 and designated driver apparatus 4000.

Driver apparatus 4000 includes a housing 4004 for positioning with respect to an inserter. An outer button 4002—longitudinally movable with respect to housing 4004—is provided. The force exerted by a return spring (not shown) located between housing 4004 and outer button 4002 allows outer button 3904 to be moved between a proximal and distal position, as shown in FIGS. 73-79.

Figure 70:
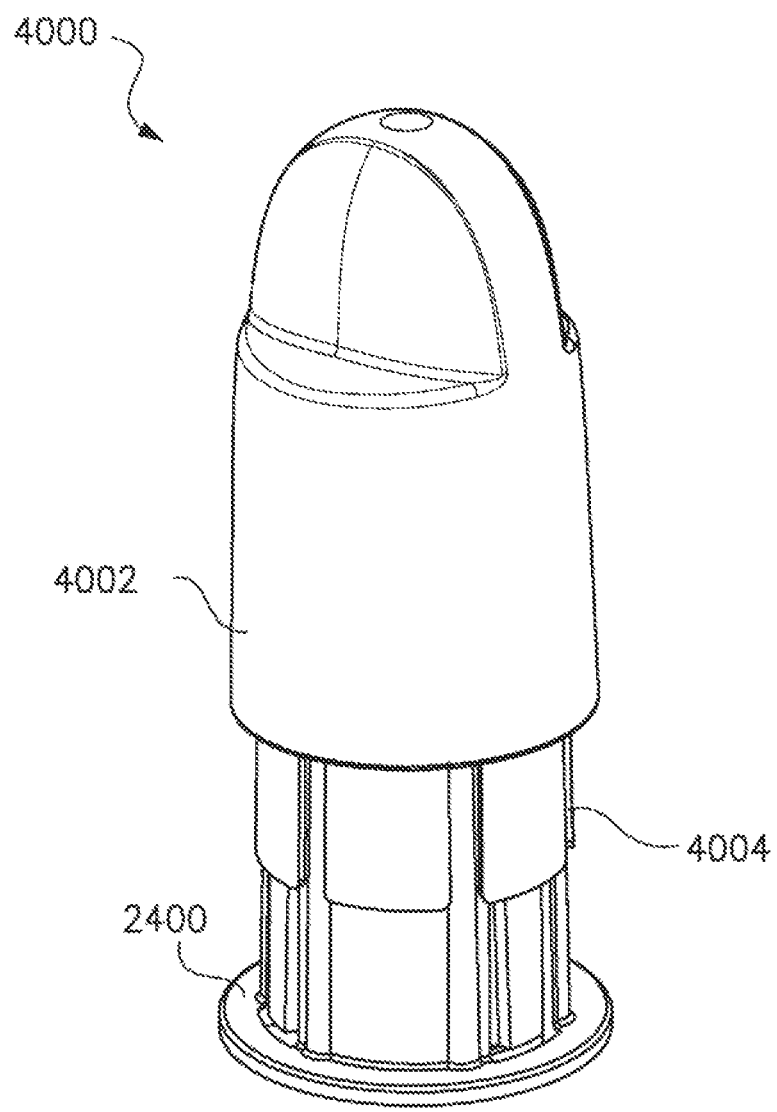
FIG. 70 is a perspective view of an inserter in accordance with the disclosed subject matter.

As illustrated in FIG. 70, the driver apparatus 4000 is positioned on top of inserter 2400. Although inserter 2400 is illustrated in FIGS. 44-58, it is understood that any inserter may be used with driver apparatus 4000. Since driver apparatus 4000 and the appropriate inserter may be modular, the dimensions of the housing 4004 and the location and shape of cam release button 3904 are selected to interact with the dimensions of the inserter. For example, the housing 4004 may be designed for snap-fit or friction-fit cooperation with the sheath of inserter 2400.

Figure 71:
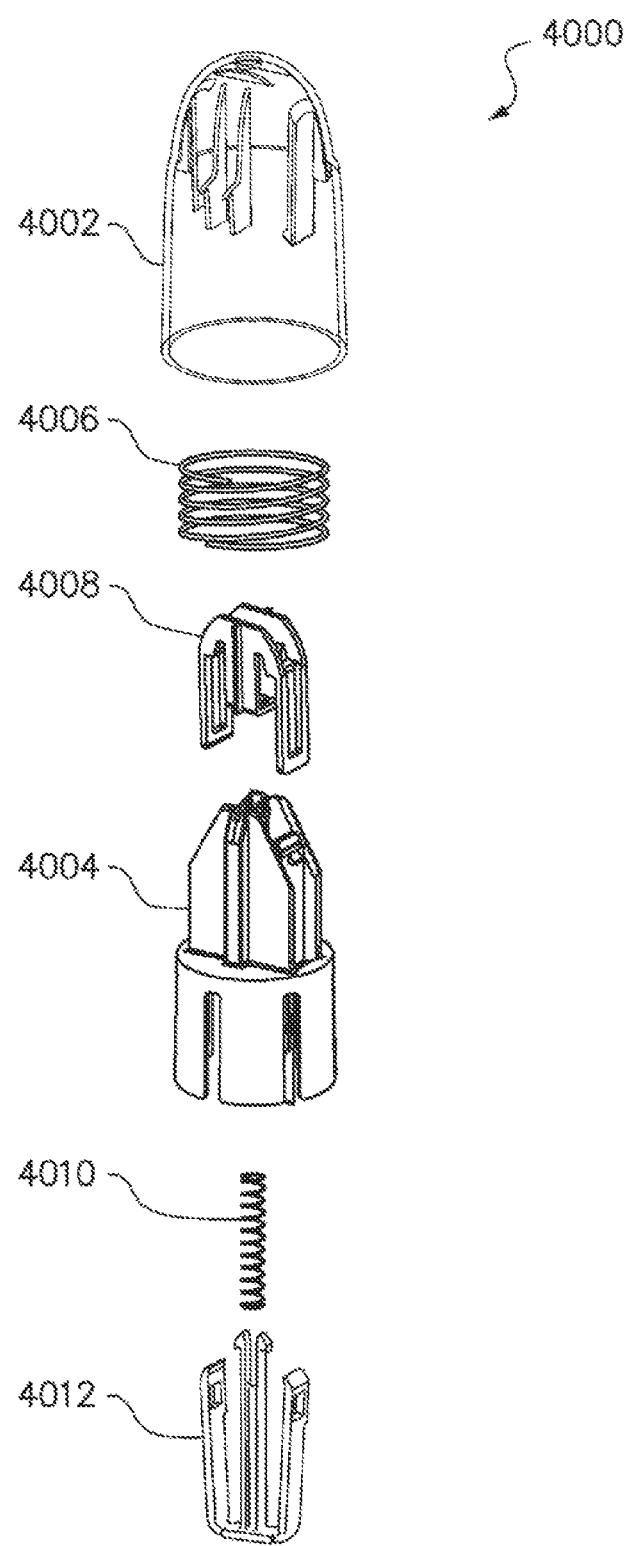
FIG. 71 is a perspective view with parts separated of the inserter of FIG. 70 in accordance with the disclosed subject matter.
Figure 72:
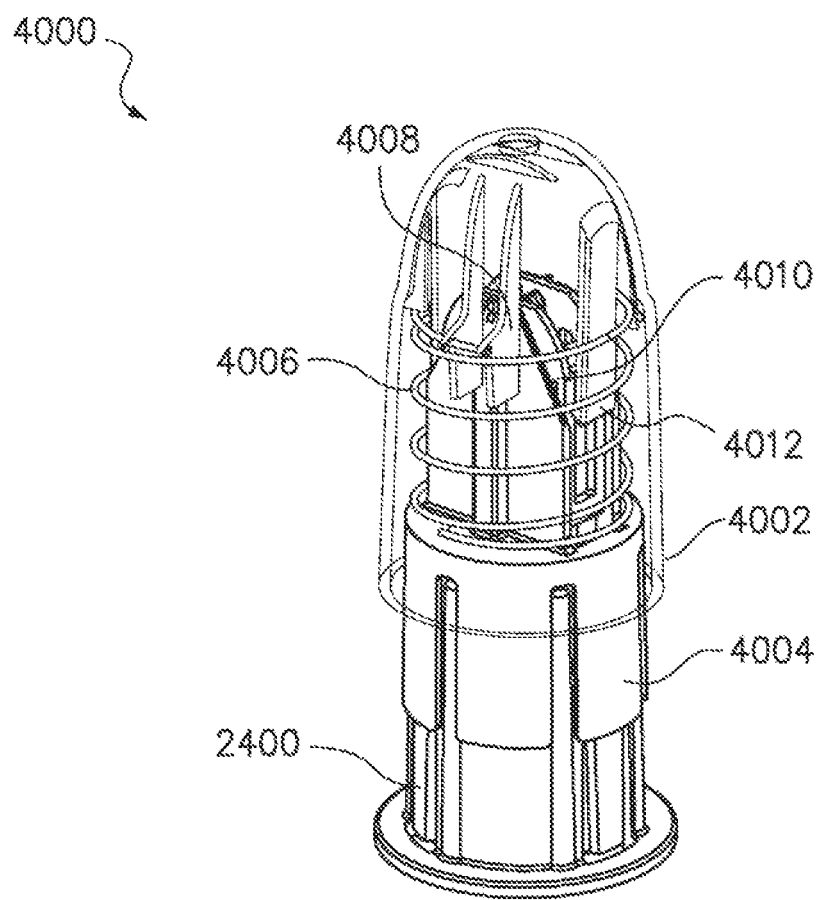
Figure 74:
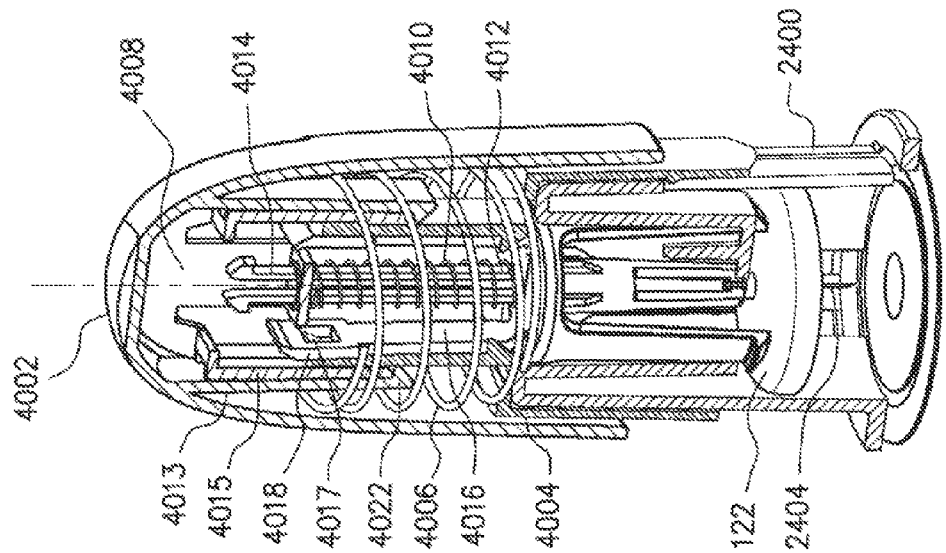

FIG. 71 illustrates an exploded view of the components of driver apparatus 4000. As shown, driver apparatus 4000 comprises outer button 4002, return spring 4006, inner button 4008, housing 4004, drive spring 4010, and plunger 4012. The assembled driver apparatus 4000 is shown in FIG. 72, wherein some components are partially transparent for clarity.

Figure 73:
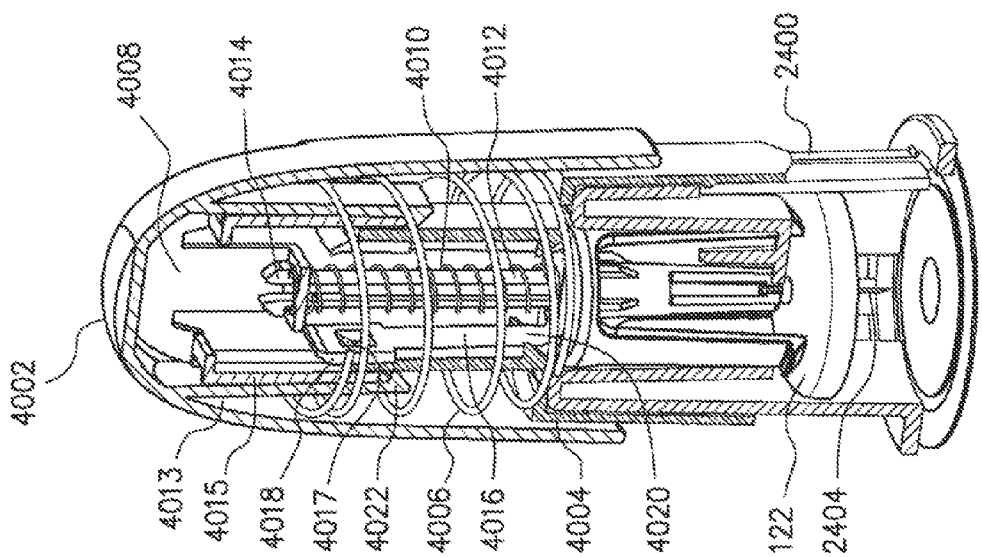

FIGS. 73-79 illustrate the sequence of motions of the driver apparatus 4000 to drive sharp 2404 into the skin of the subject. FIG. 73 illustrates driver apparatus 4000 before firing. When assembled, return spring 4006 is encapsulated between outer button 4002 and housing 4004. Similarly, drive spring 4010 is encapsulated between the bottom of inner button 4008 and surface 4020 located on plunger 4012.

Outer button 4002 comprises guides 4013 which lock inner button 4008 in position using tabs 4022. Inner button 4008 comprises rails 4015 which allow outer button 4002 to move with respect to housing 4004.

Plunger 4012 comprises tabs 4014 which allow it to be fit into and retained within inner button 4008. Furthermore, plunger 4012 comprises arms 4016 having appendages 4018 with openings that engage ledge 4017 on housing 4004.

Figure 75:
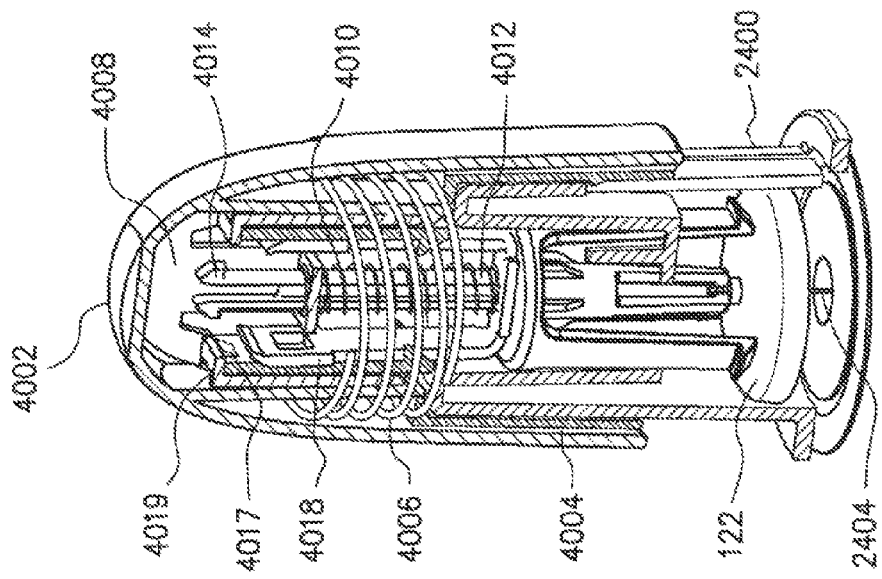

To actuate driver apparatus 4000, a subject pushes down on outer button 4002 in the direction of the subject's skin causing return spring 4006 and driver spring 4010 to become compressed as illustrated in FIG. 75. Eventually, tabs 4019 located on inner button 4008 cause appendages 4018 to be pushed off ledge 4017 as shown in FIG. 76.

Figure 76:
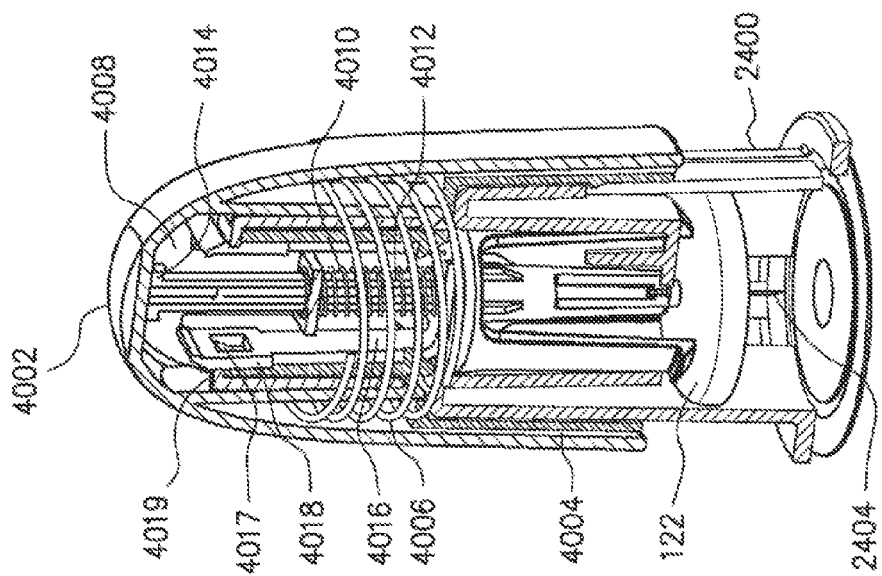

The displacement of appendages 4018 from ledge 4017 allows drive spring 4010 to drive plunger 4012 towards plunger 2405 of inserter 2400 as shown in FIG. 76. Eventually, sharp 2404 is driven into the skin of the subject and on body housing 122 is adhered to the subject as shown in FIG. 77. If there is no inserter 2400 present, the plunger eventually stops its forward motion when the plunger arms engage ledge 4017 or when tabs 4014 engage inner button 4008.

To remove sharp 2404 from the subject's skin, the subject must remove pressure from outer button 4002 which allows return spring 4006 to exert upward pressure on outer housing 4004 as shown in FIG. 78. The guides 4013 pull up the inner button through rails 4015. Inner button 4008 pulls up plunger 4012 by tabs 4014. The plunger 4012 is pulled up far enough to re-engage appendaqes 4018 on ledge 4017. This makes the inserter instantly ready to be re-used with no additional steps. Concurrently, the return spring located in inserter 2400 retracts sharp 2404 from the subject's skin. Return spring 4006 eventually returns driver apparatus 4000 to its original configuration, as shown in FIG. 79.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims.

What is claimed is:

1. A medical device inserter, comprising:
a bellows, a sheath, a removable distal cap defining a sterile environment with a medical device and an inserter sharp housed within the sterile environment, and a carriage shaped with a recess, the recess receiving an on body housing that includes sensor electronics for the medical device, wherein the medical device is an analyte sensor, wherein the bellows is compressible to advance the medical device through a skin layer, and a coil spring set within the bellows is adapted to provide a force for withdrawing the inserter sharp after advancing the medical device through the skin layer, wherein a proximal extent of the bellows provides an actuation portion of the medical device inserter, and further wherein the bellows provides the actuation portion of the medical device inserter such that a manual force applied to the actuation portion causes a compression of the coil spring set within the bellows and a downward force to be applied to the carriage.

2. The inserter of claim 1, wherein the removable distal cap is threaded to the sheath.

3. The inserter of claim 1, wherein the medical device inserter is adapted so the bellows alone, provides the force for withdrawing the inserter sharp after advancing the medical device through the skin layer.

4. The inserter of claim 1, wherein the bellows comprises a series of concentric folds.

5. The inserter of claim 4, wherein the bellows comprises raised portions and folded portions.

6. The inserter of claim 1, wherein a distal extent of the sheath provides an interface with the skin layer.

7. The inserter of claim 1, wherein the analyte sensor comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

8. The inserter of claim 1, wherein the sheath includes a distal end and a proximal end.

9. The inserter of claim 8, wherein the distal end of the sheath is configured for placement on the skin layer, and the bellows is compressible to advance the medical device from the proximal end of the sheath to the distal end of the sheath through the skin layer.

* * * * *